United States Patent
Coburn et al.

(10) Patent No.: US 9,254,292 B2
(45) Date of Patent: Feb. 9, 2016

(54) FUSED TETRACYCLE DERIVATIVES AND METHODS OF USE THEREOF FOR THE TREATMENT OF VIRAL DISEASES

(75) Inventors: Craig A. Coburn, Royersford, PA (US); Brian J. Lavey, New Providence, NJ (US); Michael P. Dwyer, Scotch Plains, NJ (US); Joseph A. Kozlowski, Princeton, NJ (US); Stuart B. Rosenblum, West Orange, NJ (US)

(73) Assignee: Merck Sharp & Dohme Corp., Rahway, NJ (US)

( * ) Notice: Subject to any disclaimer, the term of this patent is extended or adjusted under 35 U.S.C. 154(b) by 0 days.

(21) Appl. No.: 13/876,931

(22) PCT Filed: Sep. 28, 2011

(86) PCT No.: PCT/US2011/053557
§ 371 (c)(1),
(2), (4) Date: Mar. 29, 2013

(87) PCT Pub. No.: WO2012/050848
PCT Pub. Date: Apr. 19, 2012

(65) Prior Publication Data
US 2014/0170111 A1    Jun. 19, 2014

Related U.S. Application Data

(60) Provisional application No. 61/387,499, filed on Sep. 29, 2010.

(51) Int. Cl.
*A61K 31/553*    (2006.01)
*C07D 403/14*    (2006.01)
*C07D 405/14*    (2006.01)
*C07D 493/04*    (2006.01)
*C07D 498/04*    (2006.01)
*A61K 31/4178*   (2006.01)
*A61K 31/5517*   (2006.01)
*A61K 45/06*     (2006.01)
*C07D 487/04*    (2006.01)

(52) U.S. Cl.
CPC ........... *A61K 31/553* (2013.01); *A61K 31/4178* (2013.01); *A61K 31/5517* (2013.01); *A61K 45/06* (2013.01); *C07D 403/14* (2013.01); *C07D 405/14* (2013.01); *C07D 487/04* (2013.01); *C07D 493/04* (2013.01); *C07D 498/04* (2013.01)

(58) Field of Classification Search
CPC .. C07D 403/14; C07D 405/14; C07D 493/04; C07D 498/04; C07D 487/04; A61K 31/5517; A61K 45/06; A61K 31/553; A61K 31/4178
See application file for complete search history.

(56) References Cited

U.S. PATENT DOCUMENTS

| 7,153,848 | B2 | 12/2006 | Hudyma et al. |
| 7,662,809 | B2 | 2/2010 | Ercolani et al. |
| 7,973,040 | B2 | 7/2011 | Harper et al. |
| 8,080,654 | B2 | 12/2011 | Harper et al. |
| 8,377,980 | B2 | 2/2013 | Belema et al. |
| 8,871,759 | B2 | 10/2014 | Coburn et al. |
| 2006/0019974 | A1 | 1/2006 | Mederski et al. |
| 2006/0258682 | A1 | 11/2006 | Liao et al. |
| 2007/0049593 | A1 | 3/2007 | Oka et al. |
| 2007/0110708 | A1 | 5/2007 | Miller et al. |
| 2007/0185175 | A1 | 8/2007 | Liu et al. |
| 2008/0299075 | A1 | 12/2008 | Bachand et al. |
| 2009/0004111 | A1 | 1/2009 | Rice et al. |
| 2009/0042860 | A1 | 2/2009 | Bergstrom et al. |
| 2010/0316607 | A1 | 12/2010 | Or et al. |
| 2011/0104109 | A1 | 5/2011 | Bennett et al. |
| 2011/0130361 | A1 | 6/2011 | Grimm et al. |

(Continued)

FOREIGN PATENT DOCUMENTS

CN        101336248    12/2008
JP         10101591     4/1984

(Continued)

OTHER PUBLICATIONS

Alper, P.B., Discovery and Biological Evaluation of Benzo[z]Carbazole-based Small Molecular Agonists of the Thrombopoietin (Tpo) Receptor, Bioorganic and Medicinal Chem. Lett., 2008, pp. 5255-5258, vol. 18, US.
CAPLUS Accession No. 1980:471599.
CAPLUS Accession No. 2009:295362 (JP2009-054809).
CAR RN 1025830-17-4, STN ENTRY, Jun. 5, 2008.
CN1474815—English Abstract—Corresponding to US Application No. US2006/0019974, (2006).
Marsilje, T.H., et al, Optimization of Small Molecule Agonists of the Thrombopoietin (Tpo) Receptor Derived From a Benzo[a]Carbazole Hit Scaffold, Bioorganic and Medicinal Chem. Lett., 2008, pp. 5259-5262, vol. 18, US.
Wilson, et al, Tunable DNA Photocleavage by an Acridine-Imidazole Conjugate, Inorganic Chemistry, 2005, pp. 6159-6173, vol. 44, No. 18, US.

*Primary Examiner* — Savitha Rao
*Assistant Examiner* — Angela Brown-Pettigrew
(74) *Attorney, Agent, or Firm* — Jeffrey P. Bergman; Mark R. Daniel

(57) ABSTRACT

The present invention relates to novel Fused Tetracycle Derivatives of Formula (I): and pharmaceutically acceptable salts thereof, wherein A, A', B, G, $R^1$, U, V, W, W', X, X', Y and Y' are as defined herein. The present invention also relates to compositions comprising at least one Fused Tetracycle Derivative, and methods of using the Fused Tetracycle Derivatives for treating or preventing HCV infection in a patient.

(I)

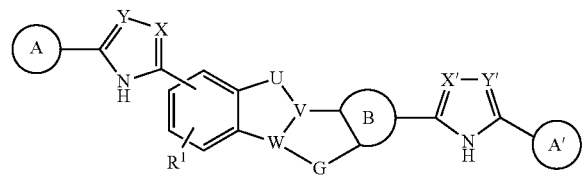

9 Claims, No Drawings

(56) References Cited

U.S. PATENT DOCUMENTS

| | | |
|---|---|---|
| 2011/0223134 A1 | 9/2011 | Nair et al. |
| 2011/0224211 A1 | 9/2011 | Schmitz et al. |
| 2012/0040962 A1 | 2/2012 | Li et al. |
| 2012/0083448 A1 | 4/2012 | Xu et al. |
| 2012/0083483 A1* | 4/2012 | Coburn et al. ........... 514/211.09 |
| 2013/0156731 A1 | 6/2013 | Chen et al. |
| 2013/0164258 A1 | 6/2013 | Chen et al. |
| 2013/0280214 A1 | 10/2013 | Vacca et al. |
| 2014/0170111 A1 | 6/2014 | Coburn et al. |
| 2014/0199264 A1 | 7/2014 | Coburn et al. |
| 2014/0371138 A1 | 12/2014 | Coburn et al. |
| 2014/0377223 A1 | 12/2014 | Kozlowski et al. |

FOREIGN PATENT DOCUMENTS

| | | |
|---|---|---|
| WO | WO2006020082 A2 | 2/2006 |
| WO | EP1719773 A1 | 11/2006 |
| WO | WO2007009120 A2 | 1/2007 |
| WO | WO2007084413 A2 | 7/2007 |
| WO | WO2009023179 A2 | 2/2009 |
| WO | WO2010041687 A1 | 4/2010 |
| WO | WO2010065674 A1 | 6/2010 |
| WO | WO201011483 A1 | 9/2010 |
| WO | WO2012040923 A1 | 4/2012 |
| WO | WO2012050850 A1 | 4/2012 |
| WO | WO20120401014 A1 | 4/2012 |
| WO | WO2009102325 A1 | 8/2014 |

* cited by examiner

FUSED TETRACYCLE DERIVATIVES AND METHODS OF USE THEREOF FOR THE TREATMENT OF VIRAL DISEASES

CROSS-REFERENCE TO RELATED APPLICATIONS

This application is the national stage application under 35 U.S.C. 371 of International Patent Application No. PCT/US2011/053557, filed Sep. 28, 2011, which claims priority to U.S. Provisional Application No. 61/387,499, filed Sep. 29, 2010. Each of the aforementioned PCT and priority applications is incorporated by reference in its entirety.

REFERENCE TO SEQUENCE LISTING SUBMITTED ELECTRONICALLY

The sequence listing of the present application is submitted electronically via EFS-Web as an ASCII formatted sequence listing with a file name "IN2010.7166-US-PCT_SEQ.LIST.TXT," creation date of Apr. 28, 2014, and a size of 1 KB. This sequence listing submitted via EFS-Web is cart of the specification and is herein incorporated by reference in its entirety.

FIELD OF THE INVENTION

The present invention relates to novel Fused Tetracycle Derivatives, compositions comprising at least one Fused Tetracycle Derivative, and methods of using the Fused Tetracycle Derivatives for treating or preventing HCV infection in a patient.

BACKGROUND OF THE INVENTION

Hepatitis C virus (HCV) is a major human pathogen. A substantial fraction of these HCV-infected individuals develop serious progressive liver disease, including cirrhosis and hepatocellular carcinoma, which are often fatal. HCV is a (+)-sense single-stranded enveloped RNA virus that has been implicated as the major causative agent in non-A, non-B hepatitis (NANBH), particularly in blood-associated NANBH (BB-NANBH) (see, International Publication No. WO 89/04669 and European Patent Publication No. EP 381 216). NANBH is to be distinguished from other types of viral-induced liver disease, such as hepatitis A virus (HAV), hepatitis B virus (HBV), delta hepatitis virus (HDV), cytomegalovirus (CMV) and Epstein-Barr virus (EBV), as well as from other forms of liver disease such as alcoholism and primary biliar cirrhosis.

It is well-established that persistent infection of HCV is related to chronic hepatitis, and as such, inhibition of HCV replication is a viable strategy for the prevention of hepatocellular carcinoma. Current therapies for HCV infection include α-interferon monotherapy and combination therapy comprising α-interferon and ribavirin. These therapies have been shown to be effective in some patients with chronic HCV infection, but suffer from poor efficacy and unfavorable side-effects and there are currently efforts directed to the discovery of HCV replication inhibitors that are useful for the treatment and prevention of HCV related disorders.

Current research efforts directed toward the treatment of HCV includes the use of antisense oligonucleotides, free bile acids (such as ursodeoxycholic acid and chenodeoxycholic acid) and conjugated bile acids (such as tauroursodeoxycholic acid). Phosphonoformic acid esters have also been proposed as potentially useful for the treatment of various viral infections, including HCV. Vaccine development, however, has been hampered by the high degree of viral strain heterogeneity and immune evasion and the lack of protection against reinfection, even with the same inoculum.

In light of these treatment hurdles, the development of small-molecule inhibitors directed against specific viral targets has become a major focus of anti-HCV research. The determination of crystal structures for NS3 protease, NS3 RNA helicase, NS5A, and NS5B polymerase, with and without bound ligands, has provided important structural insights useful for the rational design of specific inhibitors.

Recent attention has been focused toward the identification of inhibitors of HCV NS5A. HCV NS5A is a 447 amino acid phosphoprotein which lacks a defined enzymatic function. It runs as 56 kd and 58 kd bands on gels depending on phosphorylation state (Tanji, et al. *J. Virol.* 69:3980-3986 (1995)). HCV NS5A resides in replication complex and may be responsible for the switch from replication of RNA to production of infectious virus (Huang, Y, et al., *Virology* 364:1-9 (2007)).

Mulficyclic HCV NS5A inhibitors have been reported. See U.S. Patent Publication Nos. US20080311075, US20080044379, US20080050336, US20080044380, US20090202483 and US2009020478. HCV NS5A inhibitors having fused tricyclic moieties are disclosed in International Patent Publication Nos. WO 10/065681, WO 10/065668, and WO 10/065,674.

Other HCV NS5A inhibitors and their use for reducing viral load in HCV infected humans have been described in U.S. Patent Publication No. US20060276511.

SUMMARY OF THE INVENTION

In one aspect, the present invention provides Compounds of Formula (I):

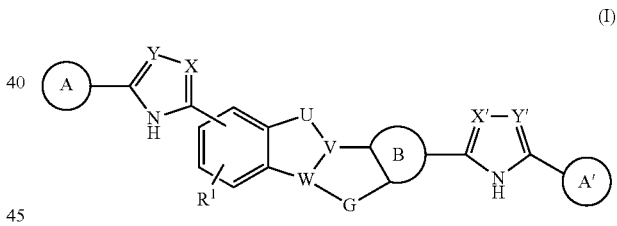

and pharmaceutically acceptable salts thereof, wherein:

A and A' are each independently selected from 5 or 6-membered monocyclic heterocycloalkyl, wherein said 5 or 6-membered monocyclic heterocycloalkyl group can be optionally fused to an aryl group; and wherein said 5 or 6-membered monocyclic heterocycloalkyl group can be optionally and independently substituted on one or more ring carbon atoms with $R^{13}$, such that any two $R^{13}$ groups on the same ring, together with the carbon atoms to which they are attached, can join to form a fused, bridged or spirocyclic 3 to 6-membered cycloalkyl group or a fused, bridged or spirocyclic 4 to 6-membered heterocycloalkyl group, wherein said 5 or 6-membered monocyclic heterocycloalkyl contains from 1 to 2 ring heteroatoms, each independently selected from $N(R^4)$, S, O and $Si(R^{16})_2$;

ring B is selected from phenyl or a 5 or 6-membered heteroaryl group, wherein said phenyl group and said 5 or 6-membered heteroaryl group can be optionally substituted on up to 2 ring carbon atoms with $R^{15}$;

G is selected from —$C(R^3)_2$—, —$N(R^5)$—, —O—, —$SO_2$—, —$C(R^3)_2$—$C(R^3)_2$—O—, —$C(R^3)_2$—$C(R^3)_2$—

—N($R^5$)—, —C($R^3$)$_2$—C(O)—N($R^5$)—, —C(O)—C($R^3$)$_2$—C($R^3$)$_2$—, —C($R^3$)$_2$—C($R^3$)—C(O)—, —C($R^3$)$_2$—C($R^3$)$_2$—C($R^3$)$_2$—, —C($R^3$)$_2$—O—, —C($R^3$)$_2$—C($R^3$)$_2$— and —C($R^{14}$)=C($R^{14}$)—, such that when G is —C($R^3$)$_2$—O—, —C($R^{14}$)=N—, —C($R^3$)$_2$—C($R^3$)$_2$— or —C($R^{14}$)=C($R^{14}$)—, then B is a 5-membered heteroaryl group;

the group —U—V—W— is —C($R^2$)=C—N—, —O—C=C—, —N($R^5$)—C=C— and —SO$_2$—C=C—, such that when G is —C($R^3$)$_2$—, —N($R^5$)—, —O— or —SO$_2$—, then the group U—V—W is —N($R^5$)—C=C—;

X and X' are each independently selected from N and C($R^{10}$);

Y and Y' are each independently selected from N and C($R^{10}$);

$R^1$ represents from 0 to 3 ring carbon substituents on the 6-membered ring to which $R^1$ is attached, wherein said substituents can be the same or different, and are selected from $C_1$-$C_6$ alkyl, halo, —OH, —O—($C_1$-$C_6$ alkyl), $C_1$-$C_6$ haloalkyl and —O—($C_1$-$C_6$ haloalkyl);

each occurrence of $R^2$ is independently selected from H, $C_1$-$C_6$ alkyl, halo, —OH, —O—($C_1$-$C_6$ alkyl), $C_1$-$C_6$ haloalkyl and —O—($C_1$-$C_6$ haloalkyl);

each occurrence of $R^3$ is independently selected from H, $C_1$-$C_6$ alkyl, $C_1$-$C_6$ haloalkyl, —($C_1$-$C_6$ alkylene)-O—($C_1$-$C_6$ alkyl), 3 to 6-membered cycloalkyl, 4 to 6-membered heterocycloalkyl, aryl, 5 or 6-membered heteroaryl, —CH$_2$-(5 or 6 membered heteroaryl) and benzyl, wherein said aryl group, said 5 or 6-membered heteroaryl group or the phenyl moiety of said benzyl group can be optionally substituted with up to 3 groups, which can be the same or different, and are selected from $C_1$-$C_6$ alkyl, $C_1$-$C_6$ haloalkyl, —O—($C_1$-$C_6$ alkyl), —O($C_1$-$C_6$ haloalkyl), halo, —($C_1$-$C_6$ alkylene)-O—($C_1$-$C_6$ alkyl) and —CN and wherein two $R^3$ groups attached to the same carbon atom, together with the common carbon atom to which they are attached, can join to form a carbonyl group, a 3 to 6-membered spirocyclic cycloalkyl group or a 3 to 6-membered spirocyclic heterocycloalkyl group;

each occurrence of $R^4$ is independently selected from —[C($R^7$)$_2$]$_q$N($R^6$)$_2$, —C(O)$R^{11}$, —C(O)—[C($R^7$)$_2$]$_q$N($R^6$)$_2$, —C(O)—[C($R^7$)$_2$]$_q$—$R^{11}$, —C(O)—[C($R^7$)$_2$]$_q$N($R^6$)C(O)—$R^{11}$, —C(O)[C($R^7$)$_2$]$_q$N($R^6$)SO$_2$—$R^{11}$, —C(O)—[C($R^7$)$_2$]$_q$N($R^6$)C(O)O—$R^{11}$, —C(O)—[C($R^7$)$_2$]$_q$C(O)O—$R^{11}$ and -alkylene-N($R^6$)—[C($R^7$)$_2$]$_q$—N($R^6$)—C(O)O—$R^{11}$;

each occurrence of $R^{15}$ is independently selected from H, $C_1$-$C_6$ alkyl, —($C_1$-$C_6$ alkylene)-O—($C_1$-$C_6$ alkyl), 3 to 6-membered cycloalkyl, 4 to 6-membered heterocycloalkyl, aryl, 5 or 6-membered heteroaryl and benzyl, wherein said aryl group, said 5 or 6-membered heteroaryl group or the phenyl moiety of said benzyl group can be optionally substituted with up to 3 groups, which can be the same or different, and are selected from $C_1$-$C_6$ alkyl, $C_1$-$C_6$ haloalkyl, —O—($C_1$-$C_6$ alkyl), —O—($C_1$-$C_6$ haloalkyl), halo, —($C_1$-$C_6$ alkylene)-O—($C_1$-$C_6$ alkyl) and —CN;

each occurrence of $R^6$ is independently selected from H, $C_1$-$C_6$ alkyl, 3 to 6-membered cycloalkyl, 4 to 6-membered heterocycloalkyl, aryl and 5 or 6-membered heteroaryl, wherein said 3 to 6-membered cycloalkyl group, said 4 to 6-membered heterocycloalkyl group, said aryl group and said 5 or 6-membered heteroaryl group can be optionally and independently substituted with up to two $R^8$ groups, and wherein two $R^6$ groups that are attached to the same nitrogen atom, together with the common nitrogen atom to which they are attached, can join to form a 4 to 6-membered heterocycloalkyl group;

each occurrence of $R^7$ is independently selected from H, $C_1$-$C_6$ alkyl, $C_1$-$C_6$ haloalkyl, -alkylene-O—($C_1$-$C_6$ alkyl), 3 to 6-membered cycloalkyl, 4 to 6-membered heterocycloalkyl, aryl and 5 or 6-membered heteroaryl, wherein said 3 to 6-membered cycloalkyl group, said 4 to 6-membered heterocycloalkyl group, said aryl group and said 5 or 6-membered heteroaryl group can be optionally substituted with up to three $R^8$ groups;

each occurrence of $R^8$ is independently selected from H, $C_1$-$C_6$ alkyl, halo, —$C_1$-$C_6$haloalkyl, $C_1$-$C_6$ hydroxyalkyl, —OH, —C(O)NH—($C_1$-$C_6$ alkyl), —C(O)N($C_1$-$C_6$ alkyl)$_2$, O—($C_1$-$C_6$ alkyl), —NH$_2$, —NH($C_1$-$C_6$ alkyl), —N($C_1$-$C_6$ alkyl)$_2$ and —NHC(O)—($C_1$-$C_6$ alkyl);

each occurrence of $R^9$ is independently selected from H, $C_1$-$C_6$ alkyl, $C_1$-$C_6$ haloalkyl, 3 to 6-membered cycloalkyl, 4 to 6-membered heterocycloalkyl, aryl and 5 or 6-membered heteroaryl;

each occurrence of $R^{10}$ is independently selected from H, $C_1$-$C_6$ alkyl, $C_1$-$C_6$ haloalkyl, halo, —OH, —O—($C_1$-$C_6$ alkyl) and —CN;

each occurrence of $R^{11}$ is independently selected from H, $C_1$-$C_6$ alkyl, $C_1$-$C_6$ haloalkyl, $C_1$-$C_6$ hydroxyalkyl, 3 to 6-membered cycloalkyl and 4 to 6-membered heterocycloalkyl;

each occurrence of $R^{12}$ is independently selected from $C_1$-$C_6$ alkyl, $C_1$-$C_6$ haloalkyl, 3 to 6-membered cycloalkyl, 4 to 6-membered heterocycloalkyl, aryl and 5 or 6-membered heteroaryl;

each occurrence of $R^{13}$ is independently selected from H, halo, $C_1$-$C_6$ alkyl, $C_1$-$C_6$ haloalkyl, 3 to 6-membered cycloalkyl, 4 to 6-membered heterocycloalkyl, —CN, —O$R^9$, —N($R^9$)$_2$, —C(O)$R^{12}$, —C(O)O$R^9$, —C(O)N($R^9$)$_2$, —NHC(O)$R^{12}$, —NHC(O)NH$R^9$, —NHC(O)O$R^9$, —OC(O)$R^{12}$, —S$R^9$ and —S(O)$_2R^{12}$, wherein two $R^{12}$ groups together with the carbon atom(s) to which they are attached, can optionally join to form a 3 to 6-membered cycloalkyl group or a 4 to 6-membered heterocycloalkyl group;

each occurrence of $R^{14}$ is independently selected from H, halo, $C_1$-$C_6$ alkyl, $C_1$-$C_6$ haloalkyl, —($C_1$-$C_6$ alkylene)-O—($C_1$-$C_6$ alkyl), 3 to 6-membered cycloalkyl, 4 to 6 membered heterocycloalkyl, aryl, 5 or 6-membered heteroaryl, CH$_2$-(5 or 6 membered heteroaryl) and benzyl, wherein said aryl group, said 5 or 6-membered heteroaryl group or the phenyl moiety of said benzyl group can be optionally substituted with up to 3 groups, which can be the same or different, and are selected from halo, —CN, $C_1$-$C_6$ alkyl, $C_1$-$C_6$ haloalkyl, —O—($C_1$-$C_6$ alkyl), —($C_1$-$C_6$ alkylene)-O—($C_1$-$C_6$ alkyl) and —O—($C_1$-$C_6$ haloalkyl);

each occurrence of $R^{15}$ is independently selected from H, $C_1$-$C_6$ alkyl, halo, —OH, —O—($C_1$-$C_6$ alkyl), $C_1$-$C_6$ haloalkyl and —O—($C_1$-$C_6$ haloalkyl);

each occurrence of $R^{16}$ is independently selected from H, halo, $C_1$-$C_6$ alkyl and 3 to 6-membered cycloalkyl, or two $R^{16}$ groups that are attached to a common silicon atom, join to form a —(CH$_2$)$_4$— or a —(CH$_2$)$_5$— group; and each occurrence of q is independently an integer ranging from 0 to 4.

In another aspect, the present invention provides Compounds of Formula (II):

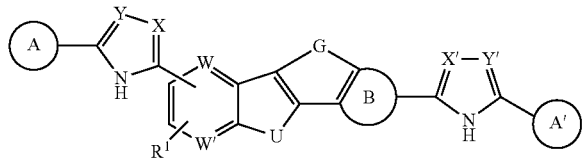

(II)

and pharmaceutically acceptable salts thereof, wherein:

A and A' are each independently selected from 5 or 6-membered monocyclic heterocycloalkyl, wherein said 5 or 6-membered monocyclic heterocycloalkyl group can be optionally fused to an aryl group; and wherein said 5 or 6-membered monocyclic heterocycloalkyl group can be optionally and independently substituted on one or more ring carbon atoms with $R^{13}$, such that any two $R^{13}$ groups on the same ring, together with the carbon atoms to which they are attached, can join to form a fused, bridged or spirocyclic 3 to 6-membered cycloalkyl group or a fused, bridged or spirocyclic 4 to 6-membered heterocycloalkyl group, wherein said 5 or 6-membered monocyclic heterocycloalkyl contains from 1 to 2 ring heteroatoms, each independently selected from $N(R^4)$, S, O and $Si(R^{16})_2$;

ring B is selected from phenyl or a 5 or 6-membered heteroaryl group, wherein said phenyl group and said 5 or 6-membered heteroaryl group can be optionally substituted on up to 2 ring carbon atoms with $R^{15}$;

G is selected from $-C(R^3)_2-$, $-N(R^5)-$, $-O-$, $-SO_2-$, $-C(R^3)_2-C(R^3)_2-O-$, $-C(R^3)_2-C(R^3)_2-N(R^5)-$, $-C(R^3)_2-C(O)-N(R^5)-$, $-C(O)-C(R^3)_2-C(R^3)_2-$, $-C(R^3)_2-C(R^3)-C(O)-$, $-C(R^3)_2-C(R^3)_2-C(R^3)_2-$, $-C(R^3)_2-C(R^3)_2-C(R^3)_2-O-$, $-C(R^3)_2-O-$, $-C(R^{14})=N-$, $-C(R^3)_2-C(R^3)_2-$ and $-C(R^{14})=C(R^{14})-$, such that when G is $-C(R^3)_2-O-$, $-C(R^{14})=N-$, $-C(R^3)_2-C(R^3)_2-$ or $-C(R^{14})=C(R^{14})-$, then B is a 5-membered heteroaryl group;

U is selected from $N(R^2)$, O and $SO_2$;

V and V' are each independently selected from N and $C(R^{15})$;

W and W' are each independently selected from N and $C(R^1)$;

X and X' are each independently selected from N and $C(R^{10})$;

Y and Y' are each independently selected from N and $C(R^{10})$;

$R^1$ is selected from H, $C_1$-$C_6$ alkyl, 3 to 6 membered cycloalkyl, halo, $-OH$, $-O-(C_1$-$C_6$ alkyl), $C_1$-$C_6$ haloalkyl and $-O-(C_1$-$C_6$ haloalkyl);

$R^2$ is selected from H, $C_1$-$C_6$ alkyl, 3 to 6-membered cycloalkyl, aryl, 5 or 6-membered heteroaryl and benzyl, wherein said aryl group, said 5 or 6-membered heteroaryl group or the phenyl moiety of said benzyl group can be optionally substituted with up to 3 groups, which can be the same or different, and are selected from $C_1$-$C_6$ alkyl, $C_1$-$C_6$ haloalkyl, $-O-(C_1$-$C_6$ alkyl), $-O-(C_1$-$C_6$ haloalkyl), halo, $-(C_1$-$C_6$ alkylene)-O-$(C_1$-$C_6$ alkyl) and $-CN$;

each occurrence of $R^3$ is independently selected from H, $C_1$-$C_6$ alkyl, $C_1$-$C_6$ haloalkyl, alkylene)-O-$(C_1$-$C_6$ alkyl), 3 to 6-membered cycloalkyl, 4 to 6-membered heterocycloalkyl, aryl, 5 or 6-membered heteroaryl, $-CH_2$-(5 or 6 membered heteroaryl) and benzyl, wherein said aryl group, said 5 or 6-membered heteroaryl group or the phenyl moiety of said benzyl group can be optionally substituted with up to 3 groups, which can be the same or different, and are selected from $C_1$-$C_6$ alkyl, $C_1$-$C_6$ haloalkyl, $-O-(C_1$-$C_6$ alkyl), $-O(C_1$-$C_6$ haloalkyl), halo, $-(C_1$-$C_6$ alkylene)-O-$(C_1$-$C_6$ alkyl) and $-CN$ and wherein two $R^3$ groups attached to the same carbon atom, together with the common carbon atom to which they are attached, can join to form a carbonyl group, a 3 to 6-membered spirocyclic cycloalkyl group or a 3 to 6-membered spirocyclic heterocycloalkyl group;

each occurrence of $R^4$ is independently selected from $-[C(R^7)_2]_qN(R^6)_2$, $-C(O)R^{11}$, $-C(O)-[C(R^7)_2]_qN(R^6)_2$, $-C(O)-[C(R^7)_2]_q-R^{11}$, $-C(O)-[C(R^7)_2]_qN(R^6)C(O)-R^{11}$, $-C(O)[C(R^7)_2]_qN(R^6)SO_2-R^{11}$, $-C(O)-[C(R^7)_2]_qN(R^6)C(O)O-R^{11}$, $-C(O)-[C(R^7)_2]_qC(O)O-R^{11}$ and -alkylene-$N(R^6)-[C(R^7)_2]_q-N(R^6)-C(O)O-R^{11}$;

each occurrence of $R^{15}$ is independently selected from H, $C_1$-$C_6$ alkyl, $-(C_1$-$C_6$ alkylene)-O-$(C_1$-$C_6$ alkyl), 3 to 6-membered cycloalkyl, 4 to 6-membered heterocycloalkyl, aryl, 5 or 6-membered heteroaryl and benzyl, wherein said aryl group, said 5 or 6-membered heteroaryl group or the phenyl moiety of said benzyl group can be optionally substituted with up to 3 groups, which can be the same or different, and are selected from $C_1$-$C_6$ alkyl, $C_1$-$C_6$ haloalkyl, $-O-(C_1$-$C_6$ alkyl), $-O-(C_1$-$C_6$ haloalkyl), halo, $-(C_1$-$C_6$ alkylene)-O-$(C_1$-$C_6$ alkyl) and $-CN$;

each occurrence of $R^6$ is independently selected from H, $C_1$-$C_6$ alkyl, 3 to 6-membered cycloalkyl, 4 to 6-membered heterocycloalkyl, aryl and 5 or 6-membered heteroaryl, wherein said 3 to 6-membered cycloalkyl group, said 4 to 6-membered heterocycloalkyl group, said aryl group and said 5 or 6-membered heteroaryl group can be optionally and independently substituted with up to two $R^8$ groups, and wherein two $R^6$ groups that are attached to the same nitrogen atom, together with the common nitrogen atom to which they are attached, can join to form a 4 to 6-membered heterocycloalkyl group;

each occurrence of $R^7$ is independently selected from H, $C_1$-$C_6$ alkyl, $C_1$-$C_6$ haloalkyl, -alkylene-O-$(C_1$-$C_6$ alkyl), 3 to 6-membered cycloalkyl, 4 to 6-membered heterocycloalkyl, aryl and 5 or 6-membered heteroaryl, wherein said 3 to 6-membered cycloalkyl group, said 4 to 6-membered heterocycloalkyl group, said aryl group and said 5 or 6-membered heteroaryl group can be optionally substituted with up to three $R^8$ groups;

each occurrence of $R^8$ is independently selected from H, $C_1$-$C_6$ alkyl, halo, $-C_1$-$C_6$ haloalkyl, $C_1$-$C_6$ hydroxyalkyl, $-OH$, $-C(O)NH-(C_1$-$C_6$ alkyl), $-C(O)N(C_1$-$C_6$ alkyl)$_2$, $-O-(C_1$-$C_6$ alkyl), $-NH_2$, $-NH(C_1$-$C_6$ alkyl), $-N(C_1$-$C_6$ alkyl)$_2$ and $-NHC(O)-(C_1$-$C_6$ alkyl);

each occurrence of $R^9$ is independently selected from H, $C_1$-$C_6$ alkyl, $C_1$-$C_6$ haloalkyl, 3 to 6-membered cycloalkyl, 4 to 6-membered heterocycloalkyl, aryl and 5 or 6-membered heteroaryl;

each occurrence of $R^{10}$ is independently selected from H, $C_1$-$C_6$ alkyl, $C_1$-$C_6$ haloalkyl, halo, $-OH$, $-O-(C_1$-$C_6$ alkyl) and $-CN$;

each occurrence of $R^{11}$ is independently selected from H, $C_1$-$C_6$ alkyl, $C_1$-$C_6$ haloalkyl, $C_1$-$C_6$ hydroxyalkyl, 3 to 6-membered cycloalkyl and 4 to 6-membered heterocycloalkyl;

each occurrence of $R^{12}$ is independently selected from $C_1$-$C_6$ alkyl, $C_1$-$C_6$ haloalkyl, 3 to 6-membered cycloalkyl, 4 to 6-membered heterocycloalkyl, aryl and 5 or 6-membered heteroaryl;

each occurrence of $R^{13}$ is independently selected from H, halo, $C_1$-$C_6$ alkyl, $C_1$-$C_6$ haloalkyl, 3 to 6-membered cycloalkyl, 4 to 6-membered heterocycloalkyl, $-CN$, $-OR^9$, $-N(R^9)_2$, $-C(O)R^{12}$, $-C(O)OR^9$, $-C(O)N(R^9)_2$, $-NHC(O)R^{12}$, $-NHC(O)NHR^9$, $-NHC(O)OR^9$, $-OC$ (O)$R^{12}$, —$SR^9$ and —S(O)$_2R^{12}$, wherein two $R^{13}$ groups together with the carbon atom(s) or silicon atom to which they are attached, can optionally join to form a 3 to 6-membered cycloalkyl group or a 4 to 6-membered heterocycloalkyl group;

each occurrence of $R^{14}$ is independently selected from H, halo, $C_1$-$C_6$ alkyl, $C_1$-$C_6$ haloalkyl, —($C_1$-$C_6$ alkylene)-O—($C_1$-$C_6$ alkyl), 3 to 6-membered cycloalkyl, 4 to 6 membered heterocycloalkyl, aryl, 5 or 6-membered heteroaryl, CH$_2$-(5 or 6 membered heteroaryl) and benzyl, wherein said aryl group, said 5 or 6-membered heteroaryl group or the phenyl moiety of said benzyl group can be optionally substituted with up to 3 groups, which can be the same or different, and are selected from halo, —CN, $C_1$-$C_6$ alkyl, $C_1$-$C_6$ haloalkyl, —O—($C_1$-$C_6$ alkyl), —($C_1$-$C_6$ alkylene)-O—($C_1$-$C_6$ alkyl) and —O—($C_1$-$C_6$ haloalkyl);

each occurrence of $R^{15}$ is independently selected from H, $C_1$-$C_6$ alkyl, 3 to 6-membered cycloalkyl, halo, —OH, —O—($C_1$-$C_6$ alkyl), $C_1$-$C_6$ haloalkyl and —O—($C_1$-$C_6$ haloalkyl);

each occurrence of $R^{16}$ is independently selected from H, halo, $C_1$-$C_6$ alkyl and 3 to 6-membered cycloalkyl; and each occurrence of q is independently an integer ranging from 0 to 4.

The Compounds of Formula (I) and (II) (also referred to herein collectively as the "Fused Tetracycle Derivatives") and pharmaceutically acceptable salts thereof can be useful, for example, for inhibiting HCV viral replication or replicon activity, and for treating or preventing HCV infection in a patient. Without being bound by any specific theory, it is believed that the Fused Tetracycle Derivatives inhibit HCV viral replication by inhibiting HCV NS5A.

Accordingly, the present invention provides methods for treating or preventing HCV infection in a patient, comprising administering to the patient an effective amount of at least one Fused Tetracycle Derivative.

The details of the invention are set forth in the accompanying detailed description below.

Although any methods and materials similar to those described herein can be used in the practice or testing of the present invention, illustrative methods and materials are now described. Other embodiments, aspects and features of the present invention are either further described in or will be apparent from the ensuing description, examples and appended claims.

DETAILED DESCRIPTION OF THE INVENTION

The present invention relates to novel Fused Tetracycle Derivatives, compositions comprising at least one Fused Tetracycle Derivative, and methods of using the Fused Tetracycle Derivatives for treating or preventing HCV infection in a patient.

DEFINITIONS AND ABBREVIATIONS

The terms used herein have their ordinary meaning and the meaning of such terms is independent at each occurrence thereof. That notwithstanding and except where stated otherwise, the following definitions apply throughout the specification and claims. Chemical names, common names, and chemical structures may be used interchangeably to describe the same structure. If a chemical compound is referred to using both a chemical structure and a chemical name and an ambiguity exists between the structure and the name, the structure predominates. These definitions apply regardless of whether a term is used by itself or in combination with other terms, unless otherwise indicated. Hence, the definition of "alkyl" applies to "alkyl" as well as the "alkyl" portions of "hydroxyalkyl," "haloalkyl," "—O-alkyl," etc. . . . . .

As used herein, and throughout this disclosure, the following terms, unless otherwise indicated, shall be understood to have the following meanings:

A "patient" is a human or non-human mammal. In one embodiment, a patient is a human. In another embodiment, a patient is a chimpanzee.

The term "effective amount" as used herein, refers to an amount of Fused Tetracycle Derivative and/or an additional therapeutic agent, or a composition thereof that is effective in producing the desired therapeutic, ameliorative, inhibitory or preventative effect when administered to a patient suffering from a viral infection or virus-related disorder. In the combination therapies of the present invention, an effective amount can refer to each individual agent or to the combination as a whole, wherein the amounts of all agents administered are together effective, but wherein the component agent of the combination may not be present individually in an effective amount.

The term "preventing," as used herein with respect to an HCV viral infection or HCV-virus related disorder, refers to reducing the likelihood of HCV infection.

The term "alkyl," as used herein, refers to an aliphatic hydrocarbon group having one of its hydrogen atoms replaced with a bond. An alkyl group may be straight or branched and contain from about 1 to about 20 carbon atoms. In one embodiment, an alkyl group contains from about 1 to about 12 carbon atoms. In different embodiments, an alkyl group contains from 1 to 6 carbon atoms ($C_1$-$C_6$ alkyl) or from about 1 to about 4 carbon atoms ($C_1$-$C_4$ alkyl). Non-limiting examples of alkyl groups include methyl, ethyl, n-propyl, isopropyl, n-butyl, sec-butyl, isobutyl, tert-butyl, n-pentyl, neopentyl, isopentyl, n-hexyl, isohexyl and neohexyl. An alkyl group may be unsubstituted or substituted by one or more substituents which may be the same or different, each substituent being independently selected from the group consisting of halo, alkenyl, alkynyl, aryl, cycloalkyl, cyano, hydroxy, —O-alkyl, —O-aryl, -alkylene-O-alkyl, alkylthio, —NH(alkyl), —N(alkyl)$_2$, —NH(cycloalkyl), —O—C(O)-alkyl, —O—C(O)-aryl, —O—C(O)-cycloalkyl, —C(O)OH and —C(O)O-alkyl. In one embodiment, an alkyl group is linear. In another embodiment, an alkyl group is branched. Unless otherwise indicated, an alkyl group is unsubstituted.

The term "alkenyl," as used herein, refers to an aliphatic hydrocarbon group containing at least one carbon-carbon double bond and having one of its hydrogen atoms replaced with a bond. An alkenyl group may be straight or branched and contain from about 2 to about 15 carbon atoms. In one embodiment, an alkenyl group contains from about 2 to about 12 carbon atoms. In another embodiment, an alkenyl group contains from about 2 to about 6 carbon atoms. Non-limiting examples of alkenyl groups include ethenyl, propenyl, n-butenyl, 3-methylbut-2-enyl, n-pentenyl, octenyl and decenyl. An alkenyl group may be unsubstituted or substituted by one or more substituents which may be the same or different, each substituent being independently selected from the group consisting of halo, alkenyl, alkynyl, aryl, cycloalkyl, cyano, hydroxy, —O-alkyl, —O-aryl, -alkylene-O-alkyl, alkylthio, —NH(alkyl), —N(alkyl)$_2$, —NH(cycloalkyl), —O—C(O)-alkyl, —O—C(O)-aryl, —O—C(O)-cycloalkyl, —C(O)OH and —C(O)O-alkyl. The term "$C_2$-$C_6$ alkenyl" refers to an alkenyl group having from 2 to 6 carbon atoms. Unless otherwise indicated, an alkenyl group is unsubstituted.

The term "alkynyl," as used herein, refers to an aliphatic hydrocarbon group containing at least one carbon-carbon triple bond and having one of its hydrogen atoms replaced with a bond. An alkynyl group may be straight or branched and contain from about 2 to about 15 carbon atoms. In one embodiment, an alkynyl group contains from about 2 to about 12 carbon atoms. In another embodiment, an alkynyl group contains from about 2 to about 6 carbon atoms. Non-limiting examples of alkynyl groups include ethynyl, propynyl, 2-butynyl and 3-methylbutynyl. An alkynyl group may be unsubstituted or substituted by one or more substituents which may be the same or different, each substituent being independently selected from the group consisting of halo, alkenyl, alkynyl, aryl, cycloalkyl, cyano, hydroxy, —O-alkyl, —O-aryl, -alkylene-O-alkyl, alkylthio, —NH$_2$, —NH(alkyl), —N(alkyl)$_2$, —NH(cycloalkyl), —O—C(O)-alkyl, —O—C(O)-aryl, —O—C(O)-cycloalkyl, —C(O)OH and —C(O)O-alkyl. The term "C$_2$-C$_6$ alkynyl" refers to an alkynyl group having from 2 to 6 carbon atoms. Unless otherwise indicated, an alkynyl group is unsubstituted.

The term "alkylene," as used herein, refers to an alkyl group, as defined above, wherein one of the alkyl group's hydrogen atoms has been replaced with a bond. Non-limiting examples of alkylene groups include —CH$_2$—, —CH$_2$CH$_2$—, —CH$_2$CH$_2$CH$_2$—, CH$_2$CH$_2$CH$_2$CH$_2$—, —CH(CH$_3$)CH$_2$CH$_2$—, —CH(CH$_3$)— and —CH$_2$CH(CH$_3$) CH$_2$—. In one embodiment, an alkylene group has from 1 to about 6 carbon atoms. In another embodiment, an alkylene group is branched. In another embodiment, an alkylene group is linear. In one embodiment, an alkylene group is —CH$_2$—. The term "C$_1$-C$_6$ alkylene" refers to an alkylene group having from 1 to 6 carbon atoms.

The term "aryl," as used herein, refers to an aromatic monocyclic or multicyclic ring system comprising from about 6 to about 14 carbon atoms. In one embodiment, an aryl group contains from about 6 to about 10 carbon atoms. An aryl group can be optionally substituted with one or more "ring system substituents" which may be the same or different, and are as defined herein below. In one embodiment, an aryl group can be optionally fused to a cycloalkyl or cycloalkanoyl group. Non-limiting examples of aryl groups include phenyl and naphthyl. In one embodiment, an aryl group is phenyl. Unless otherwise indicated, an aryl group is unsubstituted.

The term "arylene," as used herein, refers to a bivalent group derived from an aryl group, as defined above, by removal of a hydrogen atom from a ring carbon of an aryl group. An arylene group can be derived from a monocyclic or multicyclic ring system comprising from about 6 to about 14 carbon atoms. In one embodiment, an arylene group contains from about 6 to about 10 carbon atoms. In another embodiment, an arylene group is a naphthylene group. In another embodiment, an arylene group is a phenylene group. An arylene group can be optionally substituted with one or more "ring system substituents" which may be the same or different, and are as defined herein below. An arylene group is divalent and either available bond on an arylene group can connect to either group flanking the arylene group. For example, the group "A-arylene-B," wherein the arylene group is:

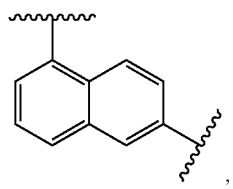 [SMILES: *c1ccc2c(*)cccc2c1]

is understood to represent both:

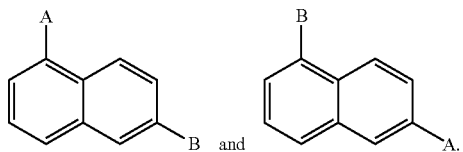

In one embodiment, an arylene group can be optionally fused to a cycloalkyl or cycloalkanoyl group. Non-limiting examples of arylene groups include phenylene and naphthalene. In one embodiment, an arylene group is unsubstituted. In another embodiment, an arylene group is:

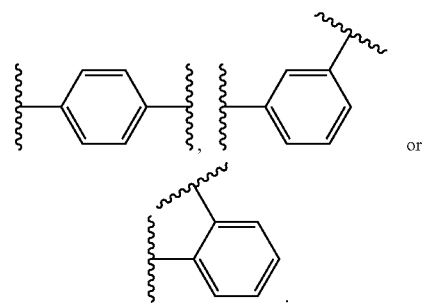

Unless otherwise indicated, an arylene group is unsubstituted.

The term "cycloalkyl," as used herein, refers to a non-aromatic mono- or multicyclic ring system comprising from about 3 to about 10 ring carbon atoms. In one embodiment, a cycloalkyl contains from about 5 to about 10 ring carbon atoms. In another embodiment, a cycloalkyl contains from about 3 to about 7 ring atoms. In another embodiment, a cycloalkyl contains from about 5 to about 6 ring atoms. The term "cycloalkyl" also encompasses a cycloalkyl group, as defined above, which is fused to an aryl (e.g., benzene) or heteroaryl ring. Non-limiting examples of monocyclic cycloalkyls include cyclopropyl, cyclobutyl, cyclopentyl, cyclohexyl, cycloheptyl and cyclooctyl. Non-limiting examples of multicyclic cycloalkyls include 1-decalinyl, norbornyl and adamantyl. A cycloalkyl group can be optionally substituted with one or more "ring system substituents" which may be the same or different, and are as defined herein below. In one embodiment, a cycloalkyl group is unsubstituted. The term "3 to 6-membered cycloalkyl" refers to a cycloalkyl group having from 3 to 6 ring carbon atoms. Unless otherwise indicated, a cycloalkyl group is unsubstituted. A ring carbon atom of a cycloalkyl group may be functionalized as a carbonyl group. An illustrative example of such a cycloalkyl group (also referred to herein as a "cycloalkanoyl" group) includes, but is not limited to, cyclobutanoyl:

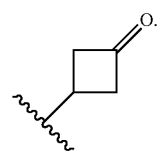

The term "cycloalkenyl," as used herein, refers to a non-aromatic mono- or multicyclic ring system comprising from about 4 to about 10 ring carbon atoms and containing at least one endocyclic double bond. In one embodiment, a cycloalkenyl contains from about 4 to about 7 ring carbon atoms. In another embodiment, a cycloalkenyl contains 5 or 6 ring atoms. Non-limiting examples of monocyclic cycloalkenyls include cyclopentenyl, cyclohexenyl, cyclohepta-1,3-dienyl, and the like. A cycloalkenyl group can be optionally substituted with one or more "ring system substituents" which may be the same or different, and are as defined herein below. A ring carbon atom of a cycloalkyl group may be functionalized as a carbonyl group. In one embodiment, a cycloalkenyl group is cyclopentenyl. In another embodiment, a cycloalkenyl group is cyclohexenyl. The term "4 to 6-membered cycloalkenyl" refers to a cycloalkenyl group having from 4 to 6 ring carbon atoms. Unless otherwise indicated, a cycloalkenyl group is unsubstituted.

The term "halo," as used herein, means —F, —Cl, —Br or —I.

The term "haloalkyl," as used herein, refers to an alkyl group as defined above, wherein one or more of the alkyl group's hydrogen atoms has been replaced with a halogen. In one embodiment, a haloalkyl group has from 1 to 6 carbon atoms. In another embodiment, a haloalkyl group is substituted with from 1 to 3 F atoms. Non-limiting examples of haloalkyl groups include —CH$_2$F, —CHF$_2$, —CF$_3$, —CH$_2$Cl and —CCl$_3$. The term "C$_1$-C$_6$ haloalkyl" refers to a haloalkyl group having from 1 to 6 carbon atoms.

The term "hydroxyalkyl," as used herein, refers to an alkyl group as defined above, wherein one or more of the alkyl group's hydrogen atoms has been replaced with an —OH group. In one embodiment, a hydroxyalkyl group has from 1 to 6 carbon atoms. Non-limiting examples of hydroxyalkyl groups include —CH$_2$OH, —CH$_2$CH$_2$OH, —CH$_2$CH$_2$CH$_2$OH and —CH$_2$CH(OH)CH$_3$. The term "C$_1$-C$_6$ hydroxyalkyl" refers to a hydroxyalkyl group having from 1 to 6 carbon atoms.

The term "heteroaryl," as used herein, refers to an aromatic monocyclic or multicyclic ring system comprising about 5 to about 14 ring atoms, wherein from 1 to 4 of the ring atoms is independently O, N or S and the remaining ring atoms are carbon atoms. In one embodiment, a heteroaryl group has 5 to 10 ring atoms. In another embodiment, a heteroaryl group is monocyclic and has 5 or 6 ring atoms. In another embodiment, a heteroaryl group is bicyclic. A heteroaryl group can be optionally substituted by one or more "ring system substituents" which may be the same or different, and are as defined herein below. A heteroaryl group is joined via a ring carbon atom, and any nitrogen atom of a heteroaryl can be optionally oxidized to the corresponding N-oxide. The term "heteroaryl" also encompasses a heteroaryl group, as defined above, which is fused to a benzene ring. Non-limiting examples of heteroaryls include pyridyl, pyrazinyl, furanyl, thienyl, pyrimidinyl, pyridone (including N-substituted pyridones), isoxazolyl, isothiazolyl, oxazolyl, oxadiazolyl, thiazolyl, pyrazolyl, furazanyl, pyrrolyl, triazolyl, 1,2,4-thiadiazolyl, pyrazinyl, pyridazinyl, quinoxalinyl, phthalazinyl, oxindolyl, imidazo[1,2-a]pyridinyl, imidazo[2,1-b]thiazolyl, benzofurazanyl, indolyl, azaindolyl, benzimidazolyl, benzothienyl, quinolinyl, imidazolyl, benzimidazolyl, thienopyridyl, quinazolinyl, thienopyrimidyl, pyrrolopyridyl, imidazopyridyl, isoquinolinyl, benzoazaindolyl, 1,2,4-triazinyl, benzothiazolyl and the like, and all isomeric forms thereof. The term "heteroaryl" also refers to partially saturated heteroaryl moieties such as, for example, tetrahydroisoquinolyl, tetrahydroquinolyl and the like. In one embodiment, a heteroaryl group is a 5-membered heteroaryl. In another embodiment, a heteroaryl group is a 6-membered heteroaryl. In another embodiment, a heteroaryl group comprises a 5- to 6-membered heteroaryl group fused to a benzene ring. Unless otherwise indicated, a heteroaryl group is unsubstituted.

The term "heteroarylene," as used herein, refers to a bivalent group derived from an heteroaryl group, as defined above, by removal of a hydrogen atom from a ring carbon or ring heteroatom of a heteroaryl group. A heteroarylene group can be derived from a monocyclic or multicyclic ring system comprising about 5 to about 14 ring atoms, wherein from 1 to 4 of the ring atoms are each independently O, N or S and the remaining ring atoms are carbon atoms. A heteroarylene group can be optionally substituted by one or more "ring system substituents" which may be the same or different, and are as defined herein below. A heteroarylene group is joined via a ring carbon atom or by a nitrogen atom with an open valence, and any nitrogen atom of a heteroarylene can be optionally oxidized to the corresponding N-oxide. The term "heteroarylene" also encompasses a heteroarylene group, as defined above, which is fused to a benzene ring. Non-limiting examples of heteroarylenes include pyridylene, pyrazinylene, furanylene, thienylene, pyrimidinylene, pyridonylene (including those derived from N-substituted pyridonyls), isoxazolylene, isothiazolylene, oxazolylene, oxadiazolylene, thiazolylene, pyrazolylene, thiophenylene, furazanylene, pyrrolylene, triazolylene, 1,2,4-thiadiazolylene, pyrazinylene, pyridazinylene, quinoxalinylene, phthalazinylene, oxindolylene, imidazo[1,2-a]pyridinylene, imidazo[2,1-b]thiazolylene, benzofurazanylene, indolylene, azaindolylene, benzimidazolylene, benzothienylene, quinolinylene, imidazolylene, benzimidazolylene, thienopyridylene, quinazolinylene, thienopyrimidylene, pyrrolopyridylene, imidazopyridylene, isoquinolinylene, benzoazaindolylene, 1,2,4-triazinylene, benzothiazolylene and the like, and all isomeric forms thereof. The term "heteroarylene" also refers to partially saturated heteroarylene moieties such as, for example, tetrahydroisoquinolylene, tetrahydroquinolylene, and the like. A heteroarylene group is divalent and either available bond on a heteroarylene ring can connect to either group flanking the heteroarylene group. For example, the group "A-heteroarylene-B," wherein the heteroarylene group is:

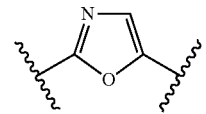 [SMILES: *c1cnc(*)o1]

is understood to represent both:

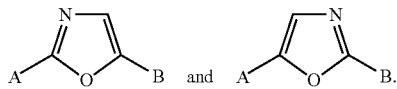

In one embodiment, a heteroarylene group is a monocyclic heteroarylene group or a bicyclic heteroarylene group. In another embodiment, a heteroarylene group is a monocyclic heteroarylene group. In another embodiment, a heteroarylene group is a bicyclic heteroarylene group. In still another embodiment, a heteroarylene group has from about 5 to about 10 ring atoms. In another embodiment, a heteroarylene group is monocyclic and has 5 or 6 ring atoms. In another embodiment, a heteroarylene group is bicyclic and has 9 or 10 ring atoms. In another embodiment, a heteroarylene group is a 5-membered monocyclic heteroarylene. In another embodiment, a heteroarylene group is a 6-membered monocyclic heteroarylene. In another embodiment, a bicyclic heteroarylene group comprises a 5 or 6-membered monocyclic heteroarylene group fused to a benzene ring. Unless otherwise indicated, a heteroarylene group is unsubstituted.

The term "heterocycloalkyl," as used herein, refers to a non-aromatic saturated monocyclic or multicyclic ring system comprising 3 to about 11 ring atoms, wherein from 1 to 4 of the ring atoms are independently O, S, N or Si, and the remainder of the ring atoms are carbon atoms. A heterocycloalkyl group can be joined via a ring carbon, ring silicon atom or ring nitrogen atom. In one embodiment, a heterocycloalkyl group is monocyclic and has from about 3 to about 7 ring atoms. In another embodiment, a heterocycloalkyl group is monocyclic has from about 4 to about 7 ring atoms. In another embodiment, a heterocycloalkyl group is bicyclic and has from about 7 to about 11 ring atoms. In still another embodiment, a heterocycloalkyl group is monocyclic and has 5 or 6 ring atoms. In one embodiment, a heterocycloalkyl group is monocyclic. In another embodiment, a heterocycloalkyl group is bicyclic. There are no adjacent oxygen and/or sulfur atoms present in the ring system. Any —NH group in a heterocycloalkyl ring may exist protected such as, for example, as an —N(BOC), —N(Cbz), —N(Tos) group and the like; such protected heterocycloalkyl groups are considered part of this invention. The term "heterocycloalkyl" also encompasses a heterocycloalkyl group, as defined above, which is fused to an aryl (e.g., benzene) or heteroaryl ring. A heterocycloalkyl group can be optionally substituted by one or more "ring system substituents" which may be the same or different, and are as defined herein below. The nitrogen or sulfur atom of the heterocycloalkyl can be optionally oxidized to the corresponding N-oxide, S-oxide or S,S-dioxide. Non-limiting examples of monocyclic heterocycloalkyl rings include oxetanyl, piperidyl, pyrrolidinyl, piperazinyl, morpholinyl, thiomorpholinyl, thiazolidinyl, 1,4-dioxanyl, tetrahydrofuranyl, tetrahydrothiophenyl, delta-lactam, delta-lactone, silacyclopentane, silapyrrolidine and the like, and all isomers thereof. Non-limiting illustrative examples of a silyl-containing heterocycloalkyl group include:

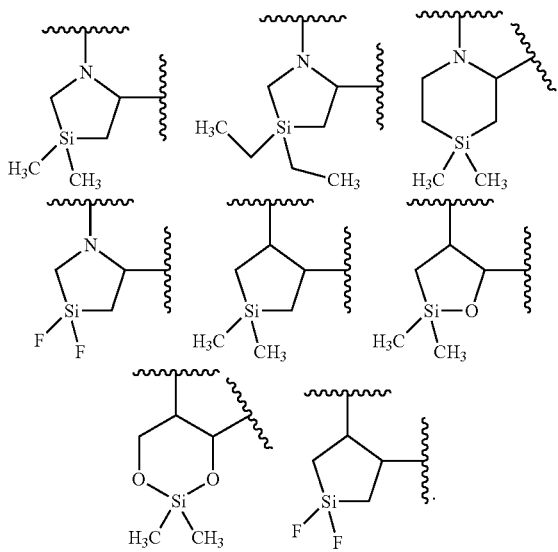

A ring carbon atom of a heterocycloalkyl group may be functionalized as a carbonyl group. An illustrative example of such a heterocycloalkyl group is:

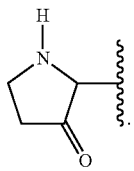 [SMILES: *C1NCCC1=O]

In one embodiment, a heterocycloalkyl group is a 5-membered monocyclic heterocycloalkyl. In another embodiment, a heterocycloalkyl group is a 6-membered monocyclic heterocycloalkyl. The term "3 to 6-membered monocyclic cycloalkyl" refers to a monocyclic heterocycloalkyl group having from 3 to 6 ring atoms. The term "4 to 6-membered monocyclic cycloalkyl" refers to a monocyclic heterocycloalkyl group having from 4 to 6 ring atoms. The term "7 to 11-membered bicyclic heterocycloalkyl" refers to a bicyclic heterocycloalkyl group having from 7 to 11 ring atoms. Unless otherwise indicated, an heterocycloalkyl group is unsubstituted.

The term "heterocycloalkenyl," as used herein, refers to a heterocycloalkyl group, as defined above, wherein the heterocycloalkyl group contains from 4 to 10 ring atoms, and at least one endocyclic carbon-carbon or carbon-nitrogen double bond. A heterocycloalkenyl group can be joined via a ring carbon or ring nitrogen atom. In one embodiment, a heterocycloalkenyl group has from 4 to 6 ring atoms. In another embodiment, a heterocycloalkenyl group is monocyclic and has 5 or 6 ring atoms. In another embodiment, a heterocycloalkenyl group is bicyclic. A heterocycloalkenyl group can optionally substituted by one or more ring system substituents, wherein "ring system substituent" is as defined above. The nitrogen or sulfur atom of the heterocycloalkenyl can be optionally oxidized to the corresponding N-oxide, S-oxide or S,S-dioxide. Non-limiting examples of heterocycloalkenyl groups include 1,2,3,4-tetrahydropyridinyl, 1,2-dihydropyridinyl, 1,4-dihydropyridinyl, 1,2,3,6-tetrahydropyridinyl, 1,4,5,6-tetrahydropyrimidinyl, 2-pyrrolinyl, 3-pyrrolinyl, 2-imidazolinyl, 2-pyrazolinyl, dihydroimidazolyl, dihydrooxazolyl, dihydrooxadiazolyl, dihydrothiazolyl, 3,4-dihydro-2H-pyranyl, dihydrofuranyl, fluoro-substituted dihydrofuranyl, 7-oxabicyclo[2.2.1]heptenyl, dihydrothiophenyl, dihydrothiopyranyl, and the like and the like. A ring carbon atom of a heterocycloalkenyl group may be functionalized as a carbonyl group. In one embodiment, a heterocycloalkenyl group is a 5-membered heterocycloalkenyl. In another embodiment, a heterocycloalkenyl group is a 6-membered heterocycloalkenyl. The term "4 to 6-membered heterocycloalkenyl" refers to a heterocycloalkenyl group having from 4 to 6 ring atoms. Unless otherwise indicated, a heterocycloalkenyl group is unsubstituted.

The term "ring system substituent," as used herein, refers to a substituent group attached to an aromatic or non-aromatic ring system which, for example, replaces an available hydrogen on the ring system. Ring system substituents may be the same or different, each being independently selected from the group consisting of alkyl, alkenyl, alkynyl, aryl, heteroaryl, -alkylene-aryl, -arylene-alkyl, -alkylene-heteroaryl, -alkenylene-heteroaryl, -alkynylene-heteroaryl, —OH, hydroxyalkyl, haloalkyl, —O-alkyl, —O-haloalkyl, -alkylene-O-alkyl, —O-aryl, —O-alkylene-aryl, acyl, —C(O)-aryl, halo, —NO$_2$, —CN, —SF$_5$, —C(O)OH, —C(O)O-alkyl, —C(O)O-aryl, —C(O)O-alkylene-aryl, —S(O)-alkyl, —S(O)$_2$-alkyl, —S(O)-aryl, —S(O)$_2$-aryl, —S(O)-heteroaryl, —S(O)$_2$-heteroaryl, —S-alkyl, —S-aryl, —S-heteroaryl, S-alkylene-aryl, —S-alkylene-heteroaryl, —S(O)$_2$-alkylenearyl, —S(O)₂-alkylene-heteroaryl, —Si(alkyl)₂, —Si(aryl)₂, —Si(heteroaryl)₂, —Si(alkyl)(aryl), —Si(alkyl)(cycloalkyl), —Si(alkyl)(heteroaryl), cycloalkyl, heterocycloalkyl, —O—C(O)-alkyl, —O—C(O)-aryl, —O—C(O)-cycloalkyl, —C(=N—CN)—NH₂, —C(=NH)—NH₂, —C(=NH)—NH(alkyl), —N(Y₁)(Y₂), -alkylene-N(Y₁)(Y₂), —C(O)N(Y₁)(Y₂) and —S(O)₂N(Y₁)(Y₂), wherein Y₁ and Y₂ can be the same or different and are independently selected from the group consisting of hydrogen, alkyl, aryl, cycloalkyl, and -alkylene-aryl. "Ring system substituent" may also mean a single moiety which simultaneously replaces two available hydrogens on two adjacent carbon atoms (one H on each carbon) on a ring system. Examples of such moiety are methylenedioxy, ethylenedioxy, —C(CH₃)₂— and the like which form moieties such as, for example:

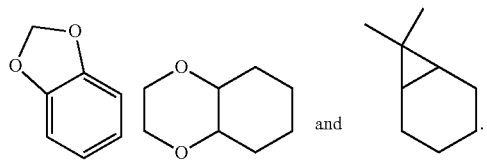

The term "silylalkyl," as used herein, refers to an alkyl group as defined above, wherein one or more of the alkyl group's hydrogen atoms has been replaced with a —Si(R$^x$)₃ group, wherein each occurrence of R$^x$ is independently C₁-C₆ alkyl, phenyl or a 3 to 6-membered cycloalkyl group. In one embodiment, a silylalkyl group has from 1 to 6 carbon atoms. In another embodiment, a silyl alkyl group contains a —Si(CH₃)₃ moiety. Non-limiting examples of silylalkyl groups include —CH₂—Si(CH₃)₃ and —CH₂CH₂—Si(CH₃)₃.

The term "substituted" means that one or more hydrogens on the designated atom is replaced with a selection from the indicated group, provided that the designated atom's normal valency under the existing circumstances is not exceeded, and that the substitution results in a stable compound. Combinations of substituents and/or variables are permissible only if such combinations result in stable compounds. By "stable compound' or "stable structure" is meant a compound that is sufficiently robust to survive isolation to a useful degree of purity from a reaction mixture, and formulation into an efficacious therapeutic agent.

The term "in substantially purified form," as used herein, refers to the physical state of a compound after the compound is isolated from a synthetic process (e.g., from a reaction mixture), a natural source, or a combination thereof. The term "in substantially purified form," also refers to the physical state of a compound after the compound is obtained from a purification process or processes described herein or well-known to the skilled artisan (e.g., chromatography, recrystallization and the like), in sufficient purity to be characterizable by standard analytical techniques described herein or well-known to the skilled artisan.

It should also be noted that any carbon as well as heteroatom with unsatisfied valences in the text, schemes, examples and tables herein is assumed to have the sufficient number of hydrogen atom(s) to satisfy the valences.

When a functional group in a compound is termed "protected", this means that the group is in modified form to preclude undesired side reactions at the protected site when the compound is subjected to a reaction. Suitable protecting groups will be recognized by those with ordinary skill in the art as well as by reference to standard textbooks such as, for example, T. W. Greene et al, *Protective Groups in Organic Synthesis* (1991), Wiley, New York.

When any substituent or variable (e.g., alkyl, R⁶, R$^a$, etc.) occurs more than one time in any constituent or in Formula (I), its definition on each occurrence is independent of its definition at every other occurrence, unless otherwise indicated.

As used herein, the term "composition" is intended to encompass a product comprising the specified ingredients in the specified amounts, as well as any product which results, directly or indirectly, from combination of the specified ingredients in the specified amounts.

Prodrugs and solvates of the compounds of the invention are also contemplated herein. A discussion of prodrugs is provided in T. Higuchi and V. Stella, *Prodrugs as Novel Delivery Systems* (1987) 14 of the A.C.S. Symposium Series, and in *Bioreversible Carriers in Drug Design*, (1987) Edward B. Roche, ed., American Pharmaceutical Association and Pergamon Press. The term "prodrug" means a compound (e.g., a drug precursor) that is transformed in vivo to provide a Fused Tetracycle Derivative or a pharmaceutically acceptable salt or solvate of the compound. The transformation may occur by various mechanisms (e.g., by metabolic or chemical processes), such as, for example, through hydrolysis in blood.

For example, if a Fused Tetracycle Derivative or a pharmaceutically acceptable salt, hydrate or solvate of the compound contains a carboxylic acid functional group, a prodrug can comprise an ester formed by the replacement of the hydrogen atom of the acid group with a group such as, for example, (C₁-C₈)alkyl, (C₂-C₁₂)alkanoyloxymethyl, 1-(alkanoyloxy)ethyl having from 4 to 9 carbon atoms, 1-methyl-1-(alkanoyloxy)-ethyl having from 5 to 10 carbon atoms, alkoxycarbonyloxymethyl having from 3 to 6 carbon atoms, 1-(alkoxycarbonyloxy)ethyl having from 4 to 7 carbon atoms, 1-methyl-1-(alkoxycarbonyloxy)ethyl having from 5 to 8 carbon atoms, N-(alkoxycarbonyl)aminomethyl having from 3 to 9 carbon atoms, 1-(N-(alkoxycarbonyl)amino)ethyl having from 4 to 10 carbon atoms, 3-phthalidyl, 4-crotonolactonyl, gamma-butyrolacton-4-yl, di-N,N—(C₁-C₂)alkylamino(C₂-C₃)alkyl (such as β-dimethylaminoethyl), carbamoyl-(C₁-C₂)alkyl, N,N-di (C₁-C₂)alkylcarbamoyl-(C₁-C₂)alkyl and piperidino-, pyrrolidino- or morpholino(C₂-C₃) alkyl, and the like.

Similarly, if a Fused Tetracycle Derivative contains an alcohol functional group, a prodrug can be formed by the replacement of the hydrogen atom of the alcohol group with a group such as, for example, (C₁-C₆)alkanoyloxymethyl, 1-((C₁-C₆)alkanoyloxy)ethyl, 1-methyl-1-((C₁-C₆)alkanoyloxy)ethyl, (C₁-C₆)alkoxycarbonyloxymethyl, N—(C₁-C₆) alkoxycarbonylaminomethyl, succinoyl, (C₁-C₆)alkanoyl, α-amino(C₁-C₄)alkyl, α-amino(C₁-C₄)alkylene-aryl, arylacyl and α-aminoacyl, or α-aminoacyl-α-aminoacyl, where each α-aminoacyl group is independently selected from the naturally occurring L-amino acids, —P(O)(OH)₂, —P(O)(O (C₁-C₆)alkyl)₂ or glycosyl (the radical resulting from the removal of a hydroxyl group of the hemiacetal form of a carbohydrate), and the like.

If a Fused Tetracycle Derivative incorporates an amine functional group, a prodrug can be formed by the replacement of a hydrogen atom in the amine group with a group such as, for example, R-carbonyl-, RO-carbonyl-, NRR'-carbonyl-wherein R and R' are each independently (C₁-C₁₀)alkyl, (C₃-C₇)cycloalkyl, benzyl, a natural α-aminoacyl, —C(OH)C(O) OY¹ wherein Y¹ is H, (C₁-C₆)alkyl or benzyl, —C(OY²)Y³ wherein Y² is (C₁-C₄)alkyl and Y³ is (C₁-C₆)alkyl; carboxy (C₁-C₆)alkyl; amino(C₁-C₄)alkyl or mono-N— or di-N,N—(C₁-C₆)alkylaminoalkyl; —C(Y⁴)Y⁵ wherein Y⁴ is H or methyl and $Y^5$ is mono-N— or di-N,N—$(C_1$-$C_6)$alkylamino morpholino; piperidin-1-yl or pyrrolidin-1-yl, and the like.

Pharmaceutically acceptable esters of the present compounds include the following groups: (1) carboxylic acid esters obtained by esterification of the hydroxy group of a hydroxyl compound, in which the non-carbonyl moiety of the carboxylic acid portion of the ester grouping is selected from straight or branched chain alkyl (e.g., methyl, ethyl, n-propyl, isopropyl, t-butyl, sec-butyl or n-butyl), alkoxyalkyl (e.g., methoxymethyl), aralkyl (e.g., benzyl), aryloxyalkyl (for example, phenoxymethyl), aryl (e.g., phenyl optionally substituted with, for example, halogen, $C_{1-4}$alkyl, —O—$(C_{1-4}$ alkyl) or amino); (2) sulfonate esters, such as alkyl- or aralkylsulfonyl (for example, methanesulfonyl); (3) amino acid esters (e.g., L-valyl or L-isoleucyl); (4) phosphonate esters and (5) mono-, di- or triphosphate esters. The phosphate esters may be further esterified by, for example, a $C_{1-20}$ alcohol or reactive derivative thereof, or by a 2,3-di $(C_{6-24})$ acyl glycerol.

One or more compounds of the invention may exist in unsolvated as well as solvated forms with pharmaceutically acceptable solvents such as water, ethanol, and the like, and it is intended that the invention embrace both solvated and unsolvated forms. "Solvate" means a physical association of a compound of this invention with one or more solvent molecules. This physical association involves varying degrees of ionic and covalent bonding, including hydrogen bonding. In certain instances the solvate will be capable of isolation, for example when one or more solvent molecules are incorporated in the crystal lattice of the crystalline solid. "Solvate" encompasses both solution-phase and isolatable solvates. Non-limiting examples of solvates include ethanolates, methanolates, and the like. A "hydrate" is a solvate wherein the solvent molecule is water.

One or more compounds of the invention may optionally be converted to a solvate. Preparation of solvates is generally known. Thus, for example, M. Caira et al, *J. Pharmaceutical Sci.*, 93(3), 601-611 (2004) describe the preparation of the solvates of the antifungal fluconazole in ethyl acetate as well as from water. Similar preparations of solvates, hemisolvate, hydrates and the like are described by E. C. van Tonder et al, *AAPS Pharm Sci Techours.*, 5(1), article 12 (2004); and A. L. Bingham et al, *Chem. Commun.*, 603-604 (2001). A typical, non-limiting, process involves dissolving the inventive compound in desired amounts of the desired solvent (organic or water or mixtures thereof) at a higher than room temperature, and cooling the solution at a rate sufficient to form crystals which are then isolated by standard methods. Analytical techniques such as, for example IR spectroscopy, show the presence of the solvent (or water) in the crystals as a solvate (or hydrate).

The Fused Tetracycle Derivatives can form salts which are also within the scope of this invention. Reference to a Fused Tetracycle Derivative herein is understood to include reference to salts thereof, unless otherwise indicated. The term "salt(s)", as employed herein, denotes acidic salts formed with inorganic and/or organic acids, as well as basic salts formed with inorganic and/or organic bases. In addition, when a Fused Tetracycle Derivative contains both a basic moiety, such as, but not limited to a pyridine or imidazole, and an acidic moiety, such as, but not limited to a carboxylic acid, zwitterions ("inner salts") may be formed and are included within the term "salt(s)" as used herein. In one embodiment, the salt is a pharmaceutically acceptable (i.e., non-toxic, physiologically acceptable) salt. In another embodiment, the salt is other than a pharmaceutically acceptable salt. Salts of the Compounds of Formula (I) or (II) may be formed, for example, by reacting a Fused Tetracycle Derivative with an amount of acid or base, such as an equivalent amount, in a medium such as one in which the salt precipitates or in an aqueous medium followed by lyophilization.

Exemplary acid addition salts include acetates, ascorbates, benzoates, benzenesulfonates, bisulfates, borates, butyrates, citrates, camphorates, camphorsulfonates, fumarates, hydrochlorides, hydrobromides, hydroiodides, lactates, maleates, methanesulfonates, naphthalenesulfonates, nitrates, oxalates, phosphates, propionates, salicylates, succinates, sulfates, tartarates, thiocyanates, toluenesulfonates (also known as tosylates) and the like. Additionally, acids which are generally considered suitable for the formation of pharmaceutically useful salts from basic pharmaceutical compounds are discussed, for example, by P. Stahl et al, Camille G. (eds.) *Handbook of Pharmaceutical Salts. Properties, Selection and Use*. (2002) Zurich: Wiley-VCH; S. Berge et al, *Journal of Pharmaceutical Sciences* (1977) 66(1) 1-19; P. Gould, *International J. of Pharmaceutics* (1986) 33 201-217; Anderson et al, *The Practice of Medicinal Chemistry* (1996), Academic Press, New York; and in *The Orange Book* (Food & Drug Administration, Washington, D.C. on their website). These disclosures are incorporated herein by reference thereto.

Exemplary basic salts include ammonium salts, alkali metal salts such as sodium, lithium, and potassium salts, alkaline earth metal salts such as calcium and magnesium salts, salts with organic bases (for example, organic amines) such as dicyclohexylamine, t-butyl amine, choline, and salts with amino acids such as arginine, lysine and the like. Basic nitrogen-containing groups may be quarternized with agents such as lower alkyl halides (e.g., methyl, ethyl, and butyl chlorides, bromides and iodides), dialkyl sulfates (e.g., dimethyl, diethyl, and dibutyl sulfates), long chain halides (e.g., decyl, lauryl, and stearyl chlorides, bromides and iodides), aralkyl halides (e.g., benzyl and phenethyl bromides), and others.

All such acid salts and base salts are intended to be pharmaceutically acceptable salts within the scope of the invention and all acid and base salts are considered equivalent to the free forms of the corresponding compounds for purposes of the invention.

Diastereomeric mixtures can be separated into their individual diastereomers on the basis of their physical chemical differences by methods well-known to those skilled in the art, such as, for example, by chromatography and/or fractional crystallization. Enantiomers can be separated by converting the enantiomeric mixture into a diastereomeric mixture by reaction with an appropriate optically active compound (e.g., chiral auxiliary such as a chiral alcohol or Mosher's acid chloride), separating the diastereomers and converting (e.g., hydrolyzing) the individual diastereomers to the corresponding pure enantiomers. Sterochemically pure compounds may also be prepared by using chiral starting materials or by employing salt resolution techniques. Also, some of the Fused Tetracycle Derivatives may be atropisomers (e.g., substituted biaryls) and are considered as part of this invention. Enantiomers can also be directly separated using chiral chromatographic techniques.

It is also possible that the Fused Tetracycle Derivatives may exist in different tautomeric forms, and all such forms are embraced within the scope of the invention. For example, all keto-enol and imine-enamine forms of the compounds are included in the invention.

All stereoisomers (for example, geometric isomers, optical isomers and the like) of the present compounds (including those of the salts, solvates, hydrates, esters and prodrugs of the compounds as well as the salts, solvates and esters of the prodrugs), such as those which may exist due to asymmetric carbons on various substituents, including enantiomeric forms (which may exist even in the absence of asymmetric carbons), rotameric forms, atropisomers, and diastereomeric forms, are contemplated within the scope of this invention. If a Fused Tetracycle Derivative incorporates a double bond or a fused ring, both the cis- and trans-forms, as well as mixtures, are embraced within the scope of the invention.

Individual stereoisomers of the compounds of the invention may, for example, be substantially free of other isomers, or may be admixed, for example, as racemates or with all other, or other selected, stereoisomers. The chiral centers of the present invention can have the S or R configuration as defined by the IUPAC 1974 Recommendations. The use of the terms "salt", "solvate", "ester", "prodrug" and the like, is intended to apply equally to the salt, solvate, ester and prodrug of enantiomers, stereoisomers, rotamers, tautomers, positional isomers, racemates or prodrugs of the inventive compounds.

In the Compounds of Formula (I) and (II), the atoms may exhibit their natural isotopic abundances, or one or more of the atoms may be artificially enriched in a particular isotope having the same atomic number, but an atomic mass or mass number different from the atomic mass or mass number predominantly found in nature. The present invention is meant to include all suitable isotopic variations of the compounds of generic Formula (I). For example, different isotopic forms of hydrogen (H) include protium ($^1$H) and deuterium ($^2$H). Protium is the predominant hydrogen isotope found in nature. Enriching for deuterium may afford certain therapeutic advantages, such as increasing in vivo half-life or reducing dosage requirements, or may provide a compound useful as a standard for characterization of biological samples. Isotopically-enriched Compounds of Formula (I) and (II) can be prepared without undue experimentation by conventional techniques well known to those skilled in the art or by processes analogous to those described in the Schemes and Examples herein using appropriate isotopically-enriched reagents and/or intermediates. In one embodiment, a Compound of Formula (I) or (II) has one or more of its hydrogen atoms replaced with deuterium.

Polymorphic forms of the Fused Tetracycle Derivatives, and of the salts, solvates, hydrates, esters and prodrugs of the Fused Tetracycle Derivatives, are intended to be included in the present invention.

The following abbreviations are used below and have the following meanings: Ac is acyl; AcCl is acetyl chloride; AcOH or HOAc is acetic acid; Amphos is (4-(N,N)-dimethylaminophenyl)-di-tertbutylphosphine; Aq is aqueous; $BF_3.OEt_2$ is boron trifluoride etherate; BOC or Boc is tert-butyloxycarbonyl; $Boc_2O$ is Boc anhydride; Boc-Pro-OH is Boc protected praline; L-Boc-Val-OH is Boc protected L-valine; n-BuLi is n-butyllithium; CBZ or Cbz is carbobenzoxy; DCM is dichloromethane; DDQ is 2,3-dichloro-5,6-dicyano-1,4-benzoquinone; Dess-Martin reagent is, 1,1-Triacetoxy-1,1-dihydro-1,2-benziodoxol-3(1H)-one; DIPEA is diisopropylethylamine; DME is dimethoxyethane; DMF is N,N-dimethylformamide; dppf is diphenylphosphinoferrocene; DMSO is dimethylsulfoxide; EtMgBr is ethylmagnesium bromide; EtOAc is ethyl acetate; $Et_2O$ is diethyl ether; $Et_3N$ or $NEt_3$ is triethylamine; HATU is O-(7-azabenzotriazol-1-yl)-N,N,N',N'-tetramethyluronium hexafluorophosphate; HPLC is high performance liquid chromatography; HRMS is high resolution mass spectrometry; KOAc is potassium acetate; LCMS is liquid chromatography/mass spectrometry; LiHMDS is lithium hexamethyldisilazide; LRMS is low resolution mass spectrometry; MeI is iodomethane; MeOH is methanol; NBS is N-bromosuccinimide; $NH_4OAc$ is ammonium acetate; NMM is N-methylmorpholine; Pd/C is palladium on carbon; $Pd(PPh_3)_4$ is tetrakis (triphenylphosphine) palladium(0); $PdCl_2(dppf)_2$ is [1,1'-Bis(diphenylphosphino)ferrocene]dichloro palladium(II); $PdCl_2(dppf)_2.CH_2Cl_2$ is [1,1'-Bis(diphenylphosphino)ferrocene]dichloro palladium (II) complex with dichloromethane; $pinacol_2B_2$ is bis(pinacolato)diboron; PPTS is pyridinium p-toluene sulfonate; RPLC is reverse-phase liquid chromatography; Select-F is 1-Chloromethyl-4-Fluoro-1,4-Diazoniabicyclo[2.2.2]Octane Bis-(Tetrafluoroborate); SEM-Cl is 2-(trimethylsilyl) ethoxymethyl chloride; TBAF is tetrabutylammonium fluoride; TBDMSCl is tert-butyldimethylsilyl chloride; TFA is trifluoroacetic acid; $Tf_2O$ is triflic anhydride; THF is tetrahydrofuran; TLC is thin-layer chromatography; and TosCl is p-toluenesulfonyl chloride.

The Compounds of Formula (I)

The present invention provides Fused Tetracycle Derivatives of Formula (I):

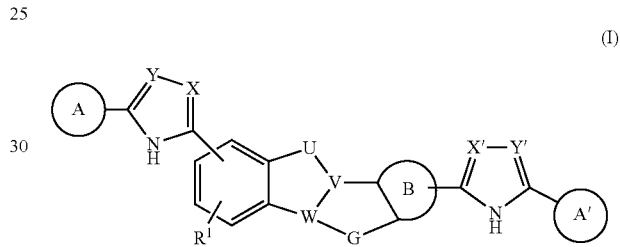

(I)

and pharmaceutically acceptable salts thereof, wherein A, A', B, G, $R^1$, U, V, W, X, X', Y and Y' are defined above for the Compounds of Formula (I)

In one embodiment, A and A' are each independently a 5-membered heterocycloalkyl group.

In another embodiment, A and A' are each independently a 6-membered heterocycloalkyl group.

In another embodiment, A and A' are each independently selected from:

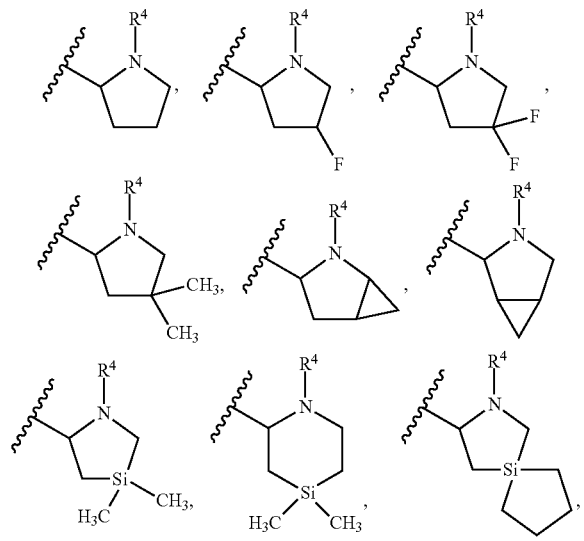

-continued

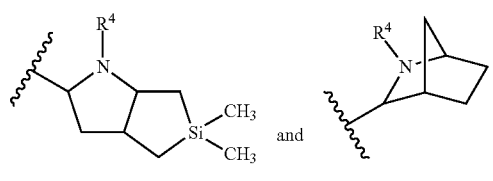

In still another embodiment, A and A' are each independently selected from:

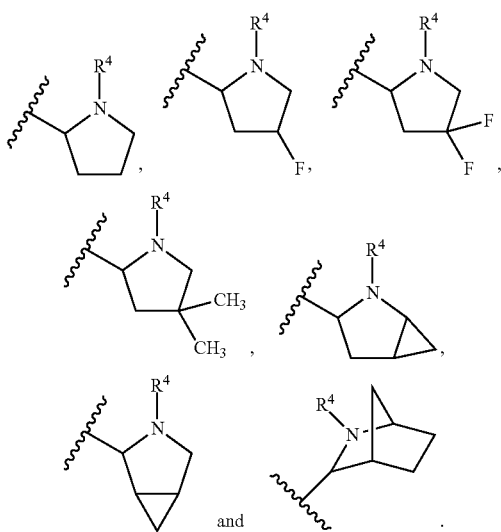

In another embodiment, A and A' are each independently selected from:

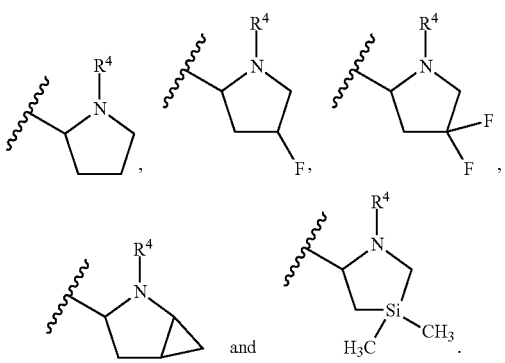

In another embodiment, A and A' are each independently selected from:

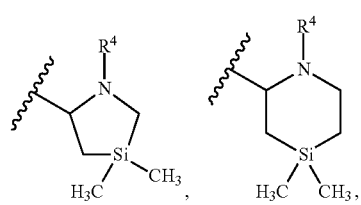

-continued

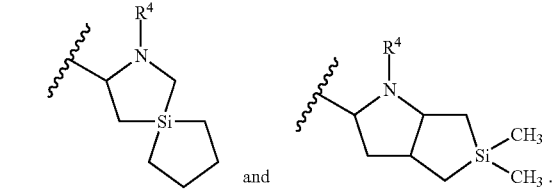

In another embodiment, A and A' are each:

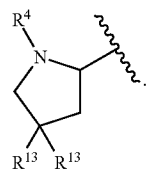

In another embodiment, A and A' are each:

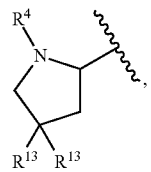

wherein each occurrence of $R^{13}$ is independently H, $CH_3$ or F.

In one embodiment, each occurrence of $R^4$ is independently —C(O)CH($R^7$)NHC(O)O—$R^{11}$.

In another embodiment, each occurrence of $R^4$ is independently:

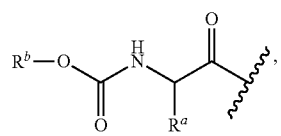

wherein $R^b$ is H, alkyl, haloalkyl, 3 to 6-membered cycloalkyl, 4 to 6-membered heterocycloalkyl, aryl or heteroaryl and $R^a$ is alkyl, haloalkyl, silylalkyl, 3 to 6-membered cycloalkyl or 4 to 6-membered heterocycloalkyl, aryl or heteroaryl.

In another embodiment, each occurrence of $R^4$ is independently:

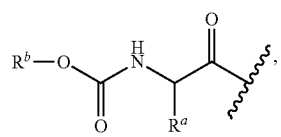

wherein $R^a$ is H, methyl, ethyl, propyl, isopropyl, t-butyl, cyclopropyl, —$CH_2CH_2Si(CH_3)_3$, —$CH_2CH_2CF_3$, pyranyl, benzyl or phenyl, and $R^b$ is methyl, ethyl or isopropyl.

In still another embodiment, each occurrence of $R^4$ is independently —C(O)CH(alkyl)-NHC(O)Oalkyl.

In another embodiment, each occurrence of $R^4$ is independently:

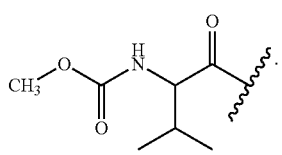 [SMILES: *C(=O)C(NC(=O)OC)C(C)C]

In one embodiment, A and A' are each independently selected from:

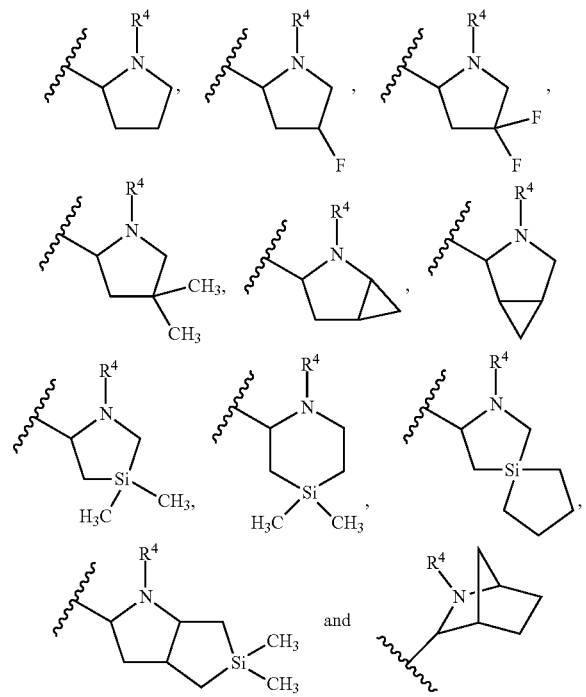

and R⁴ is:

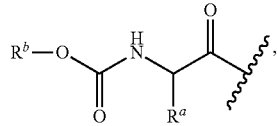

wherein $R^b$ is H, alkyl, haloalkyl, 3 to 6-membered cycloalkyl, 4 to 6-membered heterocycloalkyl, aryl or heteroaryl and $R^a$ is alkyl, haloalkyl, silylalkyl, 3 to 6-membered cycloalkyl or 4 to 6-membered heterocycloalkyl, aryl or heteroaryl.

In another embodiment, A and A' are each independently selected from:

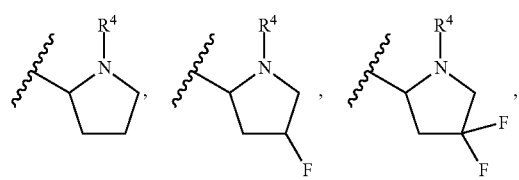

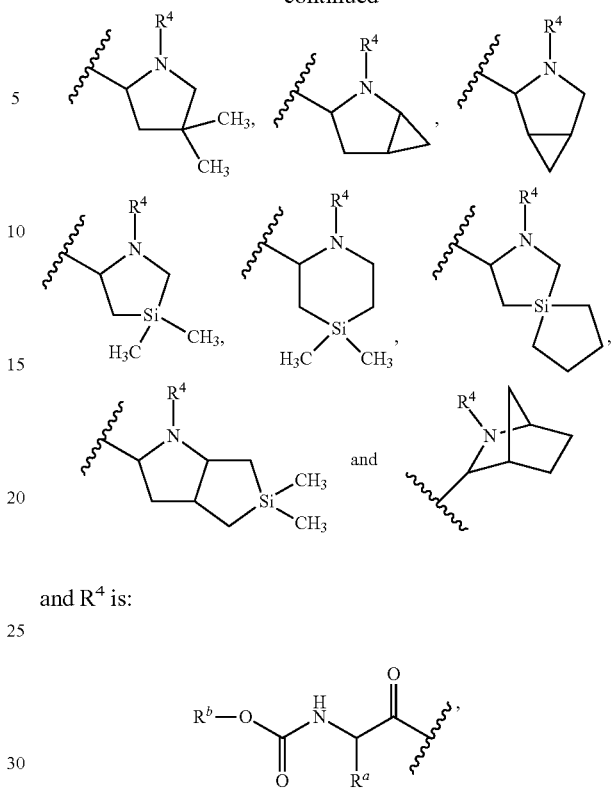

and R⁴ is:

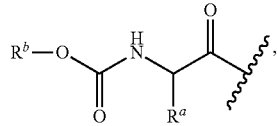

wherein $R^a$ is H, methyl, ethyl, propyl, isopropyl, t-butyl, cyclopropyl, —CH₂CH₂Si(CH₃)₃, —CH₂CH₂CF₃, pyranyl, benzyl or phenyl, and $R^b$ is methyl, ethyl or isopropyl.

In another embodiment, A and A' are each independently selected from:

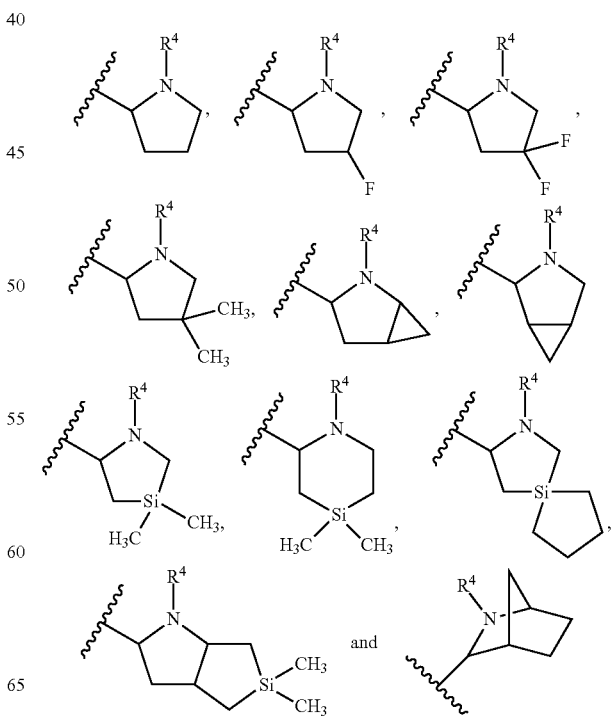

and $R^4$ is:

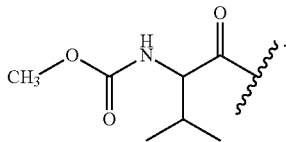 [SMILES: *C(=O)C(NC(=O)OC)C(C)C]

In yet another embodiment, A and A' are each:

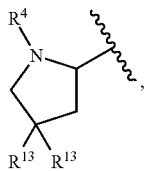

wherein each occurrence of $R^{13}$ is independently H, $CH_3$ or F; and $R^4$ is

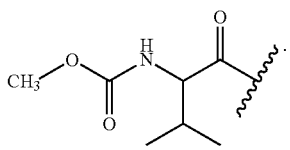 [SMILES: *C(=O)C(NC(=O)OC)C(C)C]

In one embodiment, B is phenyl.
In another embodiment, B is 5-membered heteroaryl.
In one embodiment, G is $—C(R^3)_2—C(R^3)_2—O—$, $C(R^3)_2—C(R^3)_2—C(R^3)_2—O—$, $—C(R^3)_2—C(R^3)_2—N(R^5)—$ and $C(R^3)_2—C(O)—N(R^5)—$.
In another embodiment, G is $—CH_2CH_2O—$, $—C(CH_3)C(O)—NH—$, $—CH_2CH_2N(CH_3)—$ or:

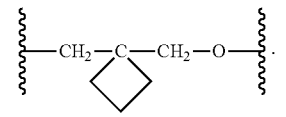

In one embodiment, the group U—V—W is $—C(R^2)=C—N—$.
In another embodiment, the group U—V—W is $—C(H)=C—N—$ or $—C(F)=C—N—$.
In one embodiment, $R^1$ is absent.
In another embodiment, $R^1$ is F.
In one embodiment, each occurrence of $R^{10}$ is independently H or F.
In another embodiment, each occurrence of $R^{10}$ is H.
In one embodiment, the group:

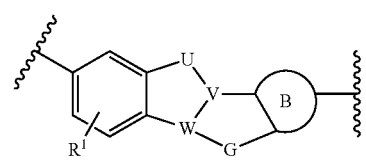

has the structure:

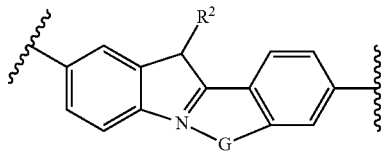

wherein $R^2$ is H or F and G is $—C(R^3)_2—C(R^3)_2—O—$, $C(R^3)_2—C(R^3)_2—C(R^3)_2—O—$, $—C(R^3)_2—C(R^3)_2—N(R^5)—$ and $C(R^3)_2—C(O)—N(R^5)—$.

In one embodiment, the group:

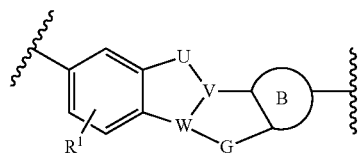

has the structure:

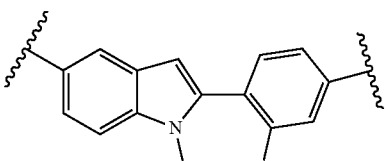

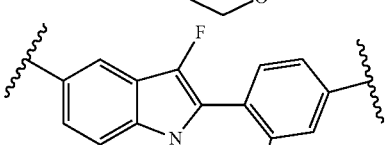

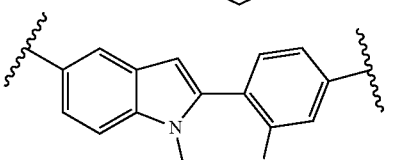 or

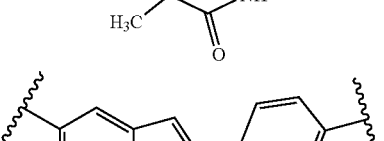

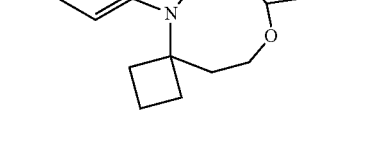

In one embodiment, variables A, A', B, G, $R^1$, U, V, W, X, X', Y and Y' for the Compounds of Formula (I) are selected independently of each other.

In another embodiment, the Compounds of Formula (I) are in substantially purified form.

In one embodiment, the Compounds of Formula (I) have the formula (Ia):

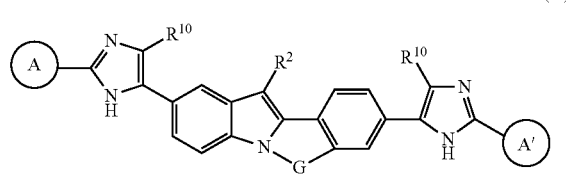

(Ia)

and pharmaceutically acceptable salts thereof, wherein:

A and A' are each independently a 5-membered monocyclic heterocycloalkyl, wherein said 5-membered monocyclic heterocycloalkyl group can be optionally and independently substituted on one or more ring carbon atoms with $R^{13}$, such that any two $R^{13}$ groups on the same ring, together with the carbon atom(s) to which they are attached, can join to form a fused, bridged or spirocyclic 3 to 6-membered cycloalkyl group or a fused, bridged or spirocyclic 4 to 6-membered heterocycloalkyl group, wherein said 5-membered monocyclic heterocycloalkyl contains from 1 to 2 ring heteroatoms, each independently selected from $N(R^4)$ and $Si(R^{16})_2$;

G is selected from $-C(R^3)_2-C(R^3)_2-O-$, $C(R^3)_2-C(R^3)_2-C(R^3)_2-O-$, $-C(R^3)_2-C(R^3)_2-N(R^5)-$ and $C(R^3)_2-C(O)-N(R^5)-$;

$R^2$ is selected from H, $C_1$-$C_6$ alkyl and halo;

each occurrence of $R^3$ is independently selected from H or $C_1$-$C_6$ alkyl and wherein two $R^3$ groups that are attached to the same carbon atom, together with the carbon atom to which they are attached, join to form a spirocyclic 3 to 6-membered cycloalkyl group;

each occurrence of $R^4$ is independently selected from $-C(O)R^{11}$ and $-C(O)-[C(R^7)_2]N(R^6)C(O)O-R^{11}$;

$R^{15}$ is selected from H, $C_1$-$C_6$ alkyl and aryl;

each occurrence of $R^6$ is independently selected from H and $C_1$-$C_6$ alkyl;

each occurrence of $R^7$ is independently selected from $C_1$-$C_6$ alkyl, 3 to 6-membered cycloalkyl and aryl;

each occurrence of $R^{10}$ is independently selected from H and halo;

each occurrence of $R^{11}$ is independently $C_1$-$C_6$ alkyl;

each occurrence of $R^{13}$ is independently selected from H, $C_1$-$C_6$ alkyl and halo; and each occurrence of $R^{16}$ is independently $C_1$-$C_6$ alkyl.

In one embodiment, for the Compounds of Formula (Ia), A and A' are each independently selected from:

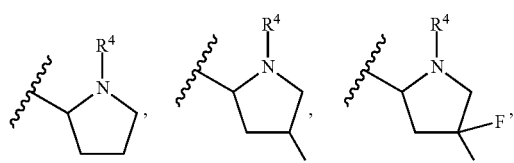

In another embodiment, for the Compounds of Formula (Ia), A and A' are each independently:

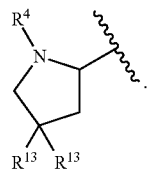

In another embodiment, for the Compounds of Formula (Ia), A and A' are each:

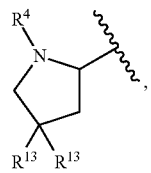

wherein each occurrence of $R^{13}$ is independently H or F.

In another embodiment, for the Compounds of Formula (Ia), each occurrence of $R^4$ is independently:

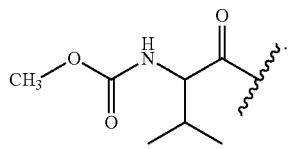 [SMILES: *C(=O)C(NC(=O)OC)C(C)C]

In one embodiment, for the Compounds of Formula (Ia), A and A' are each:

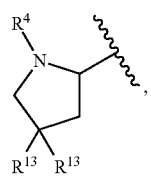

wherein each occurrence of $R^{13}$ is independently H or F and $R^4$ is

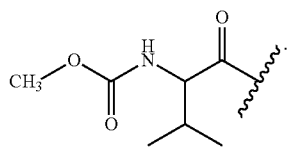 [SMILES: *C(=O)C(NC(=O)OC)C(C)C]

In another embodiment, for the Compounds of Formula (Ia), G is $-CH_2CH_2O-$, $-C(CH_3)C(O)-NH-$, $-CH_2CH_2N(CH_3)-$ or:

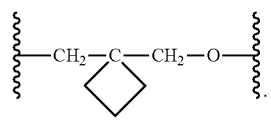

In one embodiment, for the Compounds of Formula (Ia), A and A' are each:

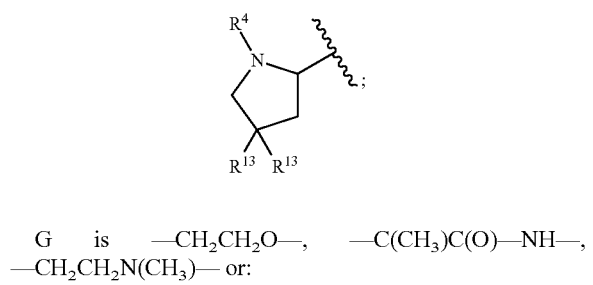

G is —CH$_2$CH$_2$O—, —C(CH$_3$)C(O)—NH—, —CH$_2$CH$_2$N(CH$_3$)— or:

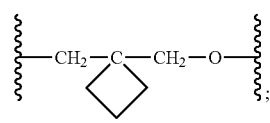

each occurrence of R$^4$ is:

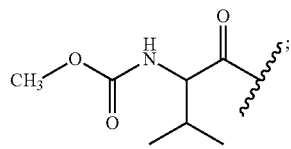 [SMILES: *C(=O)C(NC(=O)OC)C(C)C]

and each occurrence of R$^{13}$ is independently H or F.

In one embodiment, variables A, A', G, R$^1$, R$^2$, R$^{10}$ and R$^{15}$ for the Compounds of Formula (Ia) are selected independently of each other.

In another embodiment, the Compounds of Formula (Ia) are in substantially purified form.

The Compounds of Formula (II)

The present invention also provides Fused Tetracycle Derivatives of Formula

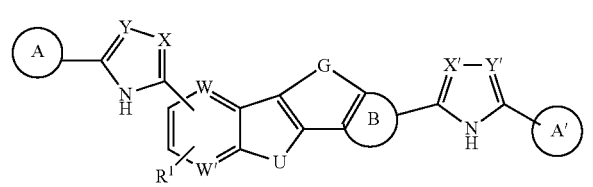

(II)

and pharmaceutically acceptable salts thereof, wherein A, A', B, G, R$^1$, U, X, X', Y and Y' are defined above for the Compounds of Formula (II).

In one embodiment, A and A' are each a 5-membered heterocycloalkyl group.

In another embodiment, A and A' are each a 6-membered heterocycloalkyl group.

In another embodiment, A and A' are each independently selected from:

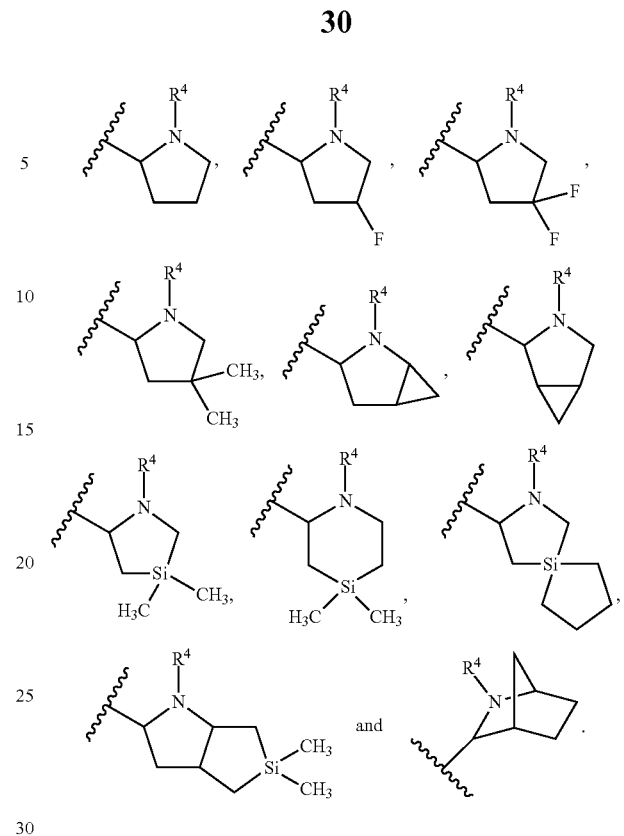

In still another embodiment, A and A' are each independently selected from:

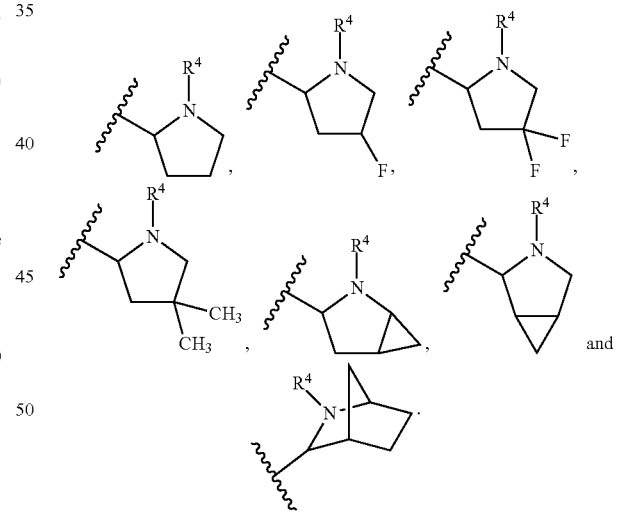

In another embodiment, A and A' are each independently selected from:

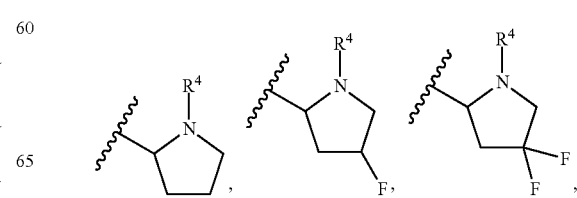

-continued

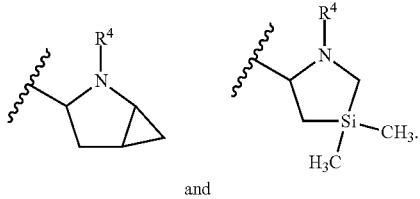

and

In another embodiment, A and A' are each independently selected from:

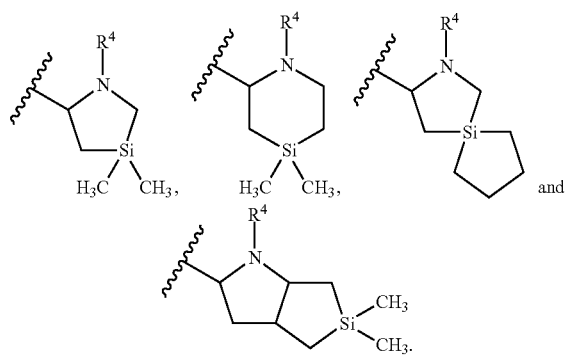

In another embodiment, A and A' are each:

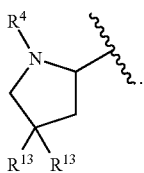

In another embodiment, A and A' are each:

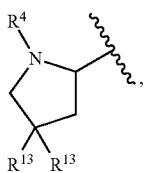

wherein each occurrence of $R^{13}$ is independently H, $CH_3$ or F.

In one embodiment, each occurrence of $R^4$ is independently —C(O)—CH($R^7$)N($R^6$)C(O)O—$R^{11}$.

In another embodiment, each occurrence of $R^4$ is independently:

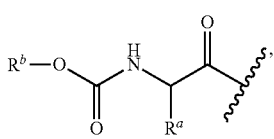

wherein $R^b$ is H, alkyl, haloalkyl, 3 to 6-membered cycloalkyl, 4 to 6-membered heterocycloalkyl, aryl or heteroaryl and $R^a$ is alkyl, haloalkyl, silylalkyl, 3 to 6-membered cycloalkyl or 4 to 6-membered heterocycloalkyl, aryl or heteroaryl.

In another embodiment, each occurrence of $R^4$ is independently:

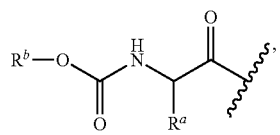

wherein $R^a$ is H, methyl, ethyl, propyl, isopropyl, t-butyl, cyclopropyl, —$CH_2CH_2Si(CH_3)_3$, —$CH_2CH_2CF_3$, pyranyl, benzyl or phenyl, and $R^b$ is methyl, ethyl or isopropyl.

In still another embodiment, each occurrence of $R^4$ is independently —C(O)CH(alkyl)-NHC(O)Oalkyl.

In another embodiment, each occurrence of $R^4$ is independently:

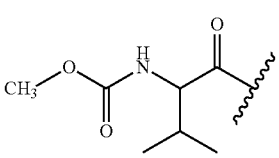

In one embodiment, A and A' are each independently selected from:

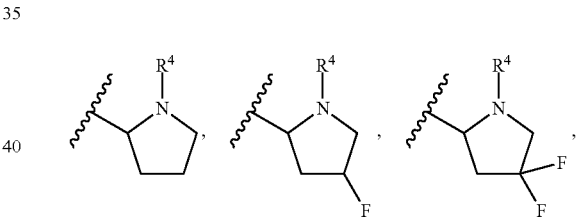

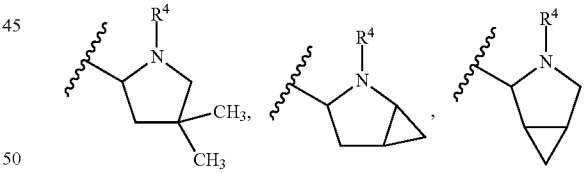

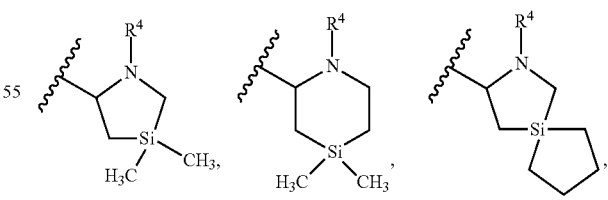

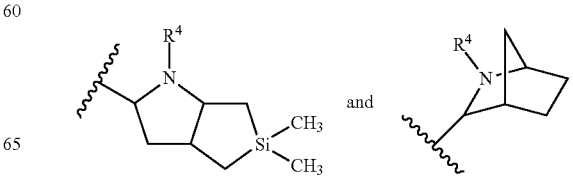

and and R⁴ is:

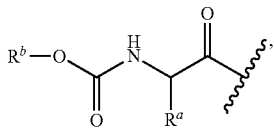

wherein R$^b$ is H, alkyl, haloalkyl, 3 to 6-membered cycloalkyl, 4 to 6-membered heterocycloalkyl, aryl or heteroaryl and R$^a$ is alkyl, haloalkyl, silylalkyl, 3 to 6-membered cycloalkyl or 4 to 6-membered heterocycloalkyl, aryl or heteroaryl.

In another embodiment, A and A' are each independently selected from:

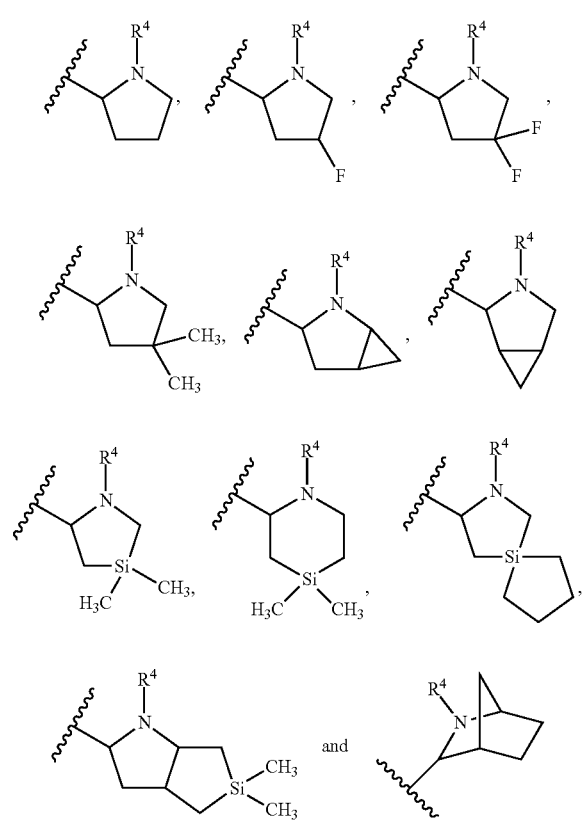

and R⁴ is:

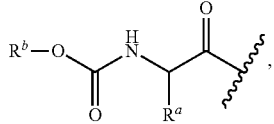

wherein R$^a$ is H, methyl, ethyl, propyl, isopropyl, t-butyl, cyclopropyl, —CH$_2$CH$_2$Si(CH$_3$)$_3$, —CH$_2$CH$_2$CF$_3$, pyranyl, benzyl or phenyl, and R$^b$ is methyl, ethyl or isopropyl.

In another embodiment, A and A' are each independently selected from:

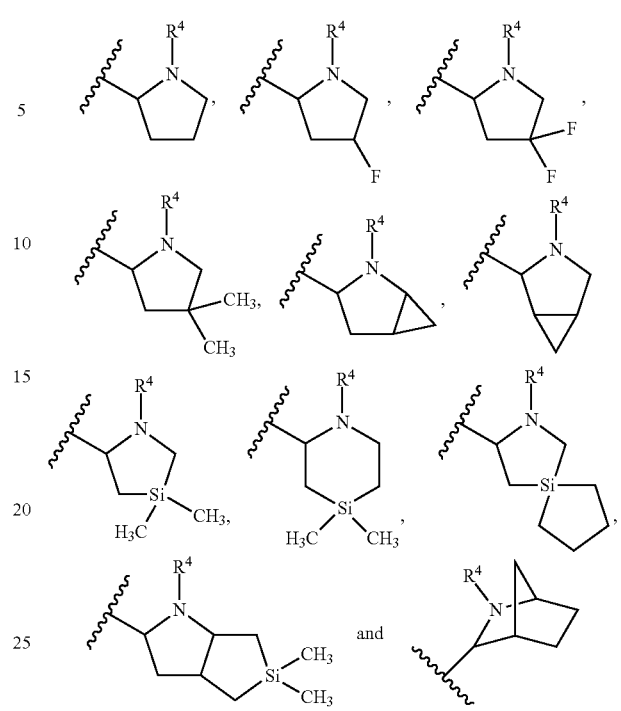

and R⁴ is:

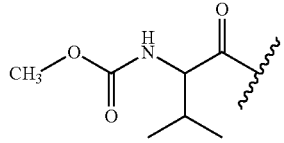

In yet another embodiment, A and A' are each:

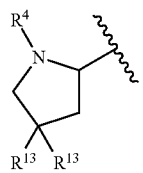

wherein each occurrence of R$^{13}$ is independently H, CH$_3$ or F; and R⁴ is

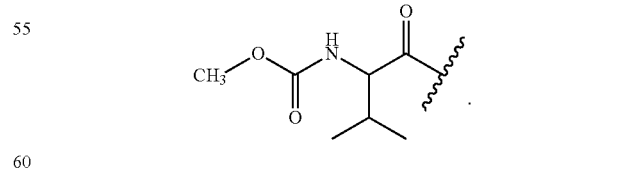

In one embodiment, B is phenyl.
In another embodiment, B is 5-membered heteroaryl.
In one embodiment, G is —C(R$^3$)$_2$—O—.
In another embodiment, G is selected from —C(R$^3$)$_2$—, —C(R$^3$)$_2$—C(R$^3$)$_2$—O— and —C(R$^3$)$_2$—C(R$^3$)$_2$—C(R$^3$)$_2$—.

In one embodiment, U is C(R²).
In another embodiment, U is CH.
In another embodiment, U is CF.
In one embodiment, R¹ is absent.
In another embodiment, R¹ is F.
In one embodiment, each occurrence of R¹⁰ is independently H or F.
In another embodiment, each occurrence of R¹⁰ is H.
In one embodiment, the group:

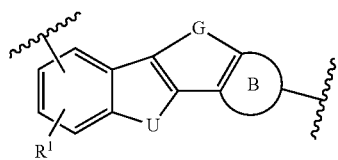

has the structure:

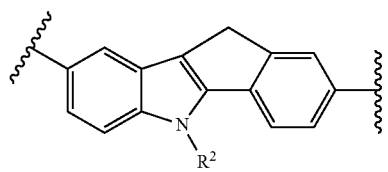

wherein R² is H, alkyl or —(C₁-C₆ alkylene)-O—(C₁-C₆ alkyl).

In another embodiment, the group:

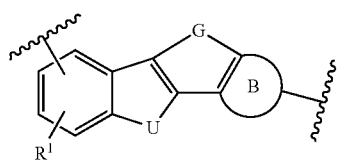

has the structure:

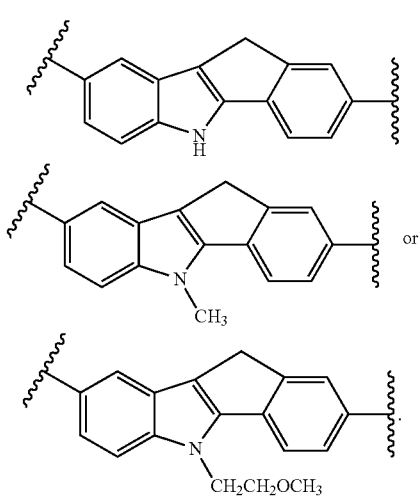

In another embodiment, the group:

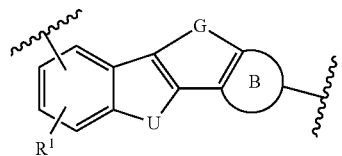

has the structure:

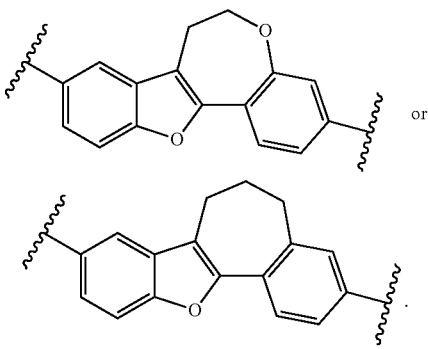

In one embodiment, variables A, A', B, G, R¹, U, X, X', Y and Y' for the Compounds of Formula (II) are selected independently of each other.

In another embodiment, the Compounds of Formula (II) are in substantially purified form.

In one embodiment, the Compounds of Formula (II) have the formula (IIa):

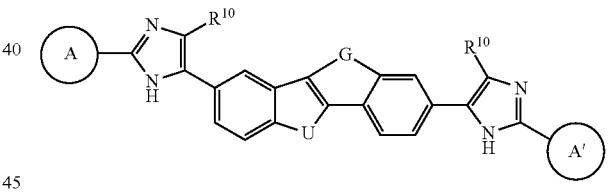

(IIa)

and pharmaceutically acceptable salts thereof, wherein:

A and A' are each independently a 5-membered monocyclic heterocycloalkyl, wherein said 5-membered monocyclic heterocycloalkyl group can be optionally and independently substituted on one or more ring carbon atoms with R¹³, such that any two R¹³ groups on the same ring, together with the carbon atoms to which they are attached, can join to form a fused, bridged or spirocyclic 3 to 6-membered cycloalkyl group or a fused, bridged or spirocyclic 4 to 6-membered heterocycloalkyl group, wherein said 5-membered monocyclic heterocycloalkyl contains from 1 to 2 ring heteroatoms, each independently selected from N(R⁴) and Si(R¹⁶)₂;

G is selected from —C(R³)₂—, —C(R³)₂—C(R³)₂—O— and —C(R³)₂—C(R³)₂—C(R³)₂—;

U is selected from N(R²) and O;

R² is selected from H, alkyl and —(C₁-C₆ alkylene)-O—(C₁-C₆ alkyl);

each occurrence of R³ is independently selected from H or C₁-C₆ alkyl;

each occurrence of R⁴ is independently selected from —C(O)R¹¹ and —C(O)—[C(R⁷)₂]N(R⁶)C(O)O—R¹¹;

each occurrence of $R^6$ is independently selected from H and $C_1$-$C_6$ alkyl;

each occurrence of $R^7$ is independently selected from $C_1$-$C_6$ alkyl, 3 to 6-membered cycloalkyl and aryl;

each occurrence of $R^{10}$ is independently selected from H and halo;

each occurrence of $R^{11}$ is independently $C_1$-$C_6$ alkyl;

each occurrence of $R^{13}$ is independently selected from H, $C_1$-$C_6$ alkyl and halo; and each occurrence of $R^{16}$ is independently $C_1$-$C_6$ alkyl.

In one embodiment, for the Compounds of Formula (IIa), A and A' are each independently selected from:

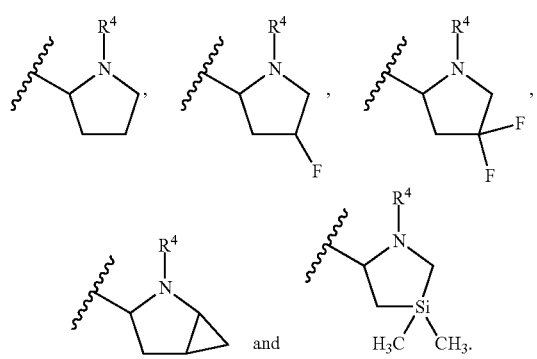

In another embodiment, for the Compounds of Formula (IIa), A and A' are each independently:

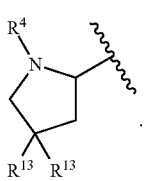

In another embodiment, for the Compounds of Formula (IIa), A and A' are each:

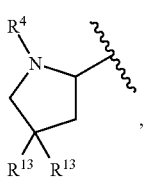

wherein each occurrence of $R^{13}$ is independently H, $CH_3$ or F.

In another embodiment, for the Compounds of Formula (IIa), each occurrence of $R^4$ is independently:

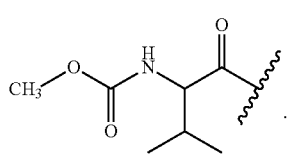 [SMILES: *C(=O)C(NC(=O)OC)C(C)C]

In one embodiment, for the Compounds of Formula (IIa), A and A' are each:

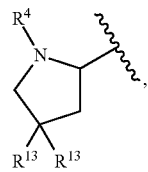

wherein each occurrence of $R^{13}$ is independently H, $CH_3$ or F and $R^4$ is

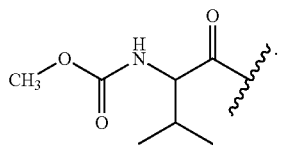 [SMILES: *C(=O)C(NC(=O)OC)C(C)C]

In another embodiment, for the Compounds of Formula (IIa), G is —$CH_2CH_2O$— or —$C(CH_3)C(O)$—NH—.

In one embodiment, for the Compounds of Formula (IIa), A and A' are each:

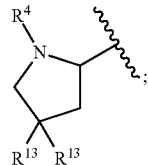

G is —$CH_2CH_2O$— or —$C(CH_3)C(O)$—NH—;

each occurrence of $R^4$ is:

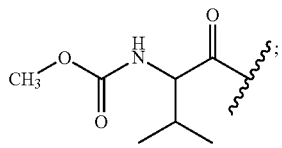 [SMILES: *C(=O)C(NC(=O)OC)C(C)C]

and each occurrence of $R^{13}$ is independently H, $CH_3$ or F.

In one embodiment, variables A, A', U, G and $R^{10}$ for the Compounds of Formula (IIa) are selected independently of each other.

In another embodiment, the Compounds of Formula (IIa) are in substantially purified form.

Other embodiments of the present invention include the following:

(a) A pharmaceutical composition comprising an effective amount of a Compound of Formula (I) or (II) or a pharmaceutically acceptable salt thereof, and a pharmaceutically acceptable carrier.

(b) The pharmaceutical composition of (a), further comprising a second therapeutic agent selected from the group consisting of HCV antiviral agents, immunomodulators, and anti-infective agents.

(c) The pharmaceutical composition of (b), wherein the HCV antiviral agent is an antiviral selected from the group consisting of HCV protease inhibitors and HCV NS5B polymerase inhibitors.

(d) A pharmaceutical combination that is (i) a Compound of Formula (I) or (II) and (ii) a second therapeutic agent selected from the group consisting of HCV antiviral agents, immunomodulators, and anti-infective agents; wherein the Compound of Formula (I) or (II) and the second therapeutic agent are each employed in an amount that renders the combination effective for inhibiting HCV replication, or for treating HCV infection and/or reducing the likelihood or severity of symptoms of HCV infection.

(e) The combination of (d), wherein the HCV antiviral agent is an antiviral selected from the group consisting of HCV protease inhibitors and HCV NS5B polymerase inhibitors.

(f) A method of inhibiting HCV replication in a subject in need thereof which comprises administering to the subject an effective amount of a Compound of Formula (I) or (II).

(g) A method of treating HCV infection and/or reducing the likelihood or severity of symptoms of HCV infection in a subject in need thereof which comprises administering to the subject an effective amount of a Compound of Formula (I) or (II).

(h) The method of (g), wherein the Compound of Formula (I) or (II) is administered in combination with an effective amount of at least one second therapeutic agent selected from the group consisting of HCV antiviral agents, immunomodulators, and anti-infective agents.

(i) The method of (h), wherein the HCV antiviral agent is an antiviral selected from the group consisting of HCV protease inhibitors and HCV NS5B polymerase inhibitors.

(j) A method of inhibiting HCV replication in a subject in need thereof which comprises administering to the subject the pharmaceutical composition of (a), (b) or (c) or the combination of (d) or (e).

(k) A method of treating HCV infection and/or reducing the likelihood or severity of symptoms of HCV infection in a subject in need thereof which comprises administering to the subject the pharmaceutical composition of (a), (b) or (c) or the combination of (d) or (e).

The present invention also includes a compound of the present invention for use (i) in, (ii) as a medicament for, or (iii) in the preparation of a medicament for: (a) medicine, (b) inhibiting HCV replication or (c) treating HCV infection and/or reducing the likelihood or severity of symptoms of HCV infection. In these uses, the compounds of the present invention can optionally be employed in combination with one or more second therapeutic agents selected from HCV antiviral agents, anti-infective agents, and immunomodulators.

Additional embodiments of the invention include the pharmaceutical compositions, combinations and methods set forth in (a)-(k) above and the uses set forth in the preceding paragraph, wherein the compound of the present invention employed therein is a compound of one of the embodiments, aspects, classes, sub-classes, or features of the compounds described above. In all of these embodiments, the compound may optionally be used in the form of a pharmaceutically acceptable salt or hydrate as appropriate.

It is further to be understood that the embodiments of compositions and methods provided as (a) through (k) above are understood to include all embodiments of the compounds, including such embodiments as result from combinations of embodiments.

The Compounds of Formula (I) and (II) may be referred to herein by chemical structure and/or by chemical name. In the instance that both the structure and the name of a Compound of Formula (I) or (II) are provided and a discrepancy is found to exist between the chemical structure and the corresponding chemical name, it is understood that the chemical structure will predominate.

Non-limiting examples of the Compounds of Formula (I) include compounds 7-15 as depicted in the Examples below, and pharmaceutically acceptable salts thereof.

Non-limiting examples of the Compounds of Formula (II) include compounds 1-6 as depicted in the Examples below, and pharmaceutically acceptable salts thereof.

Methods for Making the Fused Tetracycle Derivatives

The Compounds of Formula (I) and (II) may be prepared from known or readily prepared starting materials, following methods known to one skilled in the art of organic synthesis. Methods useful for making the Compounds of Formula (I) and (II) are set forth in the Examples below and generalized in Schemes 1-9 below. Alternative synthetic pathways and analogous structures will be apparent to those skilled in the art of organic synthesis.

Scheme 1 shows methods useful for making the compounds of formula G8, which correspond to the Compounds of Formula (I), wherein B is phenyl and the group —U—V—W— is —C(R$^2$)=CH—N—.

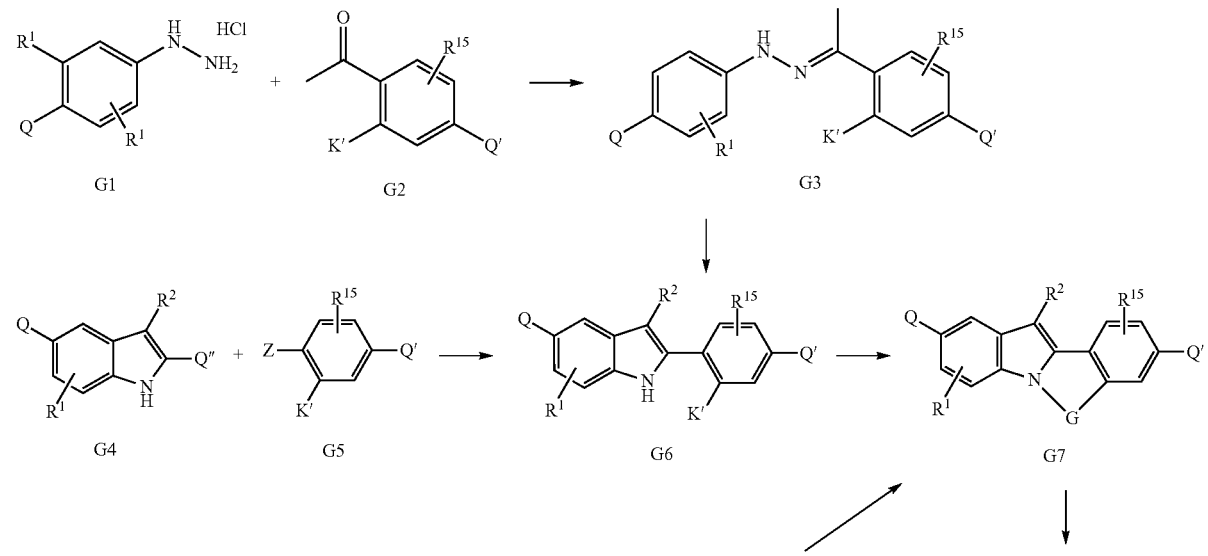

Scheme 1

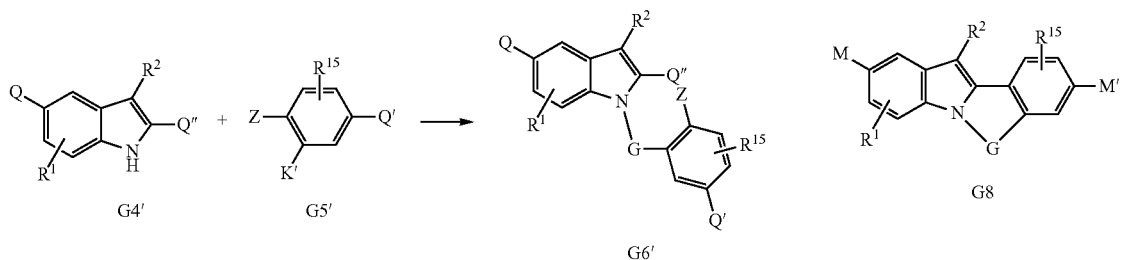

Wherein Q and Q' are each independently halo, hydroxy, or a protected hydroxy such as methoxy or benzyloxy; M, M', M" are each independently halo, hydroxy, or a protected hydroxy, triflate, boronic acid or boronic ester; K represents a group that can form a bond to the indole nitrogen. One skilled in the art of organic synthesis will recognize that when G is single or multiatom bridge, K should contain all the atoms of the bridge and a reactive group capable of forming a bond to nitrogen of the indole. Examples of reactive groups capable of forming a bond to nitrogen are well known to one skilled in the art of organic synthesis and non-limiting examples include an alkyl halide, vinyl halide, aldehyde group or a vicinal dihalide. Z represents an appropriate aryl coupling partner which will be well known to one skilled in the art of organic chemistry. An example of aryl couping partners include but are not limited to halide and triflate when the other partner is an arylboron or arylstannane derivative.

Tetracyclic compounds of formula G8 can be prepared from suitably substituted indole derivatives of formula G6. An indole derivative of formula G6 is cyclized to provide tetracyclic compounds of formula G7. Indole derivatives of formula G6 may be obtained commercially or prepared by using methods known to those skilled in the art of organic synthesis. In an illustrative example, the compounds of formula G6 can be made via dehydration of a hydrazide of formula G1 with a ketone of formula G2 to provide hydrazones of formula G3, which can then be cyclized in the presence of a strong acid such as PPA or a Lewis acid such as aluminum chloride, to provide the hydroxyl-substituted indole compounds of formula G4. A compound of formula G4 can then be reacted with an aldehyde of formula $R^3$—CHO to provice the cyclized compounds of formula G8, wherein G is —$CHR^3$—O—.

Compounds of formula G7 can be made, for example, via the arylation of the 2-position of an indole of formula G5 with a coupling partner of formula G6. A compound of formula G7 can then be cyclized by reacting Y and K' to provide the compounds of formula G8. It will be obvious to one skilled in the art of organic synthesis that the compounds of formulas G4 and G7 may undergo further functional group manipulations prior to cyclization as necessary in order to provide the scope of the Compounds of Formula (I).

Scheme 2 shows a method useful for making the compounds of formula G12, which correspond to the Compounds of Formula (I), wherein B is phenyl; X and X' are each CH; Y and Y' are each N; and the group —U—V—W— is —$C(R^2)$=CH—N—.

Scheme 2

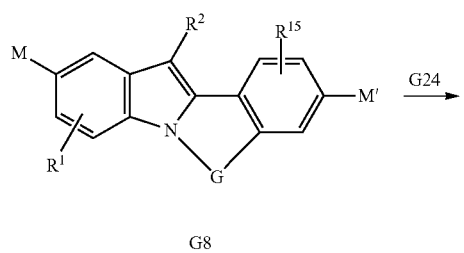

G8

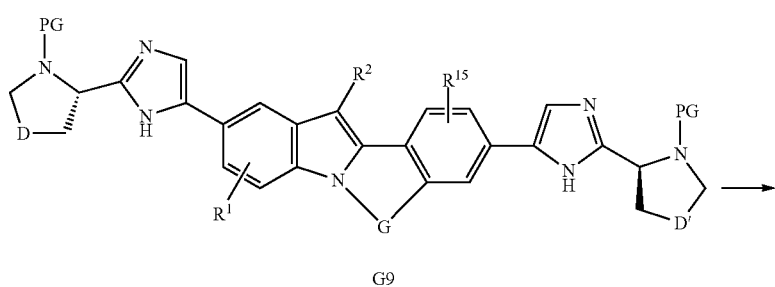

G9

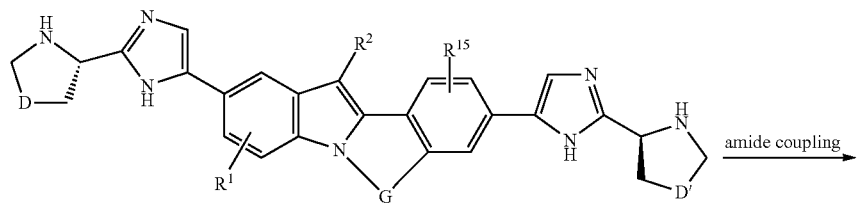

G10

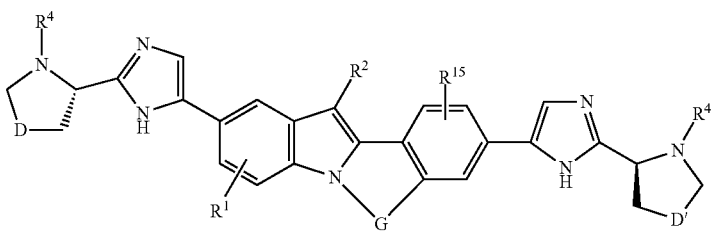

G11

Wherein D and D' are each independently C(R$^{13}$)$_2$, N(R$^4$), S, O or Si(R$^{16}$)$_2$; M and M' are each independently halo, triflate, boronic acid or boronic ester; PG is a protecting group, such as Boc or 4-methoxybenzyl; R$^4$ is —C(O)R$^{11}$, —C(O)—[C(R$^7$)$_2$]$_q$N(R$^6$)$_2$, —C(O)—[C(R$^7$)$_2$]$_q$—R$^{11}$, —C(O)—[C(R$^7$)$_2$]$_q$N(R$^6$)C(O)—R$^{11}$, —C(O)[C(R$^7$)$_2$]$_q$N (R$^6$)SO$_2$—R$^{11}$, —C(O)—[C(R$^7$)$_2$]$_q$N(R$^6$)C(O)O—R$^{11}$ or —C(O)—[C(R$^7$)$_2$]$_q$C(O)O—R$^{11}$; and G, R$^1$, R$^2$ and R$^{15}$ are defined above for the Compounds of Formula (I).

Depending on the identity of M and or M', the compounds of formula G8 can be coupled with a coupling partner of formula G24 (preparation of compounds of formula G24 is described below in Scheme 5) to provide the compounds of formula G9. Removal of the protecting groups of the compounds of formula G9 provides the diamino compounds of formula G10, which can then be reacted with an appropriately substituted carboxylic acid to form the R$^4$ groups of the di-amide compounds of formula G11, which correspond to the Compounds of Formula (I), wherein U is —N(R$^2$)—; W and W' are each —C(R$^1$)—; V and V' are each —C(R$^{15}$)—; X and X' are each —CH— and Y and Y' are each —N—.

Scheme 3 shows a method useful for making the compounds of formula G16, which correspond to the Compounds of Formula (I), wherein B is phenyl; X and X' are each CH; Y and Y' are each N; and the group —U—V—W— is —N═CH—N—.

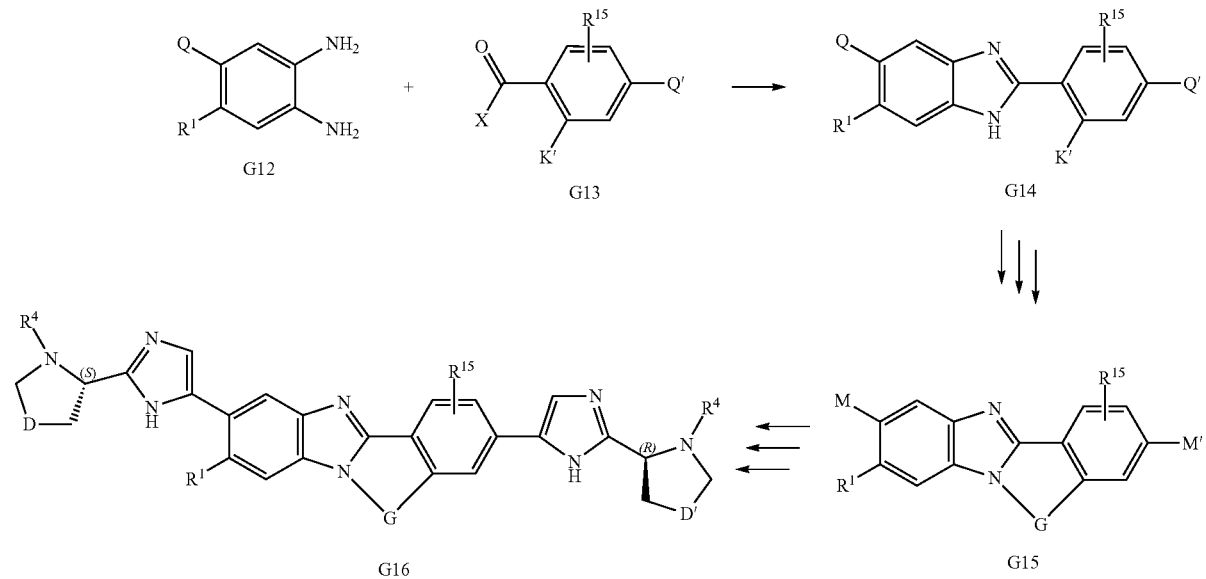

Scheme 3

Wherein D and D' are each independently $C(R^{13})_2$, $N(R^4)$, S, O or $Si(R^{16})_2$; M and M' are each independently halo, triflate, boronic acid or boronic ester; X is halo; $R^4$ is —C(O)$R^{11}$, —C(O)—[C($R^7$)$_2$]$_q$N($R^6$)$_2$, —C(O)—[C($R^7$)$_2$]$_q$—$R^{11}$, —C(O)—[C($R^7$)$_2$]$_q$N($R^6$)C(O)—$R^{11}$, —C(O)[C($R^7$)$_2$]$_q$N($R^6$)SO$_2$—$R^{11}$, —C(O)—[C($R^7$)$_2$]$_q$N($R^6$)C(O)O—$R^{11}$ or —C(O)—[C($R^7$)$_2$]$_q$C(O)O—$R^{11}$; K, Q and Q' are defined above in connection with Scheme 1; and G, $R^2$ and $R^{15}$ are defined above for the Compounds of Formula (I).

A 2-amino aniline derivative of formula G12 can be reacted with an acyl halide of formula G13 to provide the 2-substituted benzimidazole compounds of formula G14. The compounds of formula G14. can be cyclized and derivatized to provide compounds of formula G15, using at methods analogous to those described in Scheme 1 for the conversion of G6 to G8. A compound of formula G15 can then be carried forth to the compounds of formula G16 using methods analogous to those described in Scheme 2.

Scheme 4 shows a method useful for making the compounds of formula G20, which correspond to the Compounds of Formula (I), wherein B is pyridyl; X and X' are each CH; Y and Y' are each N; and the group —U—V—W— is —C($R^2$)=CH—N—.

analogous to those described in Scheme 1 for the conversion of G3 to G8. A compound of formula G19 can then be carried forth to the compounds of G20 using methods analogous to those described in Scheme 2.

Scheme 5 shows methods useful for making the compounds of formula G24, which are useful intermediates for making the Compounds of Formula (I) wherein X and X' are each CH and Y and Y' are each N.

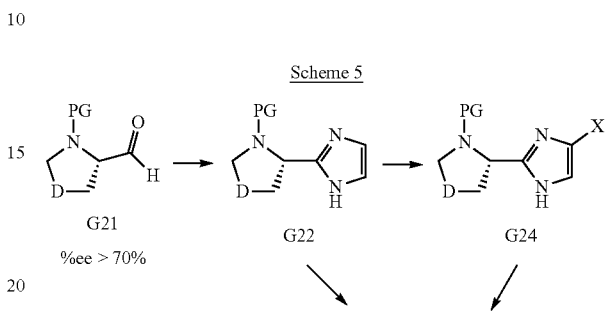

Scheme 5

G21 %ee > 70%

G22

G24

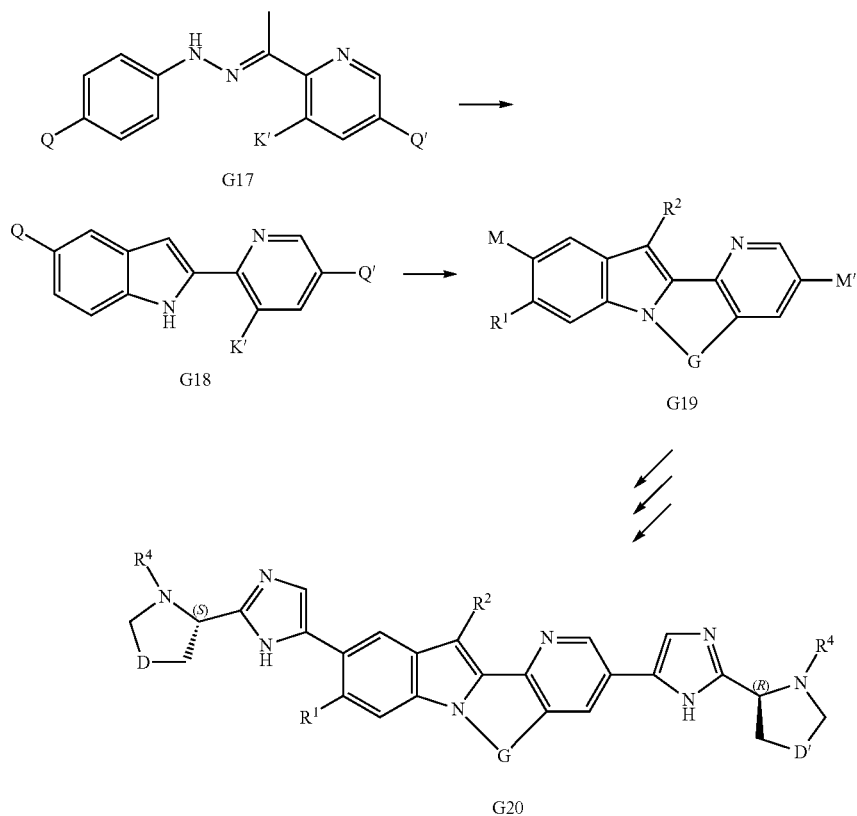

Scheme 4

G17

G18

G19

G20

Wherein D and D' are each independently $C(R^{13})_2$, $N(R^4)$, S, O or $Si(R^{16})_2$; M and M' are each independently halo, triflate, boronic acid or boronic ester; $R^4$ is —C(O)$R^{11}$, —C(O)—[C($R^7$)$_2$]$_q$N($R^6$)$_2$, —C(O)—[C($R^7$)$_2$]$_q$—$R^{11}$, —C(O)—[C($R^7$)$_2$]$_q$N($R^6$)C(O)—$R^{11}$, C(O)[C($R^7$)$_2$]$_q$N($R^6$)SO$_2$—$R^{11}$, —C(O)—[C($R^7$)$_2$]$_q$N($R^6$)C(O)O—$R^{11}$ or —C(O)—[C($R^7$)$_2$]$_q$C(O)O—$R^{11}$; and G, $R^1$ and $R^2$ are defined above for the Compounds of Formula (I).

A pyridyl hydrazone of formula G17 can be converted to the tetracyclic compounds of formula G19 using methods -continued

G23

Wherein D is $C(R^{13})_2$, $N(R^4)$, S, O or $Si(R^{16})_2$; X is halo or triflate; and PG is a amino protecting group, such as Boc or 4-methoxybenzyl.

An appropriately functionalized aldehyde of formula G21 can be reacted with glyoxal and ammonia. to provide a substituted imidazole of formula G22. A compound of formula G22 can subsequently be selectively mono-halogenated to provide a mono-halogenated imidazole compound of formula G24. Alternatively, a compound of formula G24 can subsequently be di-halogenated to provide a compound of formula G23, which is then selectively reduced to provide a mono-halogenated imidazole compound of formula G24.

Scheme 6 shows methods useful for making the tetracyclic compounds of formula G32, which are useful intermediates for making the Compounds of Formula (II), wherein B is phenyl, U is —$N(R^2)$—; and W and W' are each CH or —$C(R^1)$—.

aryl halide and a organostannane reagent, an acid chloride or an anion such as an alkoside, anilide or carbanion.

Tetracyclic compounds of formula G32 can be prepared from suitably substituted indole derivatives of formulas G4 and G31. Indole derivatives of general formula G4 and G7 may be obtained commercially or prepared by using methods known to those skilled in the art of organic synthesis. In an illustrative example, the compounds of formula G4 can be made via dehydration of a hydrazide of formula G1 with a ketone of formula G2 to provide hydrazones of formula G3, which can then be cyclized in the presence of a strong acid such as PPA or a Lewis acid such as aluminum chloride, to provide the hydroxyl-substituted indole compounds of formula G4. A compound of formula G4 can then be reacted with an aldehyde of formula $R^3$—CHO to provice the cyclized compounds of formula G8, wherein G is —$CHR^3$—O—.

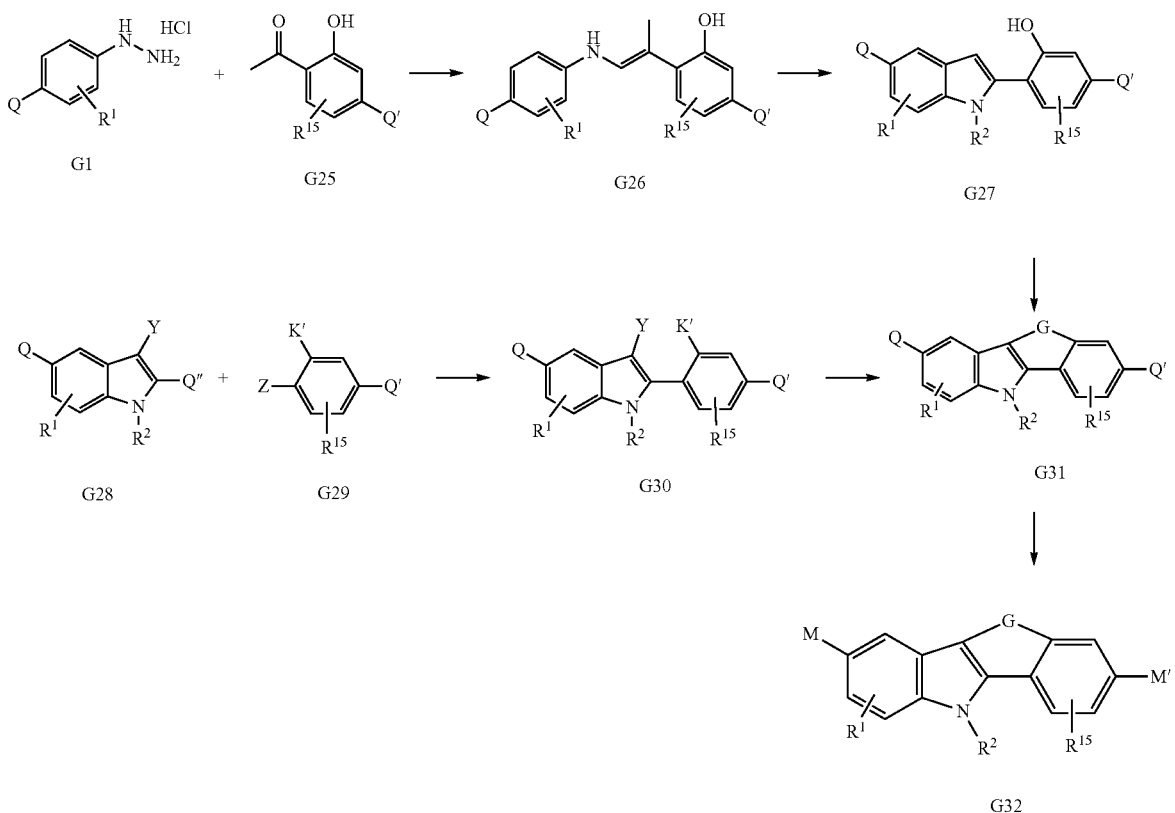

Scheme 6

Wherein Q and Q' are each independently halo, hydroxy, or a protected hydroxy such as methoxy or benzyloxy; M, M', M" are each independently halo, hydroxy, or a protected hydroxy, triflate, boronic acid or boronic ester;

M' and Z represent aryl copupling partners with form a carbon-carbon bond. K' and Y represent coupling partners which can form bridging group G. One skilled in the art of organic synthesis will recognize that when G is a two atom bridge, K' and Y can each contain one atom of the latent bridge, or that each of either K' or Y can contain both atoms. Well-known coupling partners include, but are not limited to, a benzylic halide and an alkoxide anion, a benzylic halide and a amine anion, an acyl chloride an aryl halide and organoboron reagent, an aryl halide and a organopalladium reagent, an Compounds of formula G7 can be made, for example, via the arylation of the 2-position of an indole of formula G5 with a coupling partner of formula G6. A compound of formula G7 can then be cyclized by reacting Y and K' to provide the compounds of formula G8. It will be obvious to one skilled in the art of organic synthesis that the compounds of formulas G4 and G7 may undergo further functional group manipulations prior to cyclization as necessary in order to provide the scope of the Compounds of Formula (I).

Scheme 7 shows a method useful for making the compounds of formula G35, which correspond to the Compounds of Formula (II), wherein B is phenyl; U is —$N(R^2)$—; W and W' are each —$C(R^1)$—; X and X' are each —CH— and Y and Y' are each —N—.

Scheme 7

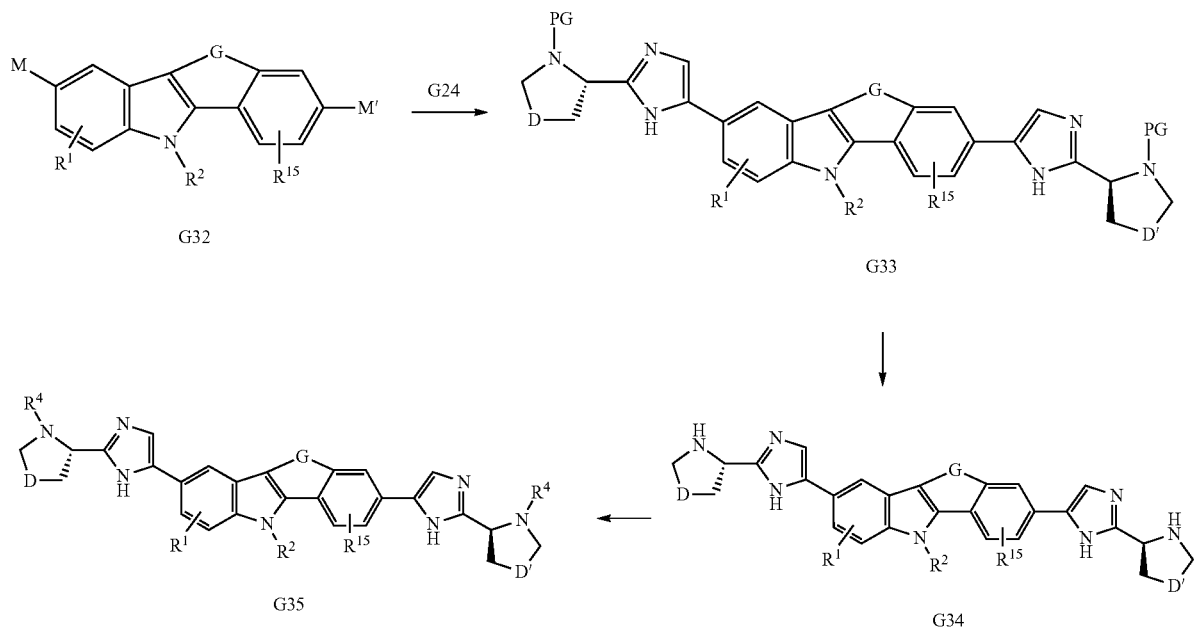

Wherein D and D' are each independently $C(R^{13})_2$, $N(R^4)$, S, O or $Si(R^{16})_2$; M and M' are each independently halo, triflate, boronic acid or boronic ester; PG is a protecting group, such as Boc or 4-methoxybenzyl; $R^4$ is —C(O)$R^{11}$, —C(O)—[C($R^7$)$_2$]$_q$N($R^6$)$_2$, —C(O)—[C($R^7$)$_2$]$_q$—$R^{11}$, —C(O)—[C($R^7$)$_2$]$_q$N($R^6$)C(O)—$R^{11}$, —C(O)[C($R^7$)$_2$]$_q$N($R^6$)SO$_2$—$R^{11}$, —C(O)—[C($R^7$)$_2$]$_q$N($R^6$)C(O)O—$R^{11}$ or —C(O)—[C($R^7$)$_2$]$_q$C(O)O—$R^{11}$; and G, $R^1$, $R^2$ and $R^{15}$ are defined above for the Compounds of Formula (I).

The compounds of formula G32 can be converted to the compounds of formula G35 using the method described in Scheme 2.

Scheme 8 shows a method useful for making the compounds of formula G38, which correspond to the Compounds of Formula (II), wherein B is phenyl, U is —O—; W and W' are each CH or —C($R^1$)—; X and X' are each —CH— and Y and Y' are each —N—.

Scheme 8

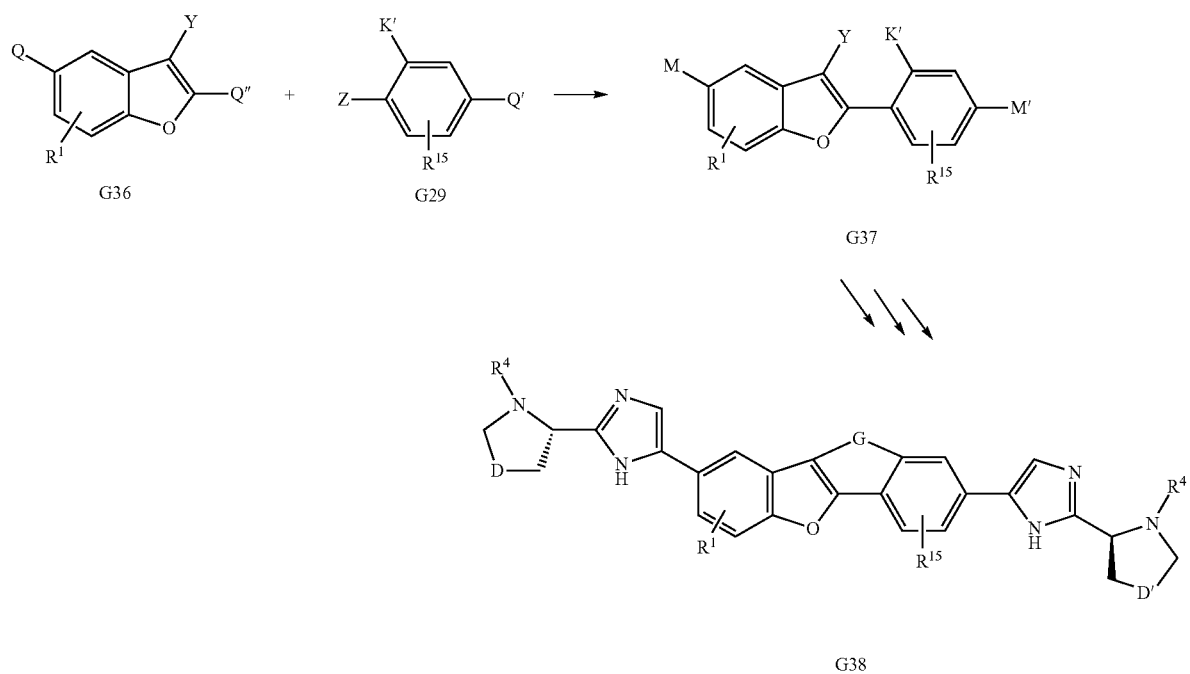

Wherein D and D' are each independently $C(R^{13})_2$, $N(R^4)$, S, O or $Si(R^{16})_2$; M and M' are each independently halo, triflate, boronic acid or boronic ester; Q and Q' are each independently halo, methoxy or benzyloxy; $R^4$ is —C(O)$R^{11}$, —C(O)—[C($R^7$)$_2$]$_q$N($R^6$)$_2$, —C(O)—[C($R^7$)$_2$]$_q$—$R^{11}$, —C(O)—[C($R^7$)$_2$]$_q$N($R^6$)C(O)—$R^{11}$, —C(O)[C($R^7$)$_2$]$_q$N($R^6$)SO$_2$—$R^{11}$, —C(O)—[C($R^7$)$_2$]$_q$N($R^6$)C(O)O—$R^{11}$ or —C(O)—[C($R^7$)$_2$]$_q$C(O)O—$R^{11}$; K', Q", Y and Z are defined in the Schemes above; and G, $R^2$ and $R^{15}$ are defined above for the Compounds of Formula (I).

A substituted benzoxazole of formula G36 can be arylated at the 2-position with coupling partner of formula G29 using methods analogous to those described in Scheme 1 for the formation of G6 from G4 and G5, to provide the 2-aryl benzoxazoles of formula G37. A compound of formula G37 can then be carried forth to the compounds of G38 using methods analogous to those described in Scheme 2.

Scheme 9 shows a method useful for making the compounds of formula G41, which correspond to the Compounds of Formula (II), wherein B is pyridyl, U is —N($R^2$)—; W and W' are each CH or —C($R^1$)—; X and X' are each —CH— and Y and Y' are each —N—.

to proline, 4-(R)-fluoroproline, 4-(S)-fluoroproline, 4,4-difluoroproline, 4,4-dimethylsilylproline, aza-bicyclo[2.2.1] heptane carboxylic acid, aza-bicyclo[2.2.2]octane carboxylic acid, (S)-2-piperidine carboxylic acid, valine, alanine, norvaline, etc.) are incorporated as part of the structures. Methods have been described in the organic chemistry literature as well as in Banchard US 2009/0068140 (Published Mar. 9, 2009) for the preparation of such amino acid-derived intermediates.

One skilled in the art of organic synthesis will recognize that the synthesis of fused tetracyclic cores contained in Compounds of Formula (I) and (II) may require protection of certain functional groups (i.e., derivatization for the purpose of chemical compatibility with a particular reaction condition). Suitable protecting groups for the various functional groups of these compounds and methods for their installation and removal are well known in the art of organic chemistry. A summary of many of these methods can be found in Greene et al., *Protective Groups in Organic Synthesis*, Wiley-Interscience, New York, (1999).

One skilled in the art of organic synthesis will also recognize that one route for the synthesis of the fused tetracyclic cores of the Compounds of Formula (I) and (II) may be more

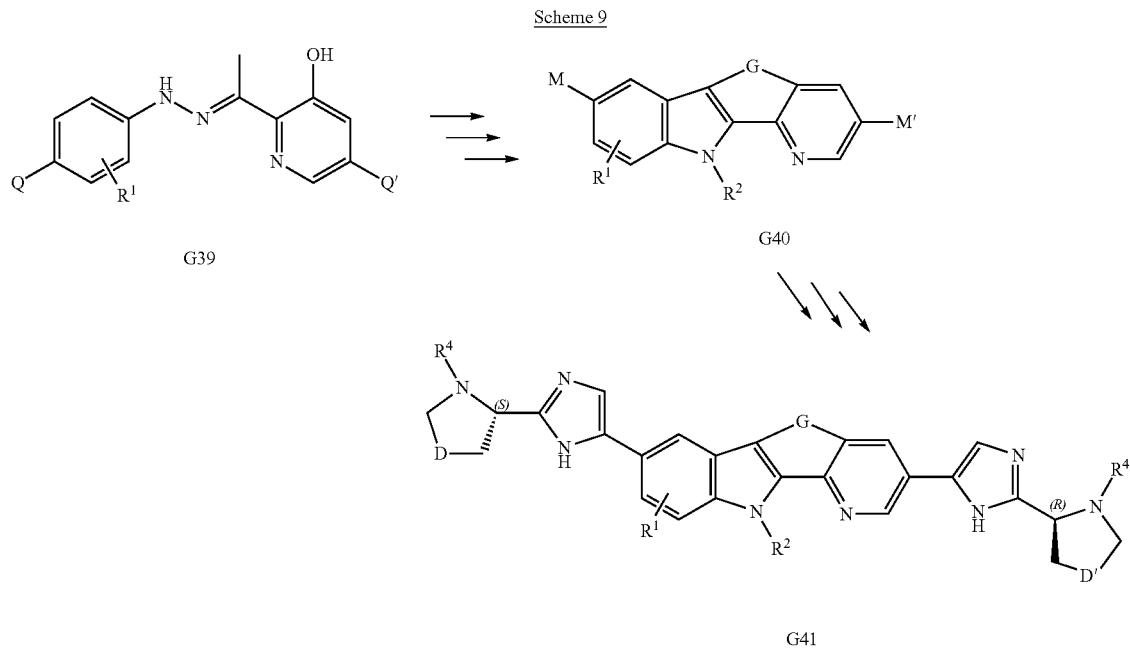

Scheme 9

Wherein D and D' are each independently $C(R^{13})_2$, $N(R^4)$, S, O or $Si(R^{16})_2$; M and M' are each independently halo, triflate, boronic acid or boronic ester; Q and Q' are each independently halo, methoxy or benzyloxy; $R^4$ is —C(O)$R^{11}$, —C(O)—[C($R^7$)$_2$]$_q$N($R^6$)$_2$, —C(O)—[C($R^7$)$_2$]$_q$—$R^{11}$, —C(O)—[C($R^7$)$_2$]$_q$N($R^6$)C(O)—$R^{11}$, —C(O)[C($R^7$)$_2$]$_q$N($R^6$)SO$_2$—$R^{11}$, —C(O)—[C($R^7$)$_2$]$_q$N($R^6$)C(O)O—$R^{11}$ or —C(O)—[C($R^7$)$_2$]$_q$C(O)O—$R^{11}$; and G, $R^1$ and $R^2$ are defined above for the Compounds of Formula (I).

A pyridyl hydrazone of formula G39 can be converted to the tetracyclic compounds of formula G40 using methods analogous to those described in Scheme 1 for the conversion of G3 to G8. A compound of formula G40 can then be carried forth to the compounds of G41 using methods analogous to those described in Scheme 2.

In some of the Compounds of Formula (I) and (II) contemplated in Schemes 1-9, amino acids (such as, but not limited desirable depending on the choice of appendage substituents. Additionally, one skilled in the art will recognize that in some cases the order of reactions may differ from that presented herein to avoid functional group incompatibilities and thus adjust the synthetic route accordingly.

One skilled in the art of organic synthesis will recognize that the synthesis of certain fused tetracyclic cores of the Compounds of Formula (I) and (II) require the construction of an amide bond. Methods useful for making such amide bonds, include but are not limited to, the use of a reactive carboxy derivative (e.g., an acid halide, or ester at elevated temperatures) or the use of an acid with a coupling reagent (e.g., HOBt, EDCI, DCC, HATU, PyBrop) with an amine.

The preparation of multicyclic intermediates useful for making the fused tetracyclic ring systems of the Compounds of Formula (I) and (II) have been described in the literature and in compendia such as "Comprehensive Heterocyclic Chemistry" editions I, II and III, published by Elsevier and edited by A. R. Katritzky & R. J K Taylor. Manipulation of the required substitution patterns have also been described in the available chemical literature as summarized in compendia such as "Comprehensive Organic Chemistry" published by Elsevier and edited by D H R. Barton and W. D. Ollis; "Comprehensive Organic Functional Group Transformations" edited by edited by A. R. Katritzky & R. J K Taylor and "Comprehensive Organic Transformation" published by Wily-C V H and edited by R. C. Larock.

The Compounds Formula (I) may contain one or more silicon atoms. The compounds contemplated in this invention in general can be prepared using the carba-analog methodology unless otherwise noted. A recent review of the synthesis of silicon containing compounds can be found in "Silicon Chemistry: from Atom to Extended Systems", Ed P. Jutzi & U. Schubet; ISBN 978-3-527-30647-3. Preparation of silyl containing amino acids has been described. See Bolm et al., *Angew. Chem. Int Ed.*, 39:2289 (2000). Descriptions of improved cellular update (Giralt, J. Am. Chem. Soc., 128: 8479 (2006)) and reduced metabolic processing of silyl containing compounds have been described (Johansson et al., *Drug Metabolism & Disposition*, 38:73 (2009)).

The starting materials used and the intermediates prepared using the methods set forth in Schemes 1-9 may be isolated and purified if desired using conventional techniques, including but not limited to filtration, distillation, crystallization, chromatography and alike. Such materials can be characterized using conventional means, including physical constants and spectral data.

Uses of the Fused Tetracycle Derivatives

The Fused Tetracycle Derivatives are useful in human and veterinary medicine for treating or preventing a viral infection in a patient. In one embodiment, the Fused Tetracycle Derivatives can be inhibitors of viral replication. In another embodiment, the Fused Tetracycle Derivatives can be inhibitors of HCV replication. Accordingly, the Fused Tetracycle Derivatives are useful for treating viral infections, such as HCV. In accordance with the invention, the Fused Tetracycle Derivatives can be administered to a patient in need of treatment or prevention of a viral infection.

Accordingly, in one embodiment, the invention provides methods for treating a viral infection in a patient comprising administering to the patient an effective amount of at least one Fused Tetracycle Derivative or a pharmaceutically acceptable salt thereof.

Treatment or Prevention of a Flaviviridae Virus

The Fused Tetracycle Derivatives can be useful for treating or preventing a viral infection caused by the Flaviviridae family of viruses.

Examples of Flaviviridae infections that can be treated or prevented using the present methods include but are not limited to, dengue fever, Japanese encephalitis, Kyasanur Forest disease, Murray Valley encephalitis, St. Louis encephalitis, Tick-borne encephalitis, West Nile encephalitis, yellow fever and Hepatitis C Virus (HCV) infection.

In one embodiment, the Flaviviridae infection being treated is hepatitis C virus infection.

Treatment or Prevention of HCV Infection

The Fused Tetracycle Derivatives are useful in the inhibition of HCV (e.g., HCV NS5A), the treatment of HCV infection and/or reduction of the likelihood or severity of symptoms of HCV infection and the inhibition of HCV viral replication and/or HCV viral production in a cell-based system. For example, the Fused Tetracycle Derivatives are useful in treating infection by HCV after suspected past exposure to HCV by such means as blood transfusion, exchange of body fluids, bites, accidental needle stick, or exposure to patient blood during surgery or other medical procedures.

In one embodiment, the hepatitis C infection is acute hepatitis C. In another embodiment, the hepatitis C infection is chronic hepatitis C.

Accordingly, in one embodiment, the invention provides methods for treating HCV infection in a patient, the methods comprising administering to the patient an effective amount of at least one Fused Tetracycle Derivative or a pharmaceutically acceptable salt thereof. In a specific embodiment, the amount administered is effective to treat or prevent infection by HCV in the patient. In another specific embodiment, the amount administered is effective to inhibit HCV viral replication and/or viral production in the patient.

The Fused Tetracycle Derivatives are also useful in the preparation and execution of screening assays for antiviral compounds. For example the Fused Tetracycle Derivatives are useful for identifying resistant HCV replicon cell lines harboring mutations within NS5A, which are excellent screening tools for more powerful antiviral compounds. Furthermore, the Fused Tetracycle Derivatives are useful in establishing or determining the binding site of other antivirals to the HCV replicase.

The compositions and combinations of the present invention can be useful for treating a patient suffering from infection related to any HCV genotype. HCV types and subtypes may differ in their antigenicity, level of viremia, severity of disease produced, and response to interferon therapy as described in Holland et al., *Pathology*, 30(2):192-195 (1998). The nomenclature set forth in Simmonds et al., *J Gen Virol*, 74(Pt11):2391-2399 (1993) is widely used and classifies isolates into six major genotypes, 1 through 6, with two or more related subtypes, e.g., 1a and 1b. Additional genotypes 7-10 and 11 have been proposed, however the phylogenetic basis on which this classification is based has been questioned, and thus types 7, 8, 9 and 11 isolates have been reassigned as type 6, and type 10 isolates as type 3 (see Lamballerie et al., *J Gen Virol*, 78(Pt1):45-51 (1997)). The major genotypes have been defined as having sequence similarities of between 55 and 72% (mean 64.5%), and subtypes within types as having 75%-86% similarity (mean 80%) when sequenced in the NS-5 region (see Simmonds et al., *J Gen Virol*, 75(Pt 5):1053-1061 (1994)).

Combination Therapy

In another embodiment, the present methods for treating or preventing HCV infection can further comprise the administration of one or more additional therapeutic agents which are not Fused Tetracycle Derivatives.

In one embodiment, the additional therapeutic agent is an antiviral agent.

In another embodiment, the additional therapeutic agent is an immunomodulatory agent, such as an immunosuppressive agent.

Accordingly, in one embodiment, the present invention provides methods for treating a viral infection in a patient, the method comprising administering to the patient: (i) at least one Fused Tetracycle Derivative, or a pharmaceutically acceptable salt thereof, and (ii) at least one additional therapeutic agent that is other than a Fused Tetracycle Derivative, wherein the amounts administered are together effective to treat or prevent a viral infection.

When administering a combination therapy of the invention to a patient, therapeutic agents in the combination, or a pharmaceutical composition or compositions comprising therapeutic agents, may be administered in any order such as, for example, sequentially, concurrently, together, simultaneously and the like. The amounts of the various actives in such combination therapy may be different amounts (different dosage amounts) or same amounts (same dosage amounts). Thus, for non-limiting illustration purposes, a Fused Tetracycle Derivative and an additional therapeutic agent may be present in fixed amounts (dosage amounts) in a single dosage unit (e.g., a capsule, a tablet and the like).

In one embodiment, the at least one Fused Tetracycle Derivative is administered during a time when the additional therapeutic agent(s) exert their prophylactic or therapeutic effect, or vice versa.

In another embodiment, the at least one Fused Tetracycle Derivative and the additional therapeutic agent(s) are administered in doses commonly employed when such agents are used as monotherapy for treating a viral infection.

In another embodiment, the at least one Fused Tetracycle Derivative and the additional therapeutic agent(s) are administered in doses lower than the doses commonly employed when such agents are used as monotherapy for treating a viral infection.

In still another embodiment, the at least one Fused Tetracycle Derivative and the additional therapeutic agent(s) act synergistically and are administered in doses lower than the doses commonly employed when such agents are used as monotherapy for treating a viral infection.

In one embodiment, the at least one Fused Tetracycle Derivative and the additional therapeutic agent(s) are present in the same composition. In one embodiment, this composition is suitable for oral administration. In another embodiment, this composition is suitable for intravenous administration. In another embodiment, this composition is suitable for subcutaneous administration. In still another embodiment, this composition is suitable for parenteral administration.

Viral infections and virus-related disorders that can be treated or prevented using the combination therapy methods of the present invention include, but are not limited to, those listed above.

In one embodiment, the viral infection is HCV infection.

The at least one Fused Tetracycle Derivative and the additional therapeutic agent(s) can act additively or synergistically. A synergistic combination may allow the use of lower dosages of one or more agents and/or less frequent administration of one or more agents of a combination therapy. A lower dosage or less frequent administration of one or more agents may lower toxicity of therapy without reducing the efficacy of therapy.

In one embodiment, the administration of at least one Fused Tetracycle Derivative and the additional therapeutic agent(s) may inhibit the resistance of a viral infection to these agents.

Non-limiting examples of additional therapeutic agents useful in the present compositions and methods include an interferon, an immunomodulator, a viral replication inhibitor, an antisense agent, a therapeutic vaccine, a viral polymerase inhibitor, a nucleoside inhibitor, a viral protease inhibitor, a viral helicase inhibitor, a virion production inhibitor, a viral entry inhibitor, a viral assembly inhibitor, an antibody therapy (monoclonal or polyclonal), and any agent useful for treating an RNA-dependent polymerase-related disorder.

In one embodiment, the additional therapeutic agent is a viral protease inhibitor.

In another embodiment, the additional therapeutic agent is a viral replication inhibitor.

In another embodiment, the additional therapeutic agent is an HCV NS3 protease inhibitor.

In still another embodiment, the additional therapeutic agent is an HCV NS5B polymerase inhibitor.

In another embodiment, the additional therapeutic agent is a nucleoside inhibitor.

In another embodiment, the additional therapeutic agent is an interferon.

In yet another embodiment, the additional therapeutic agent is an HCV replicase inhibitor.

In another embodiment, the additional therapeutic agent is an antisense agent.

In another embodiment, the additional therapeutic agent is a therapeutic vaccine.

In a further embodiment, the additional therapeutic agent is a virion production inhibitor.

In another embodiment, the additional therapeutic agent is an antibody therapy.

In another embodiment, the additional therapeutic agent is an HCV NS2 inhibitor.

In still another embodiment, the additional therapeutic agent is an HCV NS4A inhibitor.

In another embodiment, the additional therapeutic agent is an HCV NS4B inhibitor.

In another embodiment, the additional therapeutic agent is an HCV NS5A inhibitor In yet another embodiment, the additional therapeutic agent is an HCV NS3 helicase inhibitor.

In another embodiment, the additional therapeutic agent is an HCV IRES inhibitor.

In another embodiment, the additional therapeutic agent is an HCV p7 inhibitor.

In a further embodiment, the additional therapeutic agent is an HCV entry inhibitor.

In another embodiment, the additional therapeutic agent is an HCV assembly inhibitor.

In one embodiment, the additional therapeutic agents comprise a viral protease inhibitor and a viral polymerase inhibitor.

In still another embodiment, the additional therapeutic agents comprise a viral protease inhibitor and an immunomodulatory agent.

In yet another embodiment, the additional therapeutic agents comprise a polymerase inhibitor and an immunomodulatory agent.

In another embodiment, the additional therapeutic agents comprise a viral protease inhibitor and a nucleoside.

In another embodiment, the additional therapeutic agents comprise an immunomodulatory agent and a nucleoside.

In one embodiment, the additional therapeutic agents comprise an HCV protease inhibitor and an HCV polymerase inhibitor.

In another embodiment, the additional therapeutic agents comprise a nucleoside and an HCV NS5A inhibitor.

In another embodiment, the additional therapeutic agents comprise a viral protease inhibitor, an immunomodulatory agent and a nucleoside.

In a further embodiment, the additional therapeutic agents comprise a viral protease inhibitor, a viral polymerase inhibitor and an immunomodulatory agent.

In another embodiment, the additional therapeutic agent is ribavirin.

HCV polymerase inhibitors useful in the present compositions and methods include, but are not limited to, VP-19744 (Wyeth/ViroPharma), PSI-7851 (Pharmasset), RG-7128 (Roche/Pharmasset), PSI-938 (Pharmasset), PSI-7977 (Pharmasset), PF-868554/filibuvir (Pfizer), VCH-759 (ViroChem Pharma), HCV-796 (Wyeth/ViroPharma), IDX-184 (Idenix), IDX-375 (Idenix), NM-283 (Idenix/Novartis), R-1626 (Roche), MK-0608 (Isis/Merck), INX-8014 (Inhibitex), INX-8018 (Inhibitex), INX-189 (Inhibitex), GS 9190 (Gilead), A-848837 (Abbott), ABT-333 (Abbott), ABT-072 (Abbott), A-837093 (Abbott), BI-207127 (Boehringer-Ingelheim), BILB-1941 (Boehringer-Ingelheim), MK-3281 (Merck), VCH222 (ViroChem), VCH916 (ViroChem), VCH716(ViroChem), GSK-71185 (Glaxo SmithKline), ANA598 (Anadys), GSK-625433 (Glaxo SmithKline), XTL-2125 (XTL Biopharmaceuticals), and those disclosed in Ni et al., *Current Opinion in Drug Discovery and Development*, 7(4):446 (2004); Tan et al., *Nature Reviews*, 1:867 (2002); and Beaulieu et al., *Current Opinion in Investigational Drugs*, 5:838 (2004).

Other HCV polymerase inhibitors useful in the present compositions and methods include, but are not limited to, those disclosed in International Publication Nos. WO 08/082484, WO 08/082488, WO 08/083351, WO 08/136815, WO 09/032116, WO 09/032123, WO 09/032124 and WO 09/032125.

Interferons useful in the present compositions and methods include, but are not limited to, interferon alfa-2a, interferon alfa-2b, interferon alfacon-1 and PEG-interferon alpha conjugates. "PEG-interferon alpha conjugates" are interferon alpha molecules covalently attached to a PEG molecule. Illustrative PEG-interferon alpha conjugates include interferon alpha-2a (Roferon™, Hoffman La-Roche, Nutley, N.J.) in the form of pegylated interferon alpha-2a (e.g., as sold under the trade name Pegasys™), interferon alpha-2b (Intron™, from Schering-Plough Corporation) in the form of pegylated interferon alpha-2b (e.g., as sold under the trade name PEG-Intron™ from Schering-Plough Corporation), interferon alpha-2b-XL (e.g., as sold under the trade name PEG-Intron™), interferon alpha-2c (Berofor Alpha™, Boehringer Ingelheim, Ingelheim, Germany), PEG-interferon lambda (Bristol-Myers Squibb and ZymoGenetics), interferon alfa-2b alpha fusion polypeptides, interferon fused with the human blood protein albumin (Albuferon™, Human Genome Sciences), Omega Interferon (Intarcia), Locteron controlled release interferon (Biolex/OctoPlus), Biomed-510 (omega interferon), Peg-IL-29 (ZymoGenetics), Locteron CR (Octoplus), IFN-α-2b-XL (Flamel Technologies), and consensus interferon as defined by determination of a consensus sequence of naturally occurring interferon alphas (Infergen™, Amgen, Thousand Oaks, Calif.).

Antibody therapy agents useful in the present compositions and methods include, but are not limited to, antibodies specific to IL-10 (such as those disclosed in US Patent Publication No. US2005/0101770, humanized 12G8, a humanized monoclonal antibody against human IL-10, plasmids containing the nucleic acids encoding the humanized 12G8 light and heavy chains were deposited with the American Type Culture Collection (ATCC) as deposit numbers PTA-5923 and PTA-5922, respectively), and the like).

Examples of viral protease inhibitors useful in the present compositions and methods include, but are not limited to, an HCV protease inhibitor.

HCV protease inhibitors useful in the present compositions and methods include, but are not limited to, those disclosed in U.S. Pat. Nos. 7,494,988, 7,485,625, 7,449,447, 7,442,695, 7,425,576, 7,342,041, 7,253,160, 7,244,721, 7,205,330, 7,192,957, 7,186,747, 7,173,057, 7,169,760, 7,012,066, 6,914,122, 6,911,428, 6,894,072, 6,846,802, 6,838,475, 6,800,434, 6,767,991, 5,017,380, 4,933,443, 4,812,561 and 4,634,697; U.S. Patent Publication Nos. US20020068702, US20020160962, US20050119168, US20050176648, US20050209164, US20050249702 and US20070042968; and International Publication Nos. WO 03/006490, WO 03/087092, WO 04/092161 and WO 08/124,148.

Additional HCV protease inhibitors useful in the present compositions and methods include, but are not limited to, SCH503034 (Boceprevir, Schering-Plough), SCH900518 (Schering-Plough), VX-950 (Telaprevir, Vertex), VX-500 (Vertex), VX-813 (Vertex), VBY-376 (Virobay), BI-201335 (Boehringer Ingelheim), TMC-435 (Medivir/Tibotec), ABT-450 (Abbott), TMC-435350 (Medivir), ITMN-191/R7227 (InterMune/Roche), EA-058 (Abbott/Enanta), EA-063 (Abbott/Enanta), GS-9132 (Gilead/Achillion), ACH-1095 (Gilead/Achillon), IDX-136 (Idenix), IDX-316 (Idenix), ITMN-8356 (InterMune), ITMN-8347 (InterMune), ITMN-8096 (InterMune), ITMN-7587 (InterMune), BMS-650032 (Bristol-Myers Squibb), VX-985 (Vertex) and PHX1766 (Phenomix).

Further examples of HCV protease inhibitors useful in the present compositions and methods include, but are not limited to, those disclosed in Landro et al., *Biochemistry*, 36(30): 9340-9348 (1997); Ingallinella et al., *Biochemistry*, 37(25): 8906-8914 (1998); Llinàs-Brunet et al., *Bioorg Med Chem Lett*, 8(13):1713-1718 (1998); Martin et al., *Biochemistry*, 37(33):11459-11468 (1998); Dimasi et al., *J Virol*, 71(10): 7461-7469 (1997); Martin et al., *Protein Eng*, 10(5):607-614 (1997); Elzouki et al., *J Hepat*, 27(1):42-48 (1997); *BioWorld Today*, 9(217):4 (Nov. 10, 1998); U.S. Patent Publication Nos. US2005/0249702 and US 2007/0274951; and International Publication Nos. WO 98/14181, WO 98/17679, WO 98/17679, WO 98/22496 and WO 99/07734 and WO 05/087731.

Further examples of HCV protease inhibitors useful in the present compositions and methods include, but are not limited to, the following compounds:

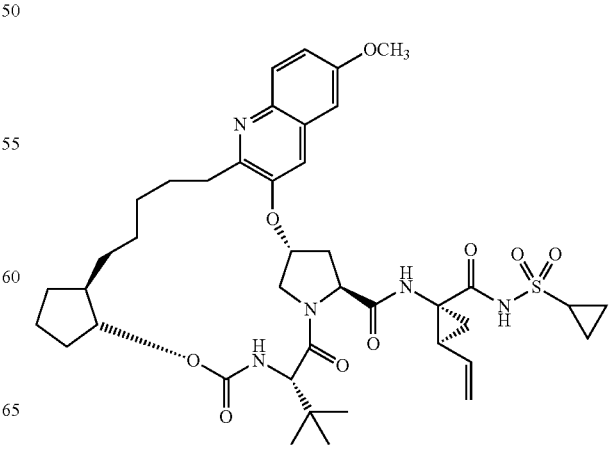

59
-continued
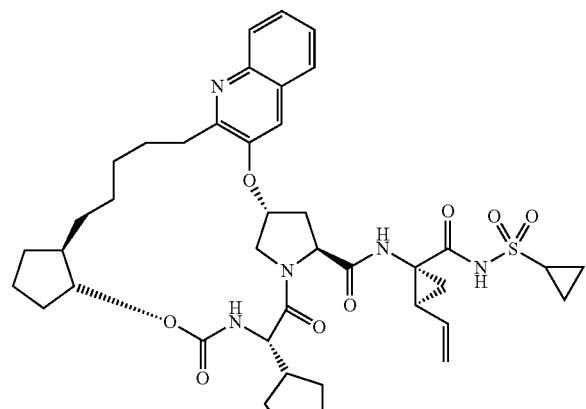
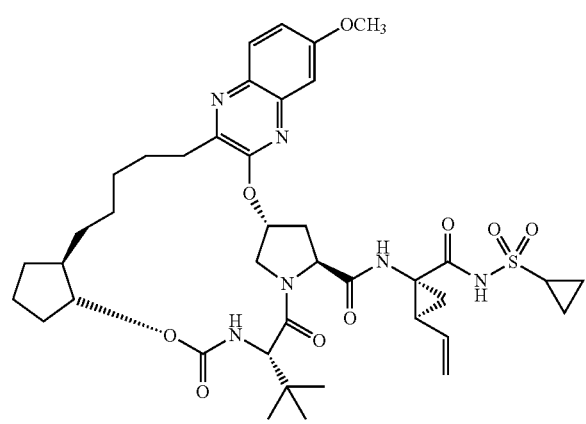
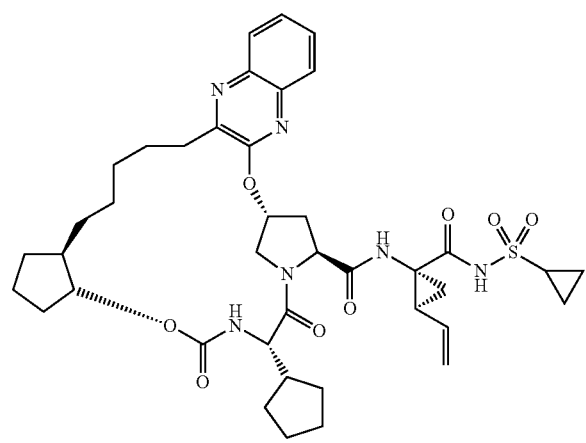
60
-continued
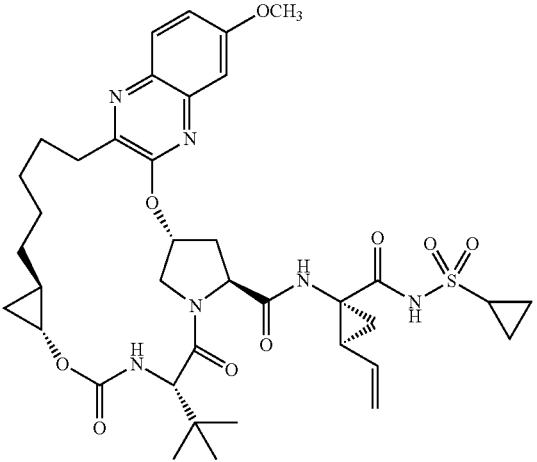
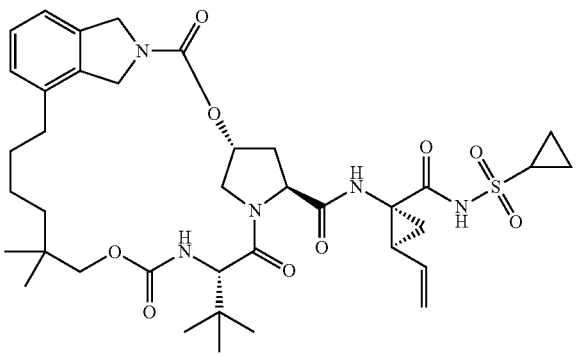
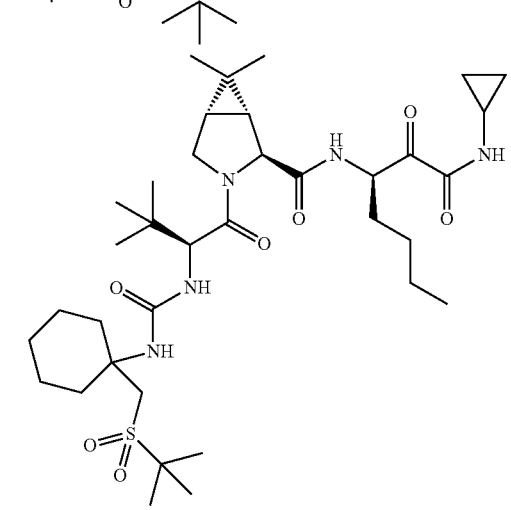

-continued
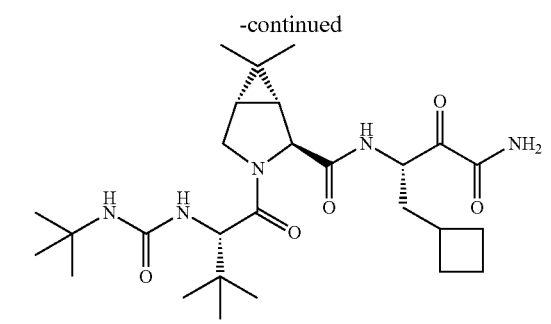
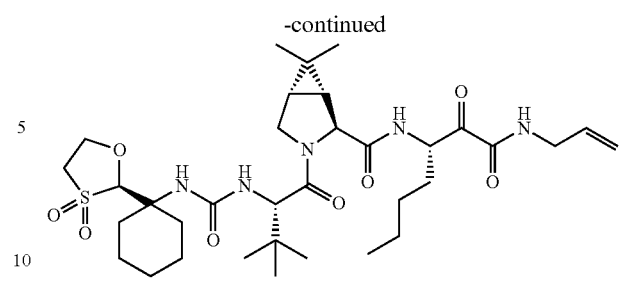
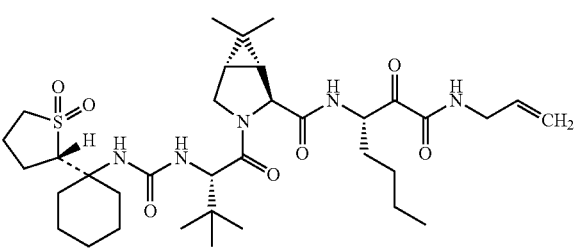
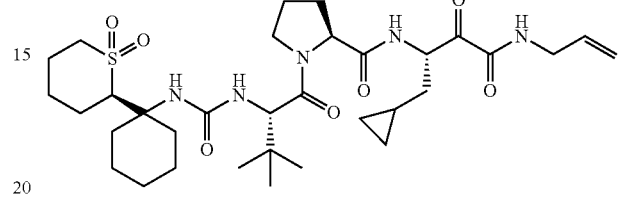
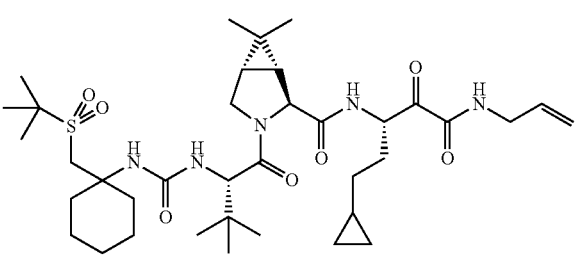
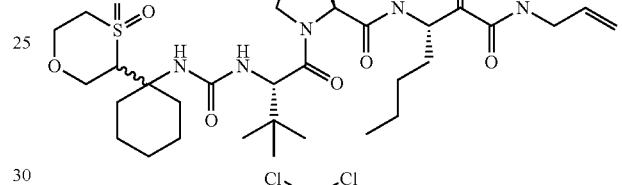
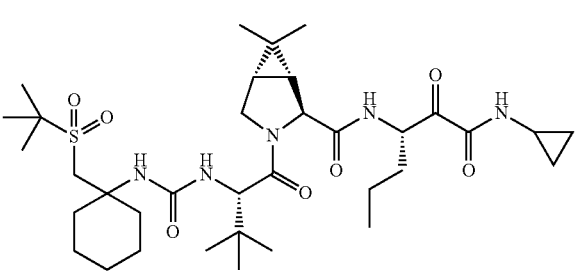
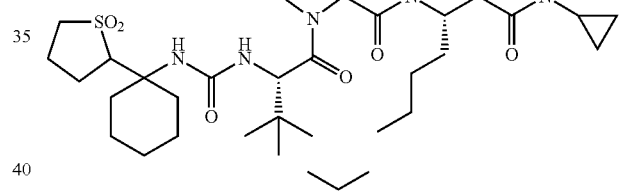
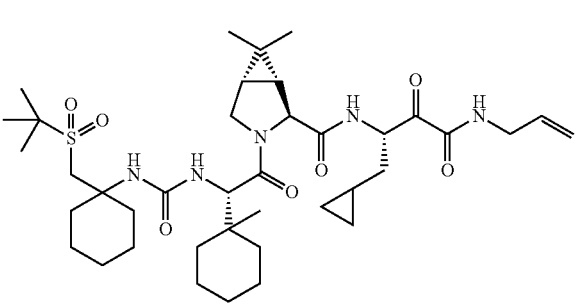
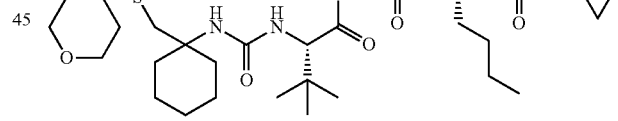
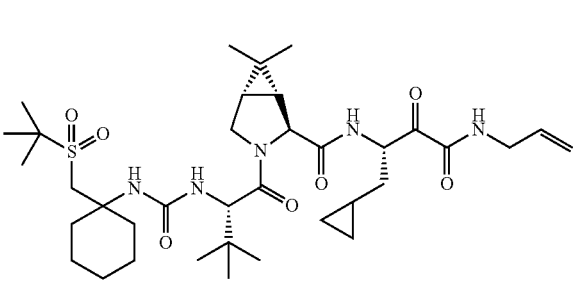
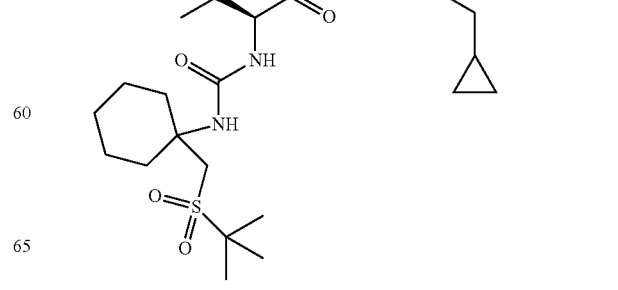

-continued

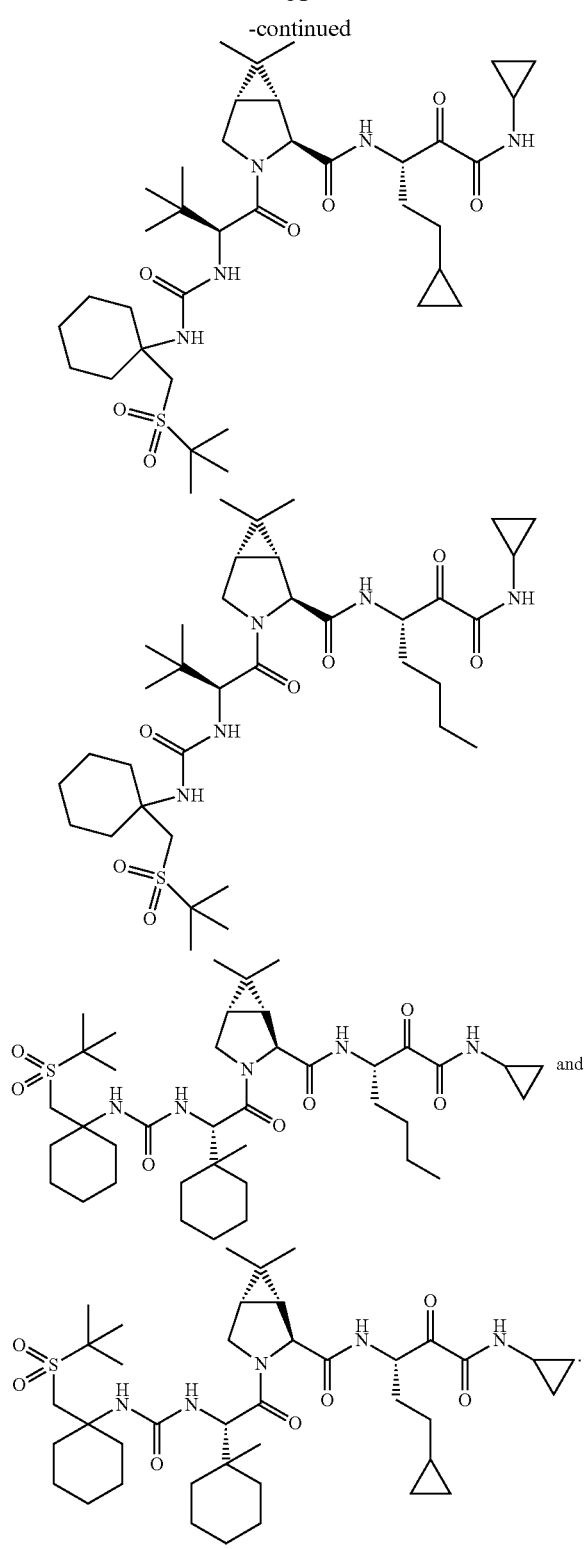

and

Viral replication inhibitors useful in the present compositions and methods include, but are not limited to, HCV replicase inhibitors, IRES inhibitors, NS4A inhibitors, NS3 helicase inhibitors, NS5A inhibitors, NS5B inhibitors, ribavirin, AZD-2836 (Astra Zeneca), BMS-790052 (Bristol-Myers Squibb, see Gao et al., *Nature,* 465:96-100 (2010)), viramidine, A-831 (Arrow Therapeutics); an antisense agent or a therapeutic vaccine.

HCV NS4A inhibitors useful in the present compositions and methods include, but are not limited to, those disclosed in U.S. Pat. Nos. 7,476,686 and 7,273,885; U.S. Patent Publication No. US20090022688; and International Publication Nos. WO 2006/019831 and WO 2006/019832. Additional HCV NS4A inhibitors useful in the present compositions and methods include, but are not limited to, AZD2836 (Astra Zeneca) and ACH-806 (Achillon Pharmaceuticals, New Haven, Conn.).

HCV replicase inhibitors useful in the present compositions and methods include, but are not limited to, those disclosed in U.S. Patent Publication No. US20090081636.

Therapeutic vaccines useful in the present compositions and methods include, but are not limited to, IC41 (Intercell Novartis), CSL123 (Chiron/CSL), GI 5005 (Globeimmune), TG-4040 (Transgene), GNI-103 (GENimmune), Hepavaxx C (ViRex Medical), ChronVac-C (Inovio/Tripep), PeviPRO™ (Pevion Biotect), HCV/MF59 (Chiron/Novartis) and Civacir (NABI).

Examples of further additional therapeutic agents useful in the present compositions and methods include, but are not limited to, Ritonavir (Abbott), TT033 (Benitec/Tacere Bio/Pfizer), Sirna-034 (Sirna Therapeutics), GNI-104 (GENimmune), GI-5005 (GlobeImmune), IDX-102 (Idenix), Levovirin™ (ICN Pharmaceuticals, Costa Mesa, Calif.); Humax (Genmab), ITX-2155 (Ithrex/Novartis), PRO 206 (Progenies), HepaCide-I (NanoVirocides), MX3235 (Migenix), SCY-635 (Scynexis); KPE02003002 (Kemin Pharma), Lenocta (VioQuest Pharmaceuticals), IET—Interferon Enhancing Therapy (Transition Therapeutics), Zadaxin (SciClone Pharma), VP 50406™ (Viropharma, Incorporated, Exton, Pa.); Taribavirin (Valeant Pharmaceuticals); Nitazoxanide (Romark); Debio 025 (Debiopharm); GS-9450 (Gilead); PF-4878691 (Pfizer); ANA773 (Anadys); SCV-07 (SciClone Pharmaceuticals); NIM-881 (Novartis); ISIS 14803™ (ISIS Pharmaceuticals, Carlsbad, Calif.); Heptazyme™ (Ribozyme Pharmaceuticals, Boulder, Colo.); Thymosin™ (SciClone Pharmaceuticals, San Mateo, Calif.); Maxamine™ (Maxim Pharmaceuticals, San Diego, Calif.); NKB-122 (JeriKen Bioscience Inc., North Carolina); Alinia (Romark Laboratories), INFORM-1 (a combination of R7128 and ITMN-191); and mycophenolate mofetil (Hoffman-LaRoche, Nutley, N.J.).

The doses and dosage regimen of the other agents used in the combination therapies of the present invention for the treatment or prevention of HCV infection can be determined by the attending clinician, taking into consideration the approved doses and dosage regimen in the package insert; the age, sex and general health of the patient; and the type and severity of the viral infection or related disease or disorder. When administered in combination, the Fused Tetracycle Derivative(s) and the other agent(s) can be administered simultaneously (i.e., in the same composition or in separate compositions one right after the other) or sequentially. This particularly useful when the components of the combination are given on different dosing schedules, e.g., one component is administered once daily and another component is administered every six hours, or when the preferred pharmaceutical compositions are different, e.g., one is a tablet and one is a capsule. A kit comprising the separate dosage forms is therefore advantageous.

Generally, a total daily dosage of the at least one Fused Tetracycle Derivative(s) alone, or when administered as combination therapy, can range from about 1 to about 2500 mg per day, although variations will necessarily occur depending on the target of therapy, the patient and the route of administration. In one embodiment, the dosage is from about 10 to about 1000 mg/day, administered in a single dose or in 2-4 divided doses. In another embodiment, the dosage is from about 1 to about 500 mg/day, administered in a single dose or in 2-4 divided doses. In still another embodiment, the dosage is from about to about 100 mg/day, administered in a single dose or in 2-4 divided doses. In yet another embodiment, the dosage is from about 1 to about 50 mg/day, administered in a single dose or in 2-4 divided doses. In another embodiment, the dosage is from about 500 to about 1500 mg/day, administered in a single dose or in 2-4 divided doses. In still another embodiment, the dosage is from about 500 to about 1000 mg/day, administered in a single dose or in 2-4 divided doses. In yet another embodiment, the dosage is from about 100 to about 500 g/day, administered in a single dose or in 2-4 divided doses.

In one embodiment, when the additional therapeutic agent is INTRON-A interferon alpha 2b (commercially available from Schering-Plough Corp.), this agent is administered by subcutaneous injection at 3 MIU (12 mcg)/0.5 mL/TIW for 24 weeks or 48 weeks for first time treatment.

In another embodiment, when the additional therapeutic agent is PEG-INTRON interferon alpha 2b pegylated (commercially available from Schering-Plough Corp.), this agent is administered by subcutaneous injection at 1.5 mcg/kg/week, within a range of 40 to 150 mcg/week, for at least 24 weeks.

In another embodiment, when the additional therapeutic agent is ROFERON A interferon alpha 2a (commercially available from Hoffmann-La Roche), this agent is administered by subcutaneous or intramuscular injection at 3 MIU (11.1 mcg/mL)/TIW for at least 48 to 52 weeks, or alternatively 6 MIU/TIW for 12 weeks followed by 3 MIU/TIW for 36 weeks.

In still another embodiment, when the additional therapeutic agent is PEGASUS interferon alpha 2a pegylated (commercially available from Hoffmann-La Roche), this agent is administered by subcutaneous injection at 180 mcg/1 mL or 180 mcg/0.5 mL, once a week for at least 24 weeks.

In yet another embodiment, when the additional therapeutic agent is INFERGEN interferon alphacon-1 (commercially available from Amgen), this agent is administered by subcutaneous injection at 9 mcg/TIW is 24 weeks for first time treatment and up to 15 mcg/TIW for 24 weeks for non-responsive or relapse treatment.

In a further embodiment, when the additional therapeutic agent is Ribavirin (commercially available as REBETOL ribavirin from Schering-Plough or COPEGUS ribavirin from Hoffmann-La Roche), this agent is administered at a daily dosage of from about 600 to about 1400 mg/day for at least 24 weeks.

In one embodiment, one or more compounds of the present invention are administered with one or more additional therapeutic agents selected from: an interferon, an immunomodulator, a viral replication inhibitor, an antisense agent, a therapeutic vaccine, a viral polymerase inhibitor, a nucleoside inhibitor, a viral protease inhibitor, a viral helicase inhibitor, a viral polymerase inhibitor a virion production inhibitor, a viral entry inhibitor, a viral assembly inhibitor, an antibody therapy (monoclonal or polyclonal), and any agent useful for treating an RNA-dependent polymerase-related disorder.

In another embodiment, one or more compounds of the present invention are administered with one or more additional therapeutic agents selected from an HCV protease inhibitor, an HCV polymerase inhibitor, an HCV replication inhibitor, a nucleoside, an interferon, a pegylated interferon and ribavirin. The combination therapies can include any combination of these additional therapeutic agents.

In another embodiment, one or more compounds of the present invention are administered with one additional therapeutic agent selected from an HCV protease inhibitor, an interferon, a pegylated interferon and ribavirin.

In still another embodiment, one or more compounds of the present invention are administered with two additional therapeutic agents selected from an HCV protease inhibitor, an HCV replication inhibitor, a nucleoside, an interferon, a pegylated interferon and ribavirin.

In another embodiment, one or more compounds of the present invention are administered with an HCV protease inhibitor and ribavirin. In another specific embodiment, one or more compounds of the present invention are administered with a pegylated interferon and ribavirin.

In another embodiment, one or more compounds of the present invention are administered with three additional therapeutic agents selected from an HCV protease inhibitor, an HCV replication inhibitor, a nucleoside, an interferon, a pegylated interferon and ribavirin.

In one embodiment, one or more compounds of the present invention are administered with one or more additional therapeutic agents selected from an HCV polymerase inhibitor, a viral protease inhibitor, an interferon, and a viral replication inhibitor. In another embodiment, one or more compounds of the present invention are administered with one or more additional therapeutic agents selected from an HCV polymerase inhibitor, a viral protease inhibitor, an interferon, and a viral replication inhibitor. In another embodiment, one or more compounds of the present invention are administered with one or more additional therapeutic agents selected from an HCV polymerase inhibitor, a viral protease inhibitor, an interferon, and ribavirin.

In one embodiment, one or more compounds of the present invention are administered with one additional therapeutic agent selected from an HCV polymerase inhibitor, a viral protease inhibitor, an interferon, and a viral replication inhibitor. In another embodiment, one or more compounds of the present invention are administered with ribavirin.

In one embodiment, one or more compounds of the present invention are administered with two additional therapeutic agents selected from an HCV polymerase inhibitor, a viral protease inhibitor, an interferon, and a viral replication inhibitor.

In another embodiment, one or more compounds of the present invention are administered with ribavirin, interferon and another therapeutic agent.

In another embodiment, one or more compounds of the present invention are administered with ribavirin, interferon and another therapeutic agent, wherein the additional therapeutic agent is selected from an HCV polymerase inhibitor, a viral protease inhibitor, and a viral replication inhibitor.

In still another embodiment, one or more compounds of the present invention are administered with ribavirin, interferon and a viral protease inhibitor.

In another embodiment, one or more compounds of the present invention are administered with ribavirin, interferon and an HCV protease inhibitor.

In another embodiment, one or more compounds of the present invention are administered with ribavirin, interferon and boceprevir or telaprevir.

In a further embodiment, one or more compounds of the present invention are administered with ribavirin, interferon and an HCV polymerase inhibitor.

In another embodiment, one or more compounds of the present invention are administered with pegylated-interferon alpha and ribavirin.

Compositions and Administration

Due to their activity, the Fused Tetracycle Derivatives are useful in veterinary and human medicine. As described above, the Fused Tetracycle Derivatives are useful for treating or preventing HCV infection in a patient in need thereof.

When administered to a patient, the Fused Tetracycle Derivatives can be administered as a component of a composition that comprises a pharmaceutically acceptable carrier or vehicle. The present invention provides pharmaceutical compositions comprising an effective amount of at least one Fused Tetracycle Derivative and a pharmaceutically acceptable carrier. In the pharmaceutical compositions and methods of the present invention, the active ingredients will typically be administered in admixture with suitable carrier materials suitably selected with respect to the intended form of administration, i.e., oral tablets, capsules (either solid-filled, semi-solid filled or liquid filled), powders for constitution, oral gels, elixirs, dispersible granules, syrups, suspensions, and the like, and consistent with conventional pharmaceutical practices. For example, for oral administration in the form of tablets or capsules, the active drug component may be combined with any oral non-toxic pharmaceutically acceptable inert carrier, such as lactose, starch, sucrose, cellulose, magnesium stearate, dicalcium phosphate, calcium sulfate, talc, mannitol, ethyl alcohol (liquid forms) and the like. Solid form preparations include powders, tablets, dispersible granules, capsules, cachets and suppositories. Powders and tablets may be comprised of from about 0.5 to about 95 percent inventive composition. Tablets, powders, cachets and capsules can be used as solid dosage forms suitable for oral administration.

Moreover, when desired or needed, suitable binders, lubricants, disintegrating agents and coloring agents may also be incorporated in the mixture. Suitable binders include starch, gelatin, natural sugars, corn sweeteners, natural and synthetic gums such as acacia, sodium alginate, carboxymethylcellulose, polyethylene glycol and waxes. Among the lubricants there may be mentioned for use in these dosage forms, boric acid, sodium benzoate, sodium acetate, sodium chloride, and the like. Disintegrants include starch, methylcellulose, guar gum, and the like. Sweetening and flavoring agents and preservatives may also be included where appropriate.

Liquid form preparations include solutions, suspensions and emulsions and may include water or water-propylene glycol solutions for parenteral injection.

Liquid form preparations may also include solutions for intranasal administration.

Aerosol preparations suitable for inhalation may include solutions and solids in powder form, which may be in combination with a pharmaceutically acceptable carrier, such as an inert compressed gas.

Also included are solid form preparations which are intended to be converted, shortly before use, to liquid form preparations for either oral or parenteral administration. Such liquid forms include solutions, suspensions and emulsions.

For preparing suppositories, a low melting wax such as a mixture of fatty acid glycerides or cocoa butter is first melted, and the active ingredient is dispersed homogeneously therein as by stirring. The molten homogeneous mixture is then poured into convenient sized molds, allowed to cool and thereby solidify.

Additionally, the compositions of the present invention may be formulated in sustained release form to provide the rate controlled release of any one or more of the components or active ingredients to optimize therapeutic effects, i.e., antiviral activity and the like. Suitable dosage forms for sustained release include layered tablets containing layers of varying disintegration rates or controlled release polymeric matrices impregnated with the active components and shaped in tablet form or capsules containing such impregnated or encapsulated porous polymeric matrices.

In one embodiment, the one or more Fused Tetracycle Derivatives are administered orally.

In another embodiment, the one or more Fused Tetracycle Derivatives are administered intravenously.

In another embodiment, the one or more Fused Tetracycle Derivatives are administered topically.

In still another embodiment, the one or more Fused Tetracycle Derivatives are administered sublingually.

In one embodiment, a pharmaceutical preparation comprising at least one Fused Tetracycle Derivative is in unit dosage form. In such form, the preparation is subdivided into unit doses containing effective amounts of the active components.

Compositions can be prepared according to conventional mixing, granulating or coating methods, respectively, and the present compositions can contain, in one embodiment, from about 0.1% to about 99% of the Fused Tetracycle Derivative (s) by weight or volume. In various embodiments, the present compositions can contain, in one embodiment, from about 1% to about 70% or from about 5% to about 60% of the Fused Tetracycle Derivative(s) by weight or volume.

The quantity of Fused Tetracycle Derivative in a unit dose of preparation may be varied or adjusted from about 1 mg to about 2500 mg. In various embodiment, the quantity is from about 10 mg to about 1000 mg, 1 mg to about 500 mg, 1 mg to about 100 mg, and 1 mg to about 100 mg.

For convenience, the total daily dosage may be divided and administered in portions during the day if desired. In one embodiment, the daily dosage is administered in one portion. In another embodiment, the total daily dosage is administered in two divided doses over a 24 hour period. In another embodiment, the total daily dosage is administered in three divided doses over a 24 hour period. In still another embodiment, the total daily dosage is administered in four divided doses over a 24 hour period.

The amount and frequency of administration of the Fused Tetracycle Derivatives will be regulated according to the judgment of the attending clinician considering such factors as age, condition and size of the patient as well as severity of the symptoms being treated. Generally, a total daily dosage of the Fused Tetracycle Derivatives range from about 0.1 to about 2000 mg per day, although variations will necessarily occur depending on the target of therapy, the patient and the route of administration. In one embodiment, the dosage is from about 1 to about 200 mg/day, administered in a single dose or in 2-4 divided doses. In another embodiment, the dosage is from about 10 to about 2000 mg/day, administered in a single dose or in 2-4 divided doses. In another embodiment, the dosage is from about 100 to about 2000 mg/day, administered in a single dose or in 2-4 divided doses. In still another embodiment, the dosage is from about 500 to about 2000 mg/day, administered in a single dose or in 2-4 divided doses.

The compositions of the invention can further comprise one or more additional therapeutic agents, selected from those listed above herein. Accordingly, in one embodiment, the present invention provides compositions comprising: (i) at least one Fused Tetracycle Derivative or a pharmaceutically acceptable salt thereof; (ii) one or more additional therapeutic agents that are not a Fused Tetracycle Derivative; and (iii) a pharmaceutically acceptable carrier, wherein the amounts in the composition are together effective to treat HCV infection.

In one embodiment, the present invention provides compositions comprising a Compound of Formula (I) or (II) and a pharmaceutically acceptable carrier.

In another embodiment, the present invention provides compositions comprising a Compound of Formula (I) or (II), a pharmaceutically acceptable carrier, and a second therapeutic agent selected from the group consisting of HCV antiviral agents, immunomodulators, and anti-infective agents.

In another embodiment, the present invention provides compositions comprising a Compound of Formula (I) or (II), a pharmaceutically acceptable carrier, and two additional therapeutic agents, each of which are independently selected from the group consisting of HCV antiviral agents, immunomodulators, and anti-infective agents.

Kits

In one aspect, the present invention provides a kit comprising a therapeutically effective amount of at least one Fused Tetracycle Derivative, or a pharmaceutically acceptable salt, solvate, ester or prodrug of said compound and a pharmaceutically acceptable carrier, vehicle or diluent.

In another aspect the present invention provides a kit comprising an amount of at least one Fused Tetracycle Derivative, or a pharmaceutically acceptable salt, solvate, ester or prodrug of said compound and an amount of at least one additional therapeutic agent listed above, wherein the amounts of the two or more active ingredients result in a desired therapeutic effect. In one embodiment, the one or more Fused Tetracycle Derivatives and the one or more additional therapeutic agents are provided in the same container. In one embodiment, the one or more Fused Tetracycle Derivatives and the one or more additional therapeutic agents are provided in separate containers.

EXAMPLES

General Methods

Solvents, reagents, and intermediates that are commercially available were used as received. Reagents and intermediates that are not commercially available were prepared in the manner as described below. $^1$H NMR spectra were obtained on either a Varian VNMR System 400 (400 MHz) or a Bruker Avance 500 (500 MHz) and are reported as ppm downfield from Me$_4$Si with number of protons, multiplicities, and coupling constants in Hertz indicated parenthetically. Where LC/MS data are presented, analyses was performed using an Agilent 6110A MSD or an Applied Biosystems API-100 mass spectrometer and Shimadzu SCL-10A LC column: Altech platinum C18, 3 micron, 33 mm×7 mm ID; gradient flow: 0 minutes—10% CH$_3$CN, 5 minutes—95% CH$_3$CN, 5-7 minutes—95% CH$_3$CN, 7 minutes—stop. The retention time and observed parent ion are given. Flash column chromatography was performed using pre-packed normal phase silica from Biotage, Inc. or bulk silica from Fisher Scientific. Unless otherwise indicated, column chromatography was performed using a gradient elution of hexanes/ethyl acetate, from 100% hexanes to 100% ethyl acetate.

Example 1

Preparation of Intermediate Compound Int-1a

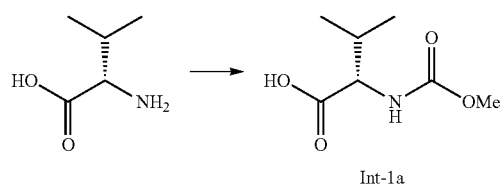

To a solution of L-valine (10.0 g, 85.3 mmol) in 1M aqueous NaOH solution (86 mL) at room temperature was added solid sodium carbonate (4.60 g, 43.4 mmol). The reaction mixture was cooled to 0° C. (ice bath) and then methyl chloroformate (7.20 mL, 93.6 mmol) was added dropwise over 20 minutes. The reaction mixture was then allowed to warm to room temperature, and allowed to stir at room temperature for an additional 4 hours. The reaction mixture was then diluted with diethyl ether (100 mL), the resulting solution was cooled to at 0° C., and then concentrated hydrochloric acid (18 mL, 216 mmol) was added slowly. The reaction was extracted with EtOAc (3×100 mL) and the combined organics were dried over MgSO$_4$, filtered and concentrated in vacuo to provide Int-1a (13.5 g, 90%), which was used without further purification.

The following intermediates can be prepared by the reaction of L-valine with isopropyl chloroformate, 2-methoxyethyl chloroformate or with 1-methylcyclopropyl hydroxysuccinimide respectively as above.

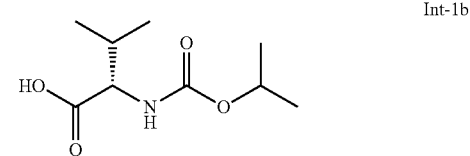

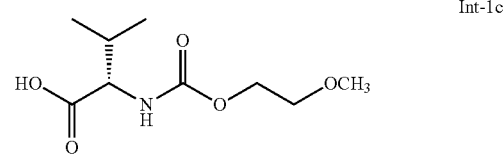

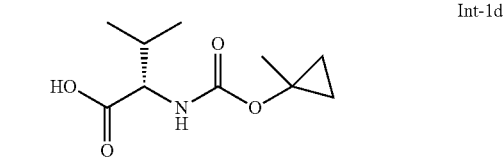

Example 2

Preparation of Intermediate Compound Int-2a

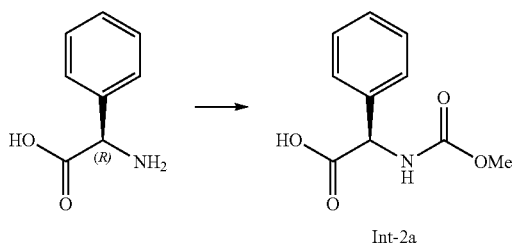

To a solution of D-phenylglycine (10.0 g, 66.1 mmol) and NaOH (21.2 g, 265 mmol) in water (60 mL) at 0° C. was added methyl chloroformate (10.2 mL, 133 mmol) dropwise over 20 minutes. The resulting mixture was allowed to stir at 0° C. for 1 hour, then was acidified using concentrated hydrochloric acid (25 mL, 300 mmol). The acidic solution was extracted with EtOAc (3×100 mL) and the combined organics were dried over MgSO$_4$, filtered and concentrated in vacuo to provide Int-2a (12.6 g, 91%), which was used without further purification.

The following intermediates can be prepared by the reaction of glycine, L-Alanine and 4-F phenylglycine respectively with methyl chloroformate (Aldrich Inc.) using the method described above:

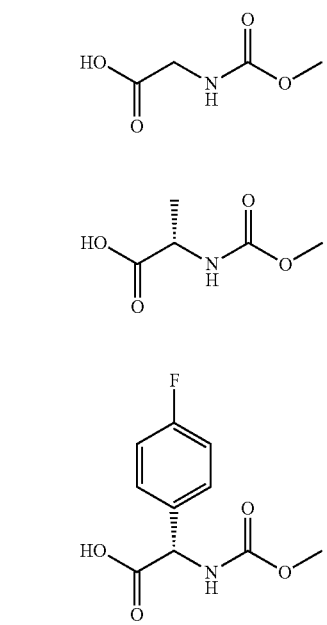

Example 3

Preparation of Intermediate Compound Int-3a

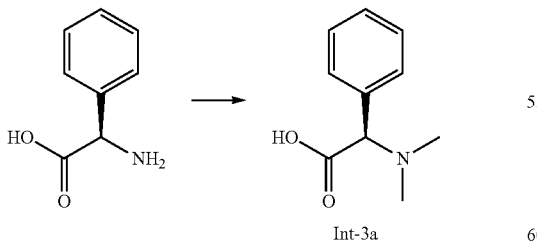

A solution of D-phenylglycine (20.0 g, 132 mmol), 37% aqueous formaldehyde (66 mL, 814 mmol) and 5% Pd on carbon (8.0 g, mmol) in a mixture of methanol (80 mL) and 1 N HCl (60 mL) was placed on a hydrogenation shaker and shook under an atmosphere of 35-40 psi hydrogen for 4 hours. The reaction was then flushed with nitrogen, filtered through a celite pad and concentrated in vacuo to provide Compound Int-3a (29.7 g, quant.) as a white solid, which was used without further purification.

Example 4

Preparation of Intermediate Compound Int-4f

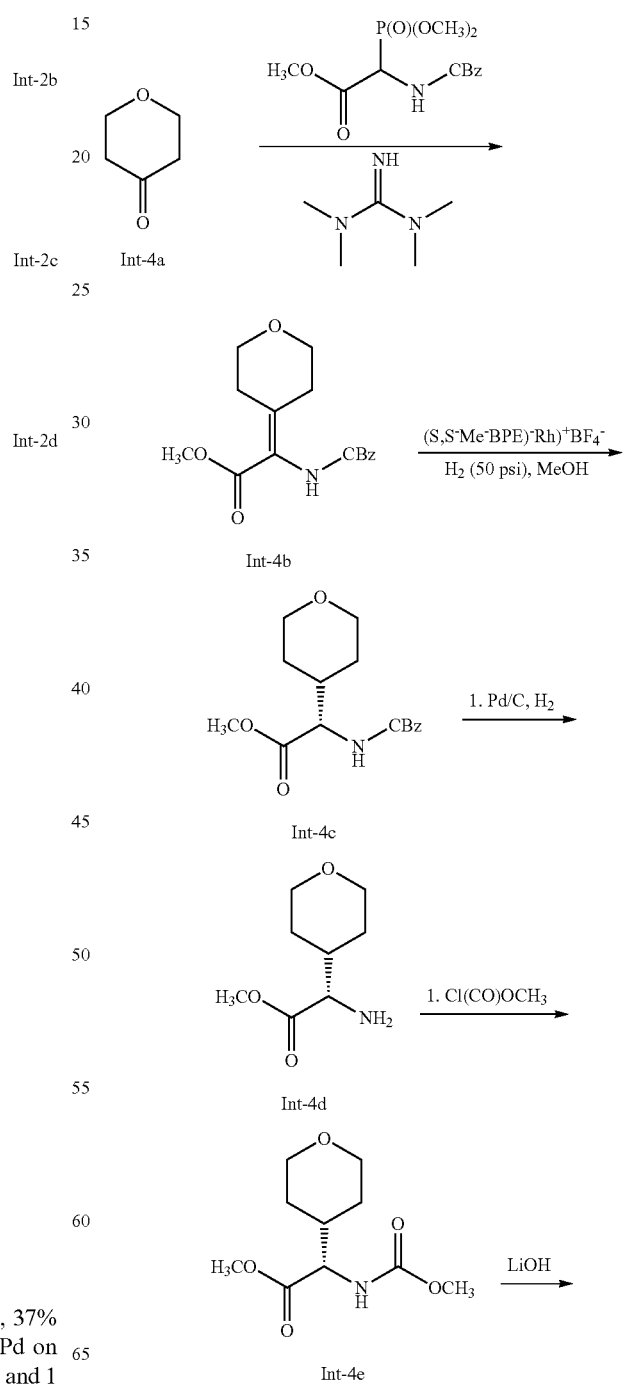

-continued

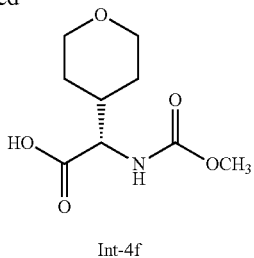

Int-4f

Step A—Preparation of Compound Int-4b

To a solution of methyl 2-(benzyloxycarbonylamino)-2-(dimethoxyphosphoryl)acetate (10.0 g, 30.2 mmol, made as described in Hamada et al., *Organic Letters*; English, 20:4664-4667 (2009)) in THF (100 mL) at −20° C. was added tetramethylguanidine (4.20 mL, 33.2 mmol). The reaction mixture was allowed to stir at −20° C. for 1 hour then dihydro-2H-pyran-4(3H)-one (4a) was added (3.1 mL, 33.2 mmol) in THF (5 mL) and the reaction mixture was warmed to room temperature and allowed to stir for about 15 hours. EtOAc (200 mL) was added and the organic mixture was washed with water (3×50 mL) and brine (50 mL). The organic layers were combined and dried with $Na_2SO_4$, filtered and concentrated in vacuo. The crude product was purified using flash chromatography on an ISCO 330 g Redi-Sep column using 0-35% EtOAc/hexanes as the eluent to provide Compound Int-4b as a white solid (615 mg, 45%). $^1$H NMR ($CDCl_3$) δ 7.40-7.30 (m, 5H), 6.00 (br s, 1H), 5.12 (s, 2H), 3.80-3.65 (m, 7H), 2.92 (m, 2H), 2.52-2.48 (m, 2H).

Step B—Preparation of Compound Int-4c

To a solution of Int-4b (2.43 g, 7.96 mmol) in methanol (160 mL) previously purged with $N_2$ was added (−)-1,2-Bis((2S,5S)-2,5-dimethylphospholano) ethane (cyclooctadiene) rhodium(I) tetrafluoroborate (487 mg, 0.880 mmol) under $N_2$. The mixture was shaken in a Parr shaker apparatus for 18 hours at 50 psi of $H_2$. After evacuating the hydrogen, the suspension was filtered and the filtrate was concentrated in vacuo to provide Compound Int-4c as a white solid (1.30 g, 53%). $^1$H NMR ($CDCl_3$) δ 7.40-7.30 (m, 5H), 5.32 (br s, 1H), 5.12 (s, 2H), 4.40-4.30 (m, 1H), 4.00-3.95 (m, 2H), 3.75 (s, 3H), 3.40-3.25 (m, 2H), 2.10-1.95 (m, 1H), 1.50-1.45 (m, 4H).

Step C—Preparation of Compound Int-4d

To a suspension of 50% palladium on carbon (10% wet, 200 mg) in absolute ethanol (20 mL) under nitrogen was added Int-4c (1.06 g, 3.45 mmol). With stirring, the solution was placed in vacuo for 30 seconds and then was opened to a hydrogen gas balloon for 2 hours. After evacuating the hydrogen, the suspension was filtered through a Celite pad and the pad washed with ethanol (2×20 mL). The filtrate was concentrated in vacuo to provide Compound Int-4d as a colorless oil (585 mg, 98%). $^1$H NMR ($CDCl_3$) δ 4.06-3.96 (m, 2H), 3.73 (s, 3H), 3.48-3.28 (m, 3H), 1.92-1.78 (m, 1H), 1.61-1.47 (m, 6H).

Step D—Preparation of Compound Int-4e

To the solution of Compound Int-4d (585 mg, 3.37 mmol) and triethylamine (0.710 mL, 5.09 mmol) in $CH_2Cl_2$ (6 mL) was added methyl chloroformate (0.290 mL, 3.76 mmol). The reaction mixture was allowed to stir at room temperature for about 15 hours. Water (15 mL) was added and the aqueous mixture was extracted with $CH_2Cl_2$ (3×20 mL). The combined organic layers were dried over $Na_2SO_4$, filtered and concentrated in vacuo. The crude product was purified using flash chromatography on an ISCO 24 g Redi-Sep column using 0-3% MeOH/$CH_2Cl_2$ as the eluent to provide Compound Int-4e as a colorless oil (600 mg, 77%). $^1$H NMR ($CDCl_3$) δ 5.27-5.18 (m, 1H), 4.38-4.28 (m, 1H), 4.06-3.96 (m, 2H), 3.75 (s, 3H), 3.69 (s, 3H), 3.39-3.30 (m, 2H), 2.09-1.94 (m, 1H), 1.59-1.48 (m, 4H).

Step E—Preparation of Compound Int-4f

To the solution of Compound Int-4e (600 mg, 2.59 mmol) in THF (5 mL) was added lithium hydroxide monohydrate (218 mg, 5.19 mmol) in water (5 mL). The reaction mixture was allowed to stir at room temperature for 2 hours then concentrated in vacuo to half volume. The aqueous mixture was then acidified with 6N HCl and extracted with EtOAc (7×50 mL). The combined organic layers were dried over $Na_2SO_4$, filtered and concentrated in vacuo to provide Compound Int-4f as an off-white solid (485 mg, 86%). $^1$H NMR ($CD_3OD$) δ 4.09-4.07 (m, 1H), 3.96-3.92 (m, 2H), 3.65 (s, 3H), 3.40-3.34 (m, 2H), 2.10-1.99 (m, 1H), 1.56-1.47 (m, 4H).

Example 5

Preparation of Intermediate Compound Int-5f

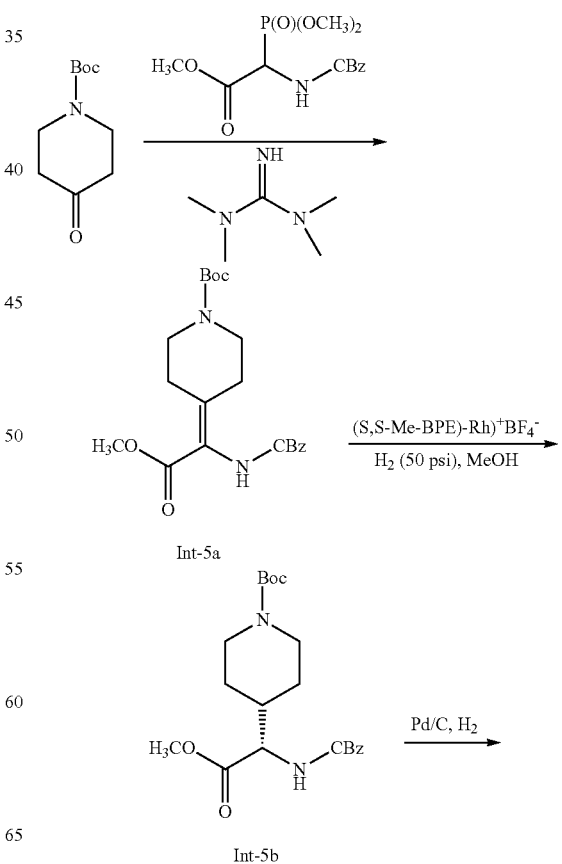

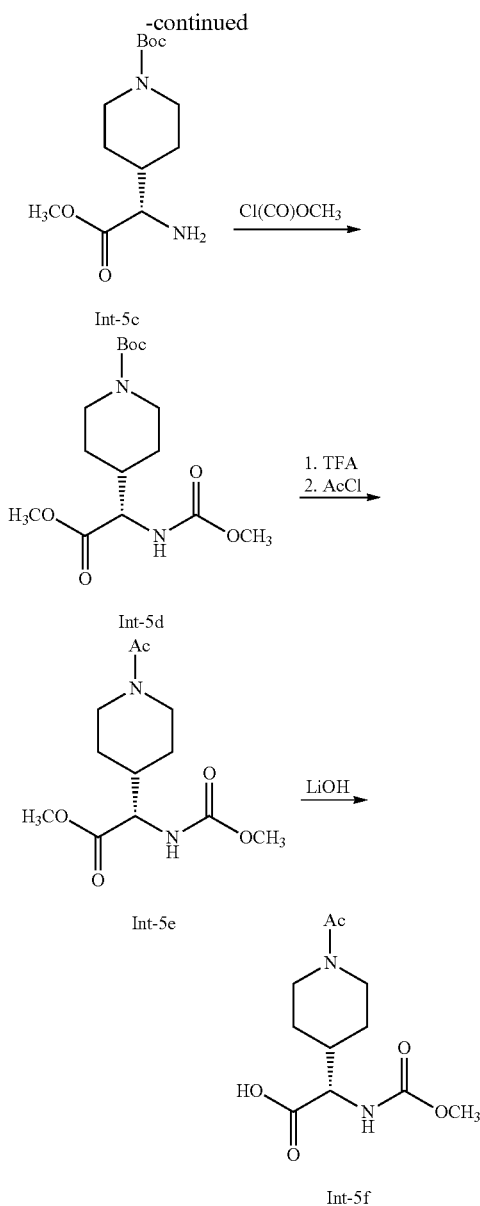

Step A—Preparation of Compound Int-5a

To a solution of methyl 2-(benzyloxycarbonylamino)-2-(dimethoxyphosphoryl)acetate (1.50 g, 4.52 mmol) in THF (5 mL) at −20° C. was added tetramethylguanidine (625 μL, 4.98 mmol). The reaction mixture was allowed to stir at −20° C. for 1 hour then text-butyl 4-oxopiperidine-1-carboxylate was added (992 mg, 4.97 mmol) in THF (2 mL) and the reaction mixture was warmed to room temperature and allowed to stir for about 15 hours. EtOAc (90 mL) was added and the organic mixture was washed with water (3×20 mL) and brine (25 mL). The combined organic layers were dried over $Na_2SO_4$, filtered and concentrated in vacuo. The crude product was purified using flash chromatography on an ISCO 40 g Redi-Sep column using 0-35% EtOAc/hexanes as the eluent to provide Compound Int-5a as a white semi-solid (1.1 g, 61%). $^1$H NMR ($CDCl_3$) δ 7.40-730 (m, 5H), 6.02 (br s, 1H), 5.12 (s, 2H), 3.80-3.40 (m, 7H), 2.90-2.80 (m, 2H), 2.45-2.35 (m, 2H), 1.45 (s, 9H).

Step B—Preparation of Compound Int-5b

To a solution of Int-5a (1.30 g, 3.21 mmol) in methanol (90 mL) previously purged with $N_2$ was added (−)-1,2-Bis((2S,5S)-2,5-dimethylphospholano) ethane(cyclooctadiene)rhodium(I) tetrafluoroborate (197 mg, 0.354 mmol) under $N_2$. The mixture was then shaken in a Parr shaker apparatus for 18 hours at 50 psi of $H_2$. After evacuating the hydrogen, the suspension was filtered and the filtrate was concentrated in vacuo to provide Compound Int-5b as colorless oil (1.00 g, 77%). $^1$H NMR ($CDCl_3$) δ 7.40-7.30 (m, 5H), 5.35-5.25 (m, 1H), 5.10 (s, 2H), 4.40-4.35 (m, 1H), 4.20-4.10 (m, 2H), 3.70 (s, 3H), 2.70-2.55 (m, 2H), 2.00-1.90 (m, 1H), 1.65-1.40 (m, 1H), 1.30-1.20 (m, 2H).

Step C—Preparation of Compound Int-5c

To a solution of 50% palladium on carbon (10% wet, 250 mg) in absolute ethanol (20 mL) under nitrogen was added Int-5b (1.00 g, 2.46 mmol). The reaction was evacuated, then put under an $H_2$ atmosphere using a hydrogen-filled balloon and allowed to stir for 2 hours. The hydrogen was evacuated and the resulting suspension was filtered through a Celite pad and the pad washed with ethanol (2×20 mL). The filtrate and ethanol washings were combined and concentrated in vacuo to provide Compound Int-5c as a colorless oil (670 mg, quant.). $^1$H NMR ($CDCl_3$) δ 4.21-4.08 (m, 2H), 3.73 (s, 3H), 3.31 (d, J=6.0 Hz, 1H), 2.75-2.57 (m, 2H), 1.84-1.70 (m, 1H), 1.68-1.56 (m, 1H), 1.45 (s, 9H), 1.45-1.20 (m, 5H).

Step D—Preparation of Compound Int-5d

To the solution of Compound Int-5c (670 mg, 2.46 mmol) and triethylamine (0.520 mL, 3.73 mmol) in $CH_2Cl_2$ (10 mL) was added methyl chloroformate (0.210 mL, 2.72 mmol). The reaction mixture was allowed to stir at room temperature for about 15 hours. Water (20 mL) was added and the aqueous mixture was extracted with $CH_2Cl_2$ (2×15 mL). The combined organic layers were dried over $Na_2SO_4$, filtered and concentrated in vacuo. The crude product was purified using flash chromatography on an ISCO 24 g Redi-Sep column using 0-3% $MeOH/CH_2Cl_2$ as the eluent to provide Compound Int-5d as an off-white solid (515 mg, 63%). $^1$H NMR ($CDCl_3$) δ 5.26-5.17 (m, 1H), 4.38-4.30 (m, 1H), 4.20-4.07 (m, 2H), 3.75 (s, 3H), 3.68 (s, 3H), 2.71-2.57 (m, 2H), 2.00-1.85 (m, 1H), 1.87-1.48 (m, 2H), 1.44 (s, 9H), 1.35-1.18 (m, 2H).

Step E—Preparation of Compound Int-5e

Compound Int-5d (300 mg, 0.908 mmol) was dissolved in a mixture of TFA (2 mL) and $CH_2Cl_2$ (10 mL) and the solution was allowed to stir at room temperature for 1 hour, then was concentrated in vacuo. To the resulting residue was added triethylamine (0.760 mL, 5.45 mmol) in $CH_2Cl_2$ (10 mL), then acetic anhydride (0.086 mL, 0.915 mmol). The reaction was allowed to stir at room temperature for about 15 hours then concentrated in vacuo. The residue obtained was purified using flash chromatography on an ISCO 12 g Redi-Sep column using 0-4% $MeOH/CH_2Cl_2$ as the eluent to provide Compound Int-5e as colorless oil (247 mg, 99%). $^1$H NMR ($CDCl_3$) δ 5.27-5.21 (m, 1H), 4.73-4.62 (m, 1H), 4.42-4.32 (m, 1H), 3.69 (s, 3H), 3.18 (s, 3H), 3.18-3.09 (m, 1H), 3.07-2.95 (m, 1H), 2.55-2.41 (m, 1H), 2.07 (s, 3H), 1.78-1.49 (m, 3H), 1.38-1.21 (m, 2H).

Step F—Preparation of Compound Int-5f

To the solution of Compound Int-5e (247 mg, 2.59 mmol) in THF (3 mL) was added lithium hydroxide monohydrate (77 mg, 1.83 mmol) in water (3 mL). The reaction mixture was allowed to stir at room temperature for about 15 hours then concentrated in vacuo to 50% of its original volume. The concentrated solution was then acidified with 1N HCl to pH 4 and extracted with EtOAc (7×15 mL). The combined organic extracts were dried over Na₂SO₄, filtered and concentrated in vacuo to provide Compound Int-5f as an off-white solid (106 mg, 45%). ¹H NMR (CD₃OD) δ 5.52-5.43 (m, 1H), 4.71-4.62 (m, 1H), 4.4-4.31 (m, 1H), 3.91-3.81 (M, 1H), 3.70 (s, 3H), 3.12-2.99 (m, 1H), 2.58-2.46 (m, 1H), 2.10 (m, 4H), 1.86-1.54 (m, 2H), 1.50-1.21 (m, 3H).

Example 6

Preparation of Intermediate Compound Int-6f

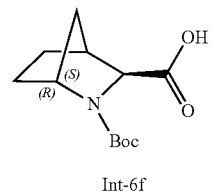

Int-6f

Step A—Preparation of Compound Int-6c

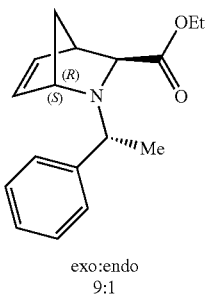

Int-6c exo:endo
9:1

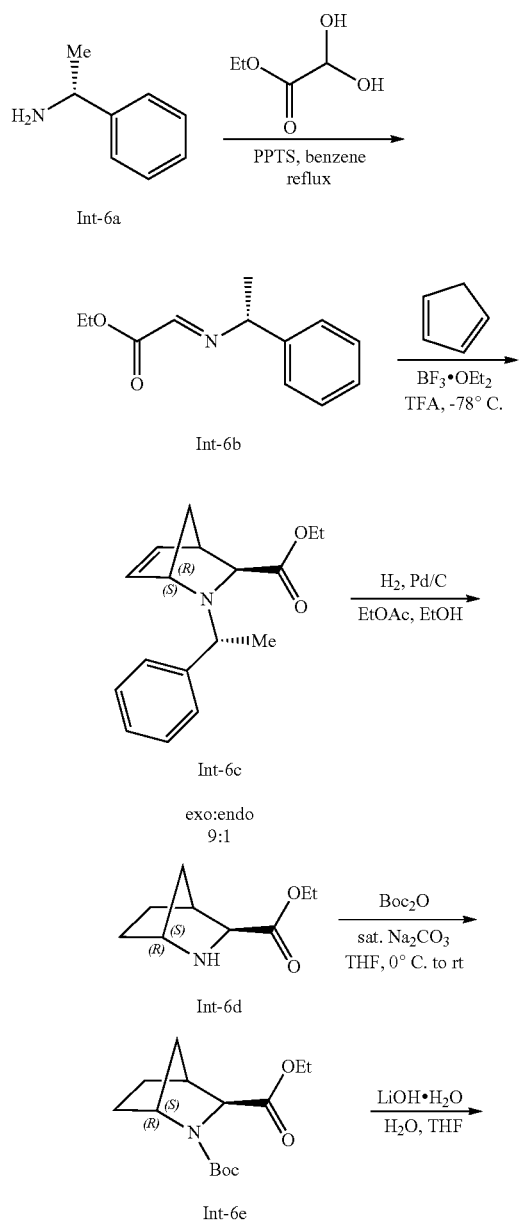

A stirred mixture of D-(+)-α-methylbenzyl amine Int-6a (50.0 g, 0.412 mol), ethyl glyoxylate (81.5 mL, 50% in toluene, 0.412 mol) and PPTS (0.50 g, 2.00 mmol) in benzene (600 mL) was heated to reflux in a Dean-Stark apparatus and allowed to remain at reflux until no further water (~8 mL) azeotroped from the reaction (~4 hours). The resulting mixture was concentrated in vacuo to provide Compound Int-6b, which was used without further purification: ¹H NMR (300 MHz, CDCl₃) δ 7.72 (s, 1H), 7.36-7.24 (m, 5H), 4.61 (q, J=6.9 Hz, 1H), 4.35 (q, J=7.2 Hz, 2H), 1.62 (d, J=6.6 Hz, 3H), 1.34 (t, J=7.2 Hz, 3H).

To a stirred solution of crude Int-6b in methylene chloride (600 mL) at −78° C. were added the following in 10 minute intervals: TFA (31.0 mL, 0.416 mol), boron trifluoride etherate (51.3 mL, 0.416 mol) and freshly distilled cyclopentadiene (32.7 g, 0.494 mol). After less than 2 minutes following the addition of cyclopentadiene, the reaction mixture formed a thick brown mass, which was allowed to stir for 6 hours at −78° C. The reaction mixture was then allowed to warm to room temperature on its own and stir for an additional 15 hours. The resulting dark brown reaction mixture was quenched with sat. aq. Na₂CO₃ (~900 mL) and allowed to stir for 30 minutes. The resultant suspension was filtered through a pad of Celite® and the filtrate was extracted with methylene chloride (3×100 mL). The combined organic extracts were washed with sat. aq. NaCl (2×75 mL), dried over Na₂SO₄, filtered and concentrated in vacuo. The residue obtained was purified using flash column chromatography (silica; 8×18 cm, 10% to 25% ethyl acetate/hexanes as the eluent) to provide endo Int-6c (10.9 g, 9%) as a brown oil: ¹H NMR (300 MHz, CDCl₃) δ 7.34-7.19 (m, 5H), 6.00-5.95 (m, 1H), 4.18 (q, J=7.1 Hz, 3H), 3.47 (s, 1H), 3.03 (s, 1H), 2.97 (q, J=6.5 Hz, 1H), 2.41 (s, 1H), 1.86 (d, J=8.2 Hz, 1H), 1.26 (t, J=6.6 Hz, 3H), 1.17 (t, J=6.6 Hz, 3H). Exo Int-6c (84.3 g, 74%) was also collected as a brown oil: ¹H NMR (300 MHz, CDCl₃) δ 7.34-7.19 (m, 5H), 6.36-6.33 (m, 1H), 6.22-6.18 (m, 1H), 4.37 (s, 1H), 3.87 (q, J=6.8 Hz, 2H), 3.10 (q, J=6.5 Hz, 1H), 2.96 (s, 1H), 2.27 (s, 1H), 2.20 (d, J=8.4 Hz, 1H), 1.48 (d, J=6.5 Hz, 3H), 1.01 (d, J=7.0 Hz, 3H), 1.00 (m, 1H).

Step B—Representative Example for the Preparation of Compound Int-6d

A mixture of exo-Int-6c (15.8 g, 0.582 mol) and 10% Pd/C (4.07 g, 50% wet) in a 1:2 mixture of EtOH/EtOAc (150 mL) was shaken for 23 hours in a Parr hydrogenation apparatus under an atmosphere of H$_2$ (50 psi). The reaction mixture was then filtered through Celite® and the filtrate was concentrated in vacuo. $^1$H NMR analysis of the residue (10.8 g) showed some aromatic resonances present. Repetition of the hydrogenation procedure using 10% Pd/C (2.0 g) afforded Int-6d (10.0 g, quant.) as a brown oil, which was used without further purification. $^1$H NMR (300 MHz, CDCl$_3$) δ 4.18 (q, J=7.2 Hz, 3H), 3.54 (s, 1H), 3.32 (s, 1H), 2.62 (s, 1H), 2.23 (s, 1H), 1.64-1.39 (m, 5H), 1.31-1.20 (m, 4H).

Step C—Preparation of Compound Int-6e

To a solution of Int-6d (36.6 g, 0.236 mol) and sat. aq. Na$_2$CO$_3$ (300 mL) in THF (600 mL) at 0° C. was added di-tert-butyl dicarbonate (59.0 g, 0.270 mol). The resulting reaction was allowed to slowly warm to room temperature with stirring over 6 hours, then was allowed to stir at room temperature for an additional 68 hours. The reaction mixture was diluted with EtOAc (250 mL) and water (250 mL) and the aqueous layer was extracted with EtOAc (2×200 mL). The combined organic extracts were washed with sat. aq. NaCl (2×75 mL), dried over Na$_2$SO$_4$, filtered and concentrated in vacuo. The residue obtained was purified using flash column chromatography (silica; 16×10 cm) using 10-20% ethyl acetate/hexanes as the eluent to provide Int-6e (49.0 g, 84%) as a pale yellow oil: $^1$H NMR (300 MHz, CDCl$_3$) δ 4.35 (s, 0.6H), 4.22-4.10 (m, 2.4H), 3.81 (s, 0.45H), 3.71 (s, 0.55H), 2.66 (s, 1H), 1.96-1.90 (m, 1H), 1.76-1.50 (m, 3H), 1.55-1.45 (m, 5H), 1.39 (s, 5H), 1.30-1.23 (m, 4H).

Step D—Preparation of Compound 2.2.1 Bicyclic Acid Intermediate Int-6f

To a stirred mixture of Int-6e (49.0 g, 0.182 mmol) in 1:1 THF/water (600 mL) was added LiOH.H$_2$O (15.3 g, 0.364 mol). The reaction mixture was heated to 60° C. and allowed to stir at this temperature for 47 hours. The reaction mixture was then cooled to room temperature, concentrated in vacuo, and the residue obtained was diluted with CH$_2$Cl$_2$ (200 mL) then acidified with 2N HCl to pH ~4. The acidic solution was extracted with CH$_2$Cl$_2$ (4×100 mL) and the combined organic extracts were washed with sat. aq. NaCl (25 mL), dried over Na$_2$SO$_4$, filtered and concentrated in vacuo to provide Int-6f, (1R,3S,4S)—N-Boc-2-azabicyclo[2.2.1]heptane-3-carboxylic acid (41.2 g, 93%) as an off white solid, which was used without further purification: $^1$H NMR (400 MHz, DMSO-d$_6$) δ 12.44 (s, 1H), 4.13 (s, 0.56H), 4.06 (s, 0.47H), 3.61 (d, J=4.0 Hz, 1H), 2.59 (s, 1H), 1.75-1.45 (m, 5H), 1.39 (s, 4H), 1.32 (s, 5H), 1.23 (t, J=8.4 Hz, 1H); Optical Rotation: [α]$_{25}^D$ -169.0° (c=1.1, CHCl$_3$).

Example 7

Preparation of Intermediate Compound Int-7h

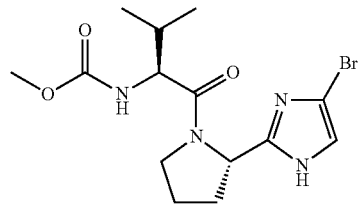

Int-7h

Step A—Preparation of Compound Int-7b

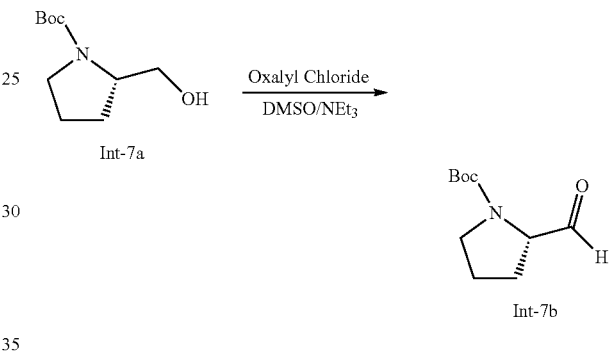

A 2 L, 3-necked round bottomed flask equipped with an overhead stirrer and a N$_2$ inlet was charged with a solution of oxalyl chloride (130 mL, 0.26 mol) in dichloromethane (250 mL). The solution was cooled to -78° C., and a solution of DMSO (20 mL, 0.28 mol) in dichloromethane (30 mL) was added dropwise. After 30 minutes, a solution of (S)—N-Boc-prolinol, Int-7a (40 g, 0.20 mol) in dichloromethane (200 mL) was added dropwise. After 30 minutes, triethylamine (140 mL, 1.00 mol) was added to the solution, and the flask was transferred to an ice/water bath and allowed to stir for another 30 minutes. The reaction mixture was diluted with dichloromethane (200 mL) and washed successively with H$_2$O, 1M HCl, saturated NaHCO$_3$, and brine. The organic layer was dried over Na$_2$SO$_4$, filtered, and concentrated in vacuo to provide crude (S)-2-formyl-pyrrolidine-1-carboxylic acid tort-butyl ester, Int-7b (40 g) as oil, which was used without further purification.

Step B—Preparation of Compound Int-7c

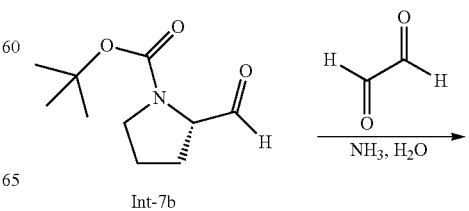

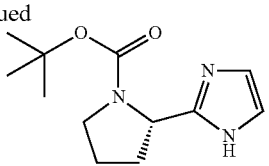

Int-7c

To (S)-Boc-prolinal, Int-7b (crude, 80 g, 0.4 mol) was added a solution of ammonia in MeOH (prepared from 150 mL of 7 N ammonia/MeOH and 200 mL MeOH, 1.05 mol, 260 mol %). An exotherm was noted with the internal temperature rising to ~30° C. The solution was allowed to stir for 0.5 hours at ambient temperature, then glyoxal (76 g, 0.52 mol, 130 mole %) was added over 5 minutes in portions, with the internal temperature rising to ~60° C. and then returning to room temperature after 1 hour. The reaction was allowed to stir for an additional 15 hours and the reaction mixture was concentrated in vacuo. The resulting residue was diluted with dichloromethane (1 L) and water (0.5 L) were added and the organic phase was washed with water (0.25 L), dried over MgSO$_4$, filtered and concentrated in vacuo. The residue obtained was slurried with warm ethyl acetate (~100 mL) and Hexane (100 mL), then was cooled and filtered. The solid obtained was washed with 30% ethyl acetate/Hexane to provide Int-7c (66.2 g, 70%).

Step C—Preparation of Compound Int-7d

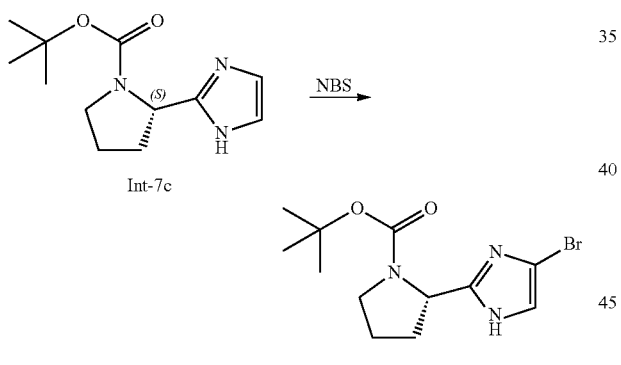

N-Bromosuccinimide (838.4 mg, 4.71 mmol) was added in portions over 15 minutes to a cooled (ice/water) CH$_2$Cl$_2$ (20 mL) solution of imidazole Int-7c (1.06 g, 4.50 mmol). The reaction mixture was allowed to stir for 75 minutes and concentrated in vacuo to oil. The crude product was purified using silica-gel RPLC (Acetonitrile/water/0.1% TFA) to separate the mono bromide from its dibromo analog (over bromination) and the starting material. The RPLC elute was neutralized with excess NH$_3$/MeOH, and the volatile component was removed in vacuo. The residue obtained was partitioned between CH$_2$Cl$_2$ and water, and the aqueous layer was extracted with water. The combined organic phase was dried (MgSO$_4$), filtered, and concentrated in vacuo to provide Compound Int-7d as a white solid (374 mg). $^1$H NMR (DMSO) δ: 12.12 (br s, 1H), 7.10 (m, 1H), 4.70 (m, 1H), 3.31 (m, 1H; overlapped with water signal), 2.25-1.73 (m, 4H), 1.39/1.17 (s, 3.8H+5.2H).

Step D—Alternative Synthesis of Int-7d

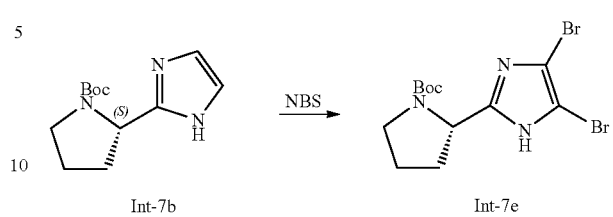

To a suspension of Int-7b (140 g, 0.59 mol) in THF (2000 mL) was added N-bromosuccinimide (200 g, 1.1 mol). The mixture was allowed to stir at ambient temperature under N$_2$ gas for about 15 hours. The solvent was then removed in vacuo, and the residue obtained was purified using silica-gel chromatography (ethyl acetate eluent) to provide 230 g of the desired dibromo compound, Int-7e. MS (ESI) m/e (M+H$^+$): 396.

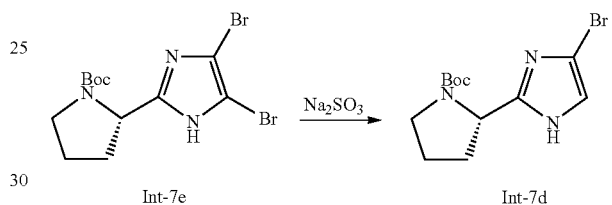

To a suspension of Int-7e (230 g, 0.58 mol) in EtOH/H$_2$O (1:1 ratio, 3000 mL) was added Na$_2$SO$_3$ (733 g, 5.8 mol). The resulting mixture was allowed to stir at mild reflux for about 15 hours. After cooling to room temperature, the mixture was extracted with dichloromethane twice and the combined organic layer was concentrated in vacuo to a semi-solid. The residue obtained was purified using chromatography on silica gel to provide the desired compound, Int-7d. MS (ESI) m/e (M+H$^+$): 317.

Step E—Preparation of Compound Int-7f

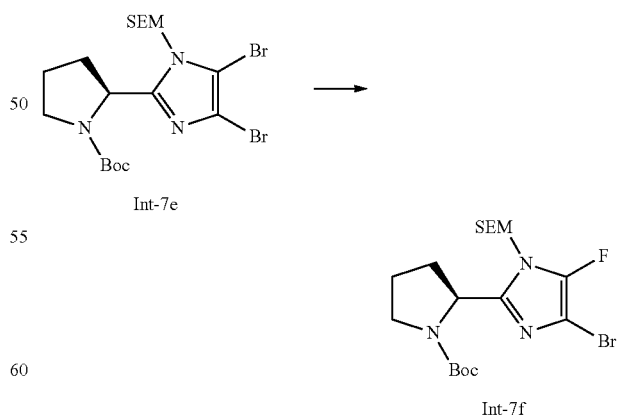

Compound Int-7e (2.63 g, 5.0 mmol) was dissolved in THF (30 mL) and cooled to −78° C., n-BuLi (1M in hexane, 2.2 mL, 5.5 mmol) was added and the reaction was allowed to stir for 20 minutes. N-fluorodibenzenesulfonimide (1.6 mL, 5.0 mmol) was added at −78° C. and the reaction mixture was allowed to warm slowly to room temperature again. The reaction was quenched with aq. NH₄Cl then partitioned between water and ethyl acetate. The organic layer was dried over Na₂SO₄ and concentrated in vacuo. The residue obtained was purified using flash column chromatography (Gradient Ethyl acetate:petroleum ether from 0-20% Ethyl acetate) to provide Int-7f. (63%). MS (ESI) m/z (M+H)⁺: 464, 466. ¹⁹F NMR=−151.8 ppm.

Step F—Preparation of Compound Int-7g

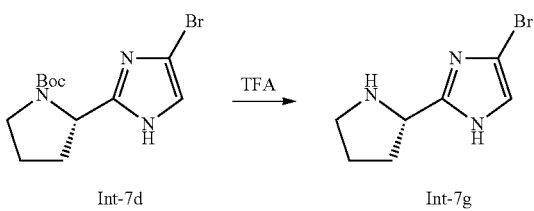 [SMILES: CC(C)(C)OC(=O)N1CCC[C@H]1c1nc(Br)c[nH]1 ; Brc1c[nH]c([C@@H]2CCCN2)n1]

Intermediate 7d (2.51 g, 7.94 mmol, 1.0 eq) was dissolved in 20 mL of CH₂Cl₂ and to the resulting solution was added trifluoroacetic acid (5 mL). The reaction mixture was allowed to stir for about 15 hours at room temperature under N₂, and the reaction was diluted with hexanes (15 mL) and concentrated in vacuo to provide a yellow oil. CH₂Cl₂ and toluene were added and the solution was re-concentrated in vacuo. This step was repeated until excess TFA was removed, giving a solid which was dried under vacuum for 1 hour to provide 3.5 g of solid Int-7g. MS (ESI) m/z (M+H)⁺:217/218.1.

Step G—Preparation of Compound Int-7h

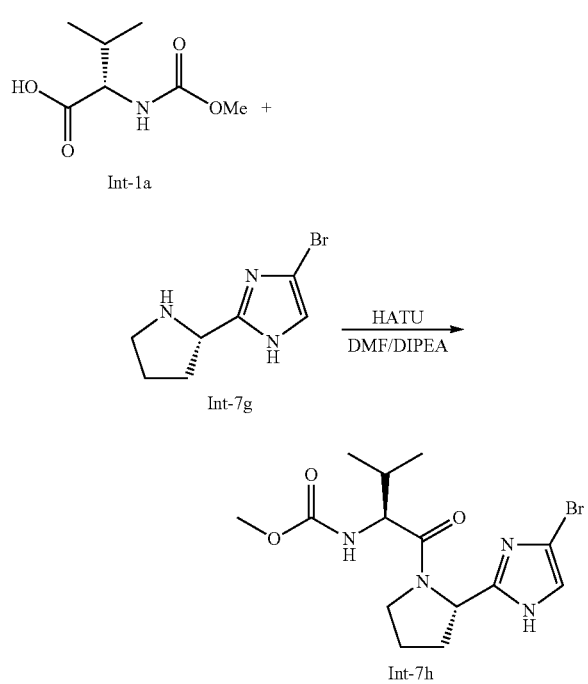

Int-7g (3.01 g, 6.78 mmol, 1.0 eq) and Int-1a (1.202 g, 6.86 mmol, 1.01 eq) were added to a 250 mL round-bottomed flask equipped with a stir bar. DMF was added, and the flask was connected to a vacuum line. The flask was cycled between vacuum and N₂ twice, then cooled in an ice-methanol bath for 10 minutes. HATU (2.75 g, 7.23 mmol, 1.07 eq) was added, followed by diisopropylethyl amine (2.80 mL). The reaction mixture was allowed to stir at −15° C. for 20 minutes. Additional diisopropylethyl amine (2.0 mL) was added. The reaction mixture was allowed to stir for 40 minutes, then quenched with water (1.5 mL). The resulting solution was diluted with EtOAc (100 mL) and Et₂O (100 mL), then washed with water (6×15 mL) and brine (2×25 mL). The organic layer was dried with MgSO₄, filtered, and concentrated in vacuo to dryness yielding 2.23 g of a clear oil. The crude product was purified via chromatography using an 80 g Isco Gold SiO₂ cartridge with a 0.5%-2.5% MeOH/CH₂Cl₂ gradient as the mobile phase. The major peak was collected to provide 1.28 g Int-7h as a white foam. This material was further purified via sgc on an 80 g Isco Gold SiO₂ cartridge using a 45%-65% gradient of (5% methanol in EtOAc)/hexanes. Triethylamine 1% by volume was added to the MeOH/EtOAc solution. The fractions were assayed via TLC using Hanessian's stain. (See Example 13 below for more information on Hanessian's stain.) The major peak was collected as product to provide 1.18 g of Int-7h as a white foam. MS (ESI) m/z (M+H)⁺:373.1.

Example 8

Preparation of Intermediate Compound Int-8h

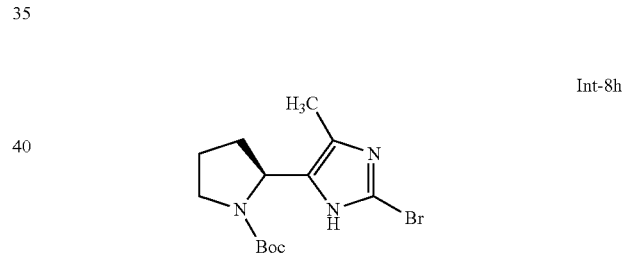

Step A—Preparation of Compound Int-8b

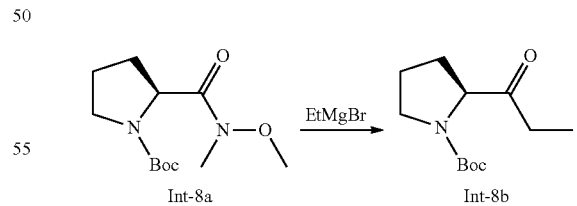

A solution of Int-8a (11.0 g, 42.6 mmol) in THF (50 mL) was cooled to 0° C. and to the cooled solution was added EtMgBr (82 mmol). After addition was complete, the cooling bath was removed and the resulting reaction was allowed to stir at room temperature for 6 hours. 3 N HCl was then added and the reaction mixture was extracted with ethyl acetate (2×50 mL). The combined organic extracts were washed with water, brine, dried over Na₂SO₄, and concentrated in vacuo.

The residue obtained was purified using silica gel chromatography to provide Int-8b (7.5 g, 50%).

Step B—Preparation of Compound Int-8c

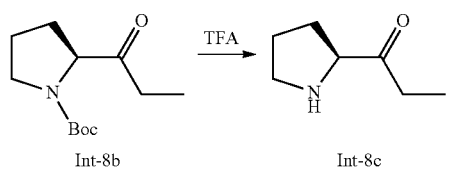

Int-8b (7.5 g, 21.3 mmol) was dissolved in 100 mL of dichloromethane and cooled to 0° C. TFA (100 mL) was added and the reaction was allowed to stir to room temperature over 2 h. The solvent was removed and the residue obtained was redissolved in EtOAc then washed with saturated bicarbonate solution then brine. The extracts were dried over magnesium sulfate, filtered and concentrated in vacuo to provide Compound Int-8c as an oil, which was used without further purification.

Step C—Preparation of Compound Int-8d

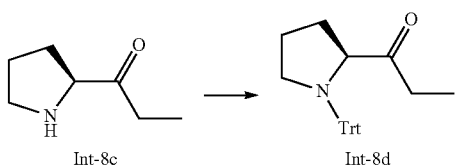

To a solution of Compound Int-8c (4.2 g, 33 mmol) in THF (30 mL) was added $Et_3N$ (4.1 g, 49 mmol) and then trityl chloride (8.7 g, 40 mmol). The mixture was allowed to stir at room temperature for 2 hours, then concentrated in vacuo. The residue obtained was purified using flash chromatography on silica gel to provide Compound Int-8d (8.7 g, 71%). MS (ESI) m/z (M+H)$^+$: 370.

Step D—Preparation of Compound Int-8e

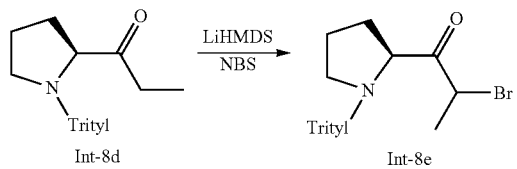

To a solution of Compound Int-8d (3.6 g, 10.0 mmol) in THF (30 mL) was added LiHMDS (11.0 mmol) and then NBS (1.8 g, 10 mmol) at 0° C. The mixture was allowed to stir at room temperature for 2 hours and then 3 N HCl was added to the mixture and the resulting solution was extracted with ethyl acetate (2×25 mL). The combined organic extracts were concentrated in vacuo and the residue obtained was purified using chromatography to provide Compound Int-8e (1.98 g, 44%). MS (ESI) m/z (M+H)$^+$: 478, 480.

Step E—Preparation of Compound Int-8f

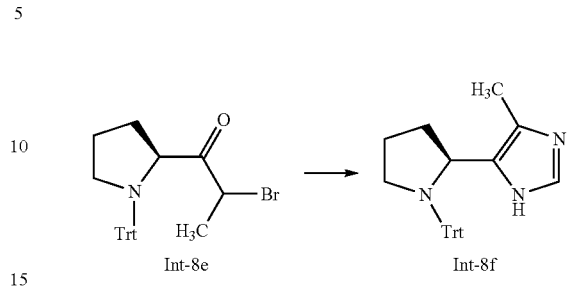

To a solution of Compound Int-8e (3.6 g, 10.0 mmol) in THF (30 mL) was added LiHMDS (11.0 mmol) and then NBS (1.8 g, 10 mmol). The mixture was allowed to stir at room temperature for 2 hours and then 3 N HCl was added to the mixture and extracted with ethyl acetate twice. The organic layer was concentrated in vacuo. The residue obtained was purified using chromatography to provide the Int-8f (1.98 g, 44%). MS (ESI) m/z (M+H)$^+$: 478, 480.

Step F—Preparation of Compound Int-8g

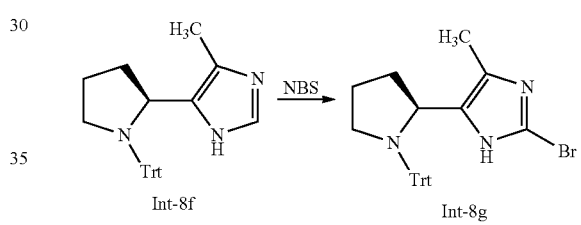

To a solution of Compound Int-8f (3.9 g, 10 mmol) in chloroform (30 mL) was added NBS (1.76 g, 10 mmol) and the mixture was allowed to stir at room temperature for 2 hours. The reaction mixture was then concentrated in vacuo and the residue obtained was purified using flash chromatography on silica gel to provide Compound Int-8g (2.2 g, 47%).

Step G—Preparation of Compound Int-8h

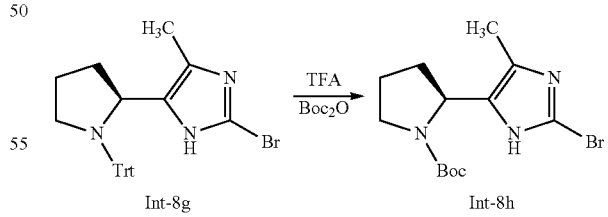

To a solution of Compound Int-8g (1.28 g, 2.7 mmol) in dichloromethane (10 mL) was added TFA (10 mL) and the mixture was allowed to stir at room temperature for 2 hours. Then the mixture was concentrated and used in the next reaction directly. The residue obtained was dissolved in THF (20 mL) and $Et_3N$ (5 mL) and to the resulting solution was added BOC anhydride (590 mg, 2.7 mmol). The mixture was allowed to stir at room temperature for 2 hours and concentrated in vacuo. The residue obtained was purified using chromatography to provide Compound Int-8h (600 mg, 67%).

MS (ESI) m/z (M+H)+: 331.

Example 9

Preparation of Intermediate Compound Int-9g

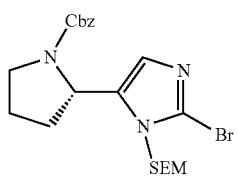

Int-9g

Step A—Preparation of Compound Int-9b

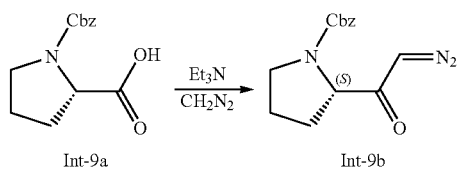

To a solution of Compound Int-9a (50 g, 0.2 mol) in THF (500 mL) and Et₃N (20 mL) was added dropwise isopropyl chloroformate (25 g, 0.22 mol) at ice water bath. Then the resulting solution was allowed to warm to room temperature and allowed to stir for 1 h. Then a solution of CH₂N₂ (0.22 mol) in ether was added slowly until no N₂ gas evolution was noted. Acetic acid (4 mL) was added and the reaction mixture was allowed to stir for 10 minutes. NaHCO₃ solution was then added and the reaction mixture extracted three times with ethyl acetate. The organic layers were combined, dried over Na₂SO₄, and concentrated in vacuo to provide crude product. The crude product was then purified using column chromatography on silica gel (Pet Ether:E.Acetate=3:1) to provide Int-9b (38 g, 70%)

Step B—Preparation of Compound Int-9c

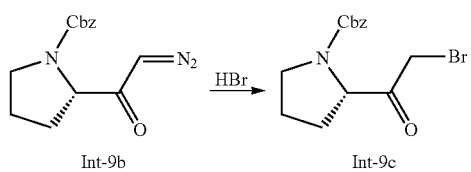

To a solution of Int-9b (38 g, 0.14 mol) in HOAc (20 mL) was added dropwise an aqueous HBr solution (11.2 g, 0.14 mol). After 10 minutes, the mixture was poured into an aqueous NaHCO₃ solution and extracted three times with ethyl acetate. The combined organic layers were washed with brine, water, dried over Na₂SO₄ and concentrated in vacuo to provide Compound Int-9c (30 g, 68%).

Step C—Preparation of Compound Int-9e

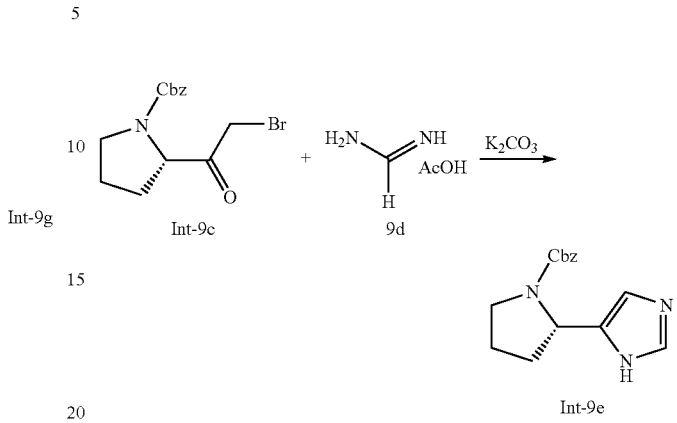

To a solution of Int-9c (10 g, 32 mmol) and compound 9d (8.4 g, 64 mmol) in DMF (70 mL) was added K₂CO₃ (18 g, 126 mmol). The mixture was allowed to stir at 100° C. in a sealed tube for about 15 hours. The solvent was removed and the residue obtained was purified using column chromatography on silica gel (dichloromethane:MeOH=20:1) to provide Compound Int-9e. (6 g, 59%).

Step D—Preparation of Compound Int-9f

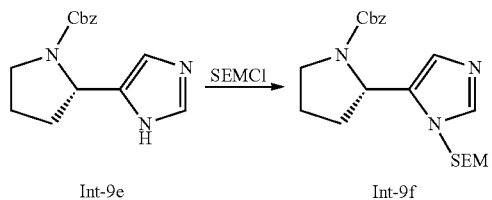 [SMILES: O=C(OCc1ccccc1)N1CCC[C@H]1c1cnc[nH]1 ; "SEMCl" ; C[Si](C)(C)CCOCn1cncc1[C@@H]1CCCN1C(=O)OCc1ccccc1]

To a solution Int-9e (4 g, 14.7 mmol) in THF (40 mL) was added NaH (6.6 g, 60% content, 16.17 mmol) at 0° C. The mixture was allowed to stir at room temperature for 30 minutes. and then cooled to 0° C., and SEM-Cl (2.4 g, 14.7 mmol) added dropwise. The resulting mixture was allowed to stir at 0° C. for 2 hours. The solvent was removed in vacuo and the residue obtained was purified using column chromatography on silica gel (dichloromethane:MeOH=20:1) to provide Compound Int-9f. (2 g, 34%).

Step E—Preparation of Compound Int-9g

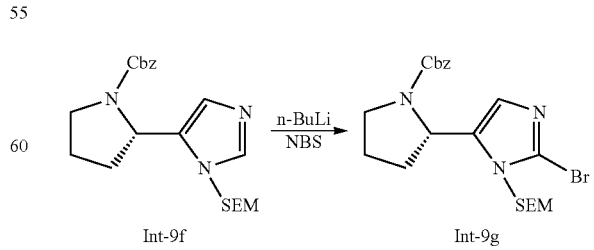

To a solution of Int-9f (2 g, 5 mmol) in THF (20 mL) was added dropwise n-BuLi (2.5 mL, 6.3 mmol) at −78° C. (bath)

under N₂ protection. The resulting solution was allowed to stir at this temperature for 30 minutes. Then a solution of NBS (0.89 g, 5 mmol) in THF (10 mL) was added dropwise at −78° C. The mixture was allowed to stir at −78° C. for 1 hour and then aqueous NH₄Cl solution was added. The organic layer was separated and concentrated off to provide a crude residue, which was purified using column chromatography on silica gel (petroleum ether:EA=3:1 as the eluent) to provide Int-9g (400 mg, 16.5%).

Example 10

Preparation of Intermediate Compound Int-10f

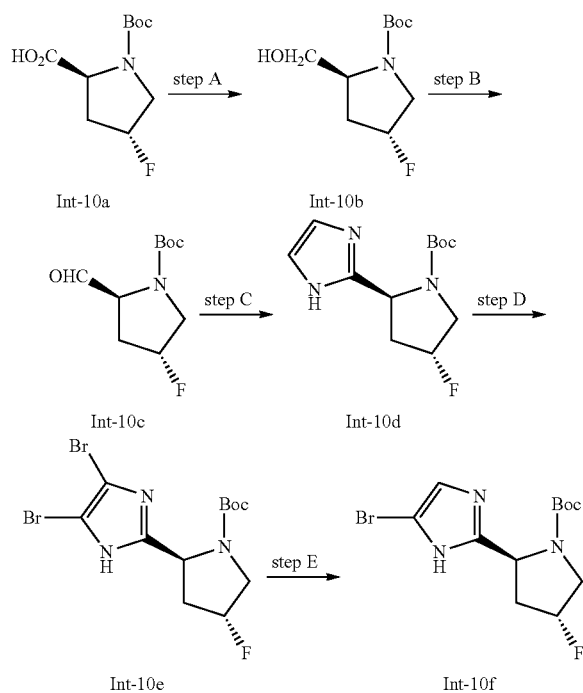

Step A—Preparation of Compound Int-10b (2S,4R)-1-(tert-butoxycarbonyl)-4-fluoropyrrolidine-2-carboxylic acid (Int-10a, 20 g, 85.75 mmol) was dissolved in anhydrous THF and cooled to 0° C. BH₃.THF (1M in THF, 171 mL, 171 mmol) was added via an addition funnel. The solution was gradually warmed up to room temperature and stirred at room temperature for about 15 hours. MeOH was added until no bubbles came out. The solution was concentrated and the product was purified using silica gel chromatography (330 g, 0% to 60% of EtOAc in Hexane) to provide Int-10b (15.1 g, 80.3%)

Step B—Preparation of Compound Int-10c

To a dry 1000 mL round bottom flask was added oxalyl chloride (7.50 mL, 88.9 mmol) and dry dichloromethane (250 mL). After the solution was cooled to −78° C., DMSO (6.80 mL, 95.8 mmol) in dichloromethane (20 mL) was added dropwise. The solution was allowed to stir at −78° C. for 30 minutes. Int-10b (15.0 g, 68.4 mmol) in dichloromethane (50 mL) was added via syringe. After the solution was allowed to stir at −78° C. for 30 minutes, TEA (38.1 mL, 273.6 mmol) was added. The solution was allowed to stir at −78° C. for 30 minutes and at 0° C. for one hour. The solution was diluted with dichloromethane (300 mL) and washed with water, 1N HCl, sat NaHCO₃, and brine. It was dried over anhydrous Na₂SO₄, filtered and concentrated in vacuo. The residue obtained was dried in vacuo for 1 hour to provide Int-10c which was used without further purification.

Step C—Preparation of Compound Int-10d

To a 1000 mL round bottom flask was added Int-10c and NH₃ (7N in MeOH, 150 mL). Glyoxal (15 mL, 40% in water, 131 mmol) was added slowly. The solution was allowed to stir at room temperature for about 15 hours. Additional glyoxal (5 mL, 44 mmol) was added and the reaction was allowed to stir at room temperature for another 24 hours. The solution was concentrated and the product was purified using silica gel chromatography (240 g, 0% to 5% of MeOH in dichloromethane, with 0.1% NH₃.H₂O) to provide Int-10d (8.5 g, 48.7% from 2)

Step D—Preparation of Compound Int-10e

To a 100 mL round bottom flask was added Int-10d (8.5 g, 33.3 mmol) and CH3CN (250 mL). More CH₃CN was added to form a clear solution. NBS (11.3 g, 63.3 mmol) was added in one portion and the solution was allowed to stir at room temperature for about 15 hours. CH₃CN was removed in vacuo and dichloromethane (50 mL) was added with stirring. The solid was filtered and washed with dichloromethane twice. The filtrate was concentrated in vacuo to about 30 mL and filtered again. The filtrate was purified using silica gel chromatography (120 g, 20% to 80% of EtOAc in Hexane) to provide Int-10e (11.88 g, 86.4%).

Step E Preparation of Compound Int-10f

To a 1000 mL round bottom flask was added Int-10d (11.88 g, 28.76 mmol), sodium sulfite (Na₂SO₃, 36.0 g, 288 mmol), EtOH (270 mL) and water (130 mL). The solution was allowed to stir at reflux for about 15 hours. More Na₂SO₃ (10 g, 79 mmol) was added and the solution was allowed to stir at reflux for another 24 hours. After cooling down, the solid was filtered and washed with EtOAc three times. The filtrate was concentrated and the residue obtained was dissolved in a mixture of EtOAc (300 mL) and water (200 mL). The organic layer was separated and washed with brine, dried over anhydrous Na₂SO₄, filtered, and concentrated in vacuo. The product was purified using silica gel chromatography (240 g, 0% to 33% of EtOAc in Hexane) to provide Int-10f (5.12 g, 53.3%).

Example 11

Preparation of Intermediate Compound Int-11c

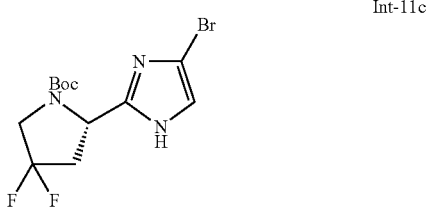 [SMILES: CC(C)(C)OC(=O)N1CC(F)(F)C[C@H]1c1nc(Br)c[nH]1]

Step A—Preparation of Compound Int-11b

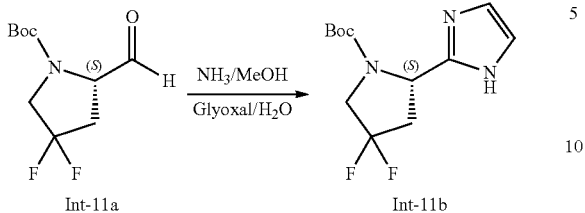

The aldehyde Int-11a was prepared from the commercially available alcohol using the method described in Example 10.

A flask was charged with aldehyde Int-11a (82 g, 0.35 mol) and a 2.33 N ammonia/MeOH solution was added with good stirring (600 mL, 4.0 eq., prepared from 200 ml 7N ammonia/MeOH diluted with 400 ml MeOH). The reaction was then heated to 35° C. and allowed to stir at this temperature for 2 hours, after which time a solution of 40 wt % glyoxal in water (80 mL, 2.0 eq.) was added dropwise over about 15 minutes. After stirring for an additional 2 hours, a solution of 7N ammonia/MeOH (100 mL, 2.0 eq.) was added and the reaction was allowed to stir at 35° C. for 1 hour. Additional glyoxal (40 mL, 1.0 eq.) was then added dropwise over 5 minutes and the resulting reaction was allowed to stir at 35° C. for 1 hour. The reaction mixture was then allowed to cool room temperature and stir for about 15 hours. Additional 7N ammonia/MeOH (50 mL, 1.0 eq.) was then added and the reaction reheated to 35° C. and allowed to stir at this temperature for 1 hour. An additional amount of glyoxal (20 mL, 0.5 eq.) was then added and the resulting reaction was allowed to stir at 35° C. for 1 hour, then the reaction mixture was cooled to room temperature and filtered. The filtrate was concentrated in vacuo and the residue obtained was diluted with dichloromethane and water (2 L, 1:1). The organic layer was separated, washed with 1 L of water, then brine and dried (MgSO$_4$), filtered and concentrated in vacuo. The brown foam residue obtained was further purified using being passed through a short silica gel column to provide Int-11b (60 g, 62%).

Step B—Preparation of Compound Int-11c

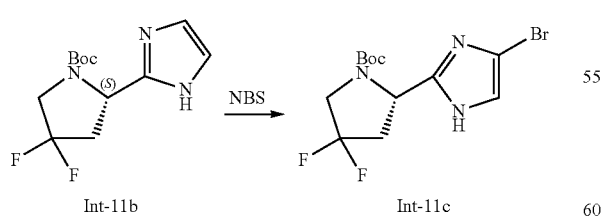

Int-11c was prepared from Int-11b using the method described in Example 10.

Intermediate compounds Int-11d, Int-11e and Int-11f can be prepared using the methods described in Example 10 and Example 11.

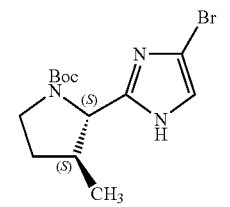

Int-11d

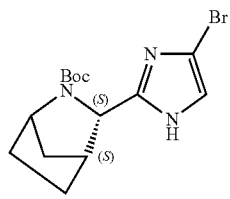

Int-11e

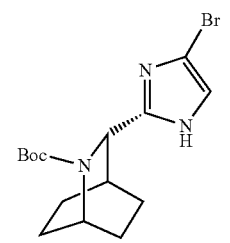

Int-11f

Example 12

Preparation of Intermediate Compound Int-12i

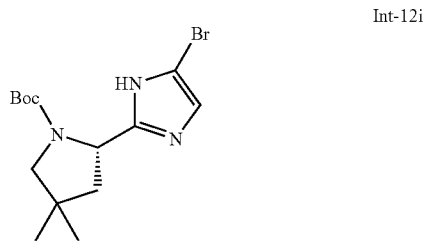 [SMILES: CC1(C)C[C@@H](c2ncc(Br)[nH]2)N(C(=O)OC(C)(C)C)C1]

Int-12i

Step A—Preparation of Compound Int-12b

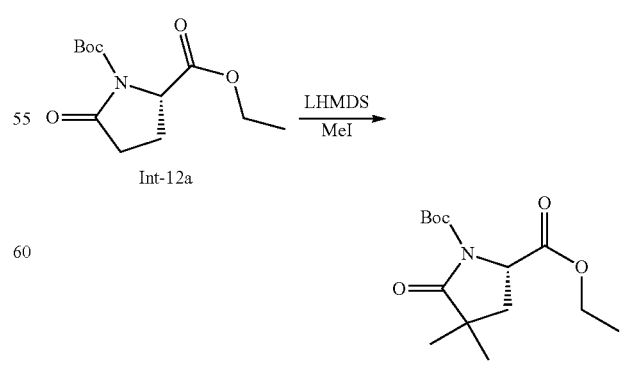

To a solution of Compound Int-12a (60 g, 0.24 mol) in dry THF (1 L) stirred at −78° C. was added lithium hexamethyldisilazide (82 g, 0.49 mol, 1 M in THF). After the reaction mixture had been stirred at −78° C. for 1 hour, the iodomethane (66 g, 0.46 mol) dissolved in dry THF (100 mL) was added at −78° C. and the mixture was allowed to stir for 15 minutes at this temperature and 2 hours at 25° C. The reaction mixture was quenched with saturated ammonium chloride solution and extracted with dichloromethane (3×300 mL). The combined organic phases were dried over MgSO$_4$, filtered, and concentrated in vacuo to dryness. The products were purified using silica gel chromatography to provide Compound Int-12b (18.3 g, 27%). $^1$H NMR 4.38-4.34 (m, 1H), 4.08-4.05 (m, 2H), 2.09-2.03 (m, 1H), 1.77-1.73 (m, 1H), 1.35 (s, 9H), 1.12 (t, J=8 Hz, 3H), 1.06 (s, 6H).

Step B—Preparation of Compound Int-12c

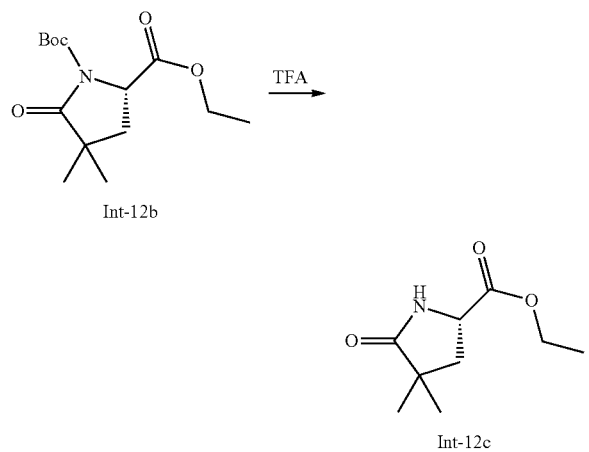

To a solution of Compound Int-12b (18.3 g, 60 mmol) in dichloromethane (150 mL) was added TFA (15 mL) and the mixture stirred at room temperature for 30 minutes. The solvent was removed to provide Compound Int-12c (11.2 g, 100%).

Step C—Preparation of Compound Int-12d

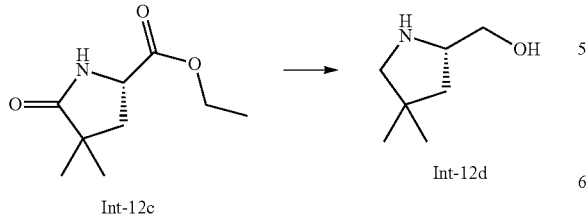

A suspension of LiAlH$_4$ (16.2 g, 0.44 mol) and Compound Int-12c (11.2 g, 54.8 mmol) in THF (200 mL) was allowed to stir under reflux for 8 hours. After successive addition of 17 mL of water, 17 mL of 10% aq NaOH, and 51 mL of water, and filtration, the filtrate was concentrated in vacuo to provide Compound Int-12d (6.7 g, 94%).

Step D—Preparation of Compound Int-12e

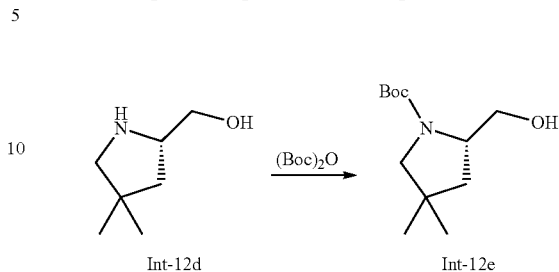

Compound Int-12D was dissolved in THF and Et$_3$N, (Boc)$_2$O were added. The mixture was allowed to stir at room temperature for 2 hours and concentrated in vacuo. The residue obtained was purified using chromatography to provide Int-12e (14 g, 100%).

Step E—Preparation of Compound Int-12f

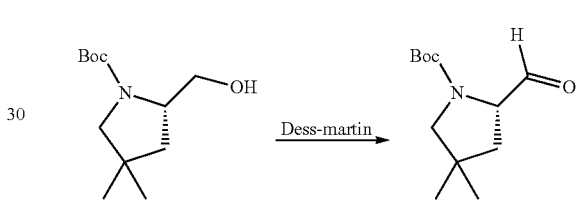

To a solution of Compound Int-12e (14 g, 65.4 mmol) in dichloromethane was added Dess-Martin reagent (41.6 g, 98.1 mol). After stirring at room temperature for about 15 hours, the solvent was removed and the residue obtained was purified using silica gel chromatography to provide Compound Int-12f (7 g, 47%). $^1$H NMR δ: 9.40 (s, 1H), 4.05-4.03 (m, 1H), 3.14-3.11 (m, 2H), 1.83-1.79 (m, 1H), 1.66-1.63 (m, 1H), 1.36 (s, 9H), 1.02 (s, 6H).

Step F—Preparation of Compound Int-12g

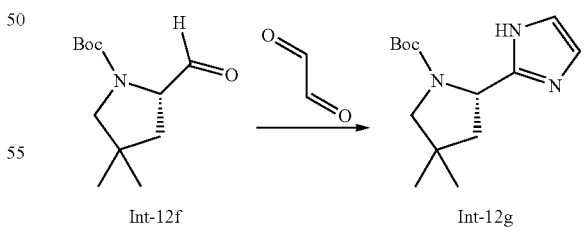

Glyoxal (1.75 mL of 40% in water) was added dropwise over 11 minutes to a solution of NH$_4$OH (26 mL) and Compound Int-12f (6.1 g, 28.8 mmol) in methanol and stirred at ambient temperature for 19 hours. The volatile component was removed in vacuo and the residue obtained was purified using a flash chromatography on silica gel to provide Compound Int-12g (3 g, 39%).

MS (ESI) m/z (M+H)$^+$: 266.

Step G—Preparation of Compound Int-12h

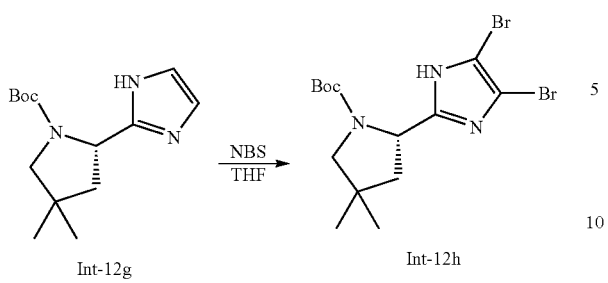

A mixture of Compound Int-12g (2.2 g, 8.3 mmol), N-bromosuccinimide (2.66 g, 14.9 mmol) in anhydrous THF (80 mL) was heated at reflux for about 15 hours. After cooling to room temperature, the solids are removed by filtration and the filtrate was concentrated in vacuo and the residue obtained was purified using chromatography to provide Compound Int-12h (2.0 g, 57%). $^1$H NMR (J000120117 H10170-003-1 CDCl$_3$ varian 400 MHz) δ: 11.03 (s, 1H), 4.79 (t, J=8 Hz, 1H), 3.25 (t, J=12 Hz, 1H), 2.96 (t, J=12 Hz, 1H), 2.58-2.53 (m, 1H), 2.95-1.90 (m, 1H), 1.34 (s, 9H), 1.05 (s, 3H), 0.99 (s, 3H). MS (ESI) m/z (M+H)$^+$: 422.

Step H—Preparation of Compound Int-12i

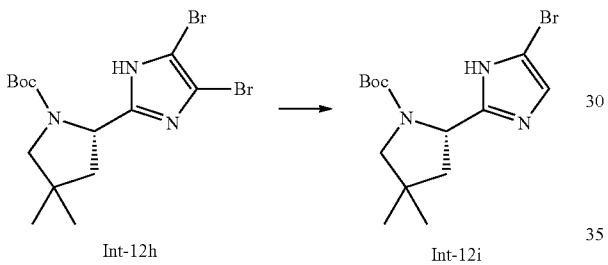

To the solution of Compound Int-12h (1.9 g, 4.5 mmol) in H$_2$O/EtOH (40 mL/20 mL) was added Na$_2$SO$_3$ (5.6 g, 4.5 mmol) and the mixture was allowed to stir at room temperature for about 15 hours. The reaction mixture was concentrated in vacuo and the residue obtained was dissolved in ethyl acetate, washed with brine, dried over MgSO$_4$, filtered, and concentrated in vacuo. The residue obtained was purified using chromatography on silica gel to provide Compound Int-12i (0.75 g, 48%). $^1$H NMR δ: 6.92 (s, 1H), 4.71-4.67 (m, 1H), 3.26-3.21 (m, 2H), 2.01-1.96 (m, 1H), 1.78-1.72 (m, 1H), 1.13 (s, 9H), 1.00 (s, 3H).

Example 13

Preparation of Intermediate Compounds Int-13d and Int-13e

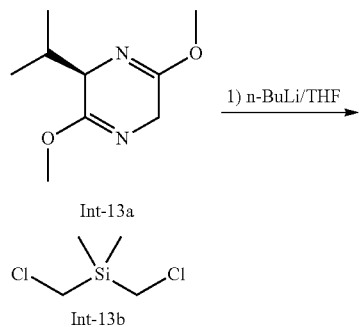

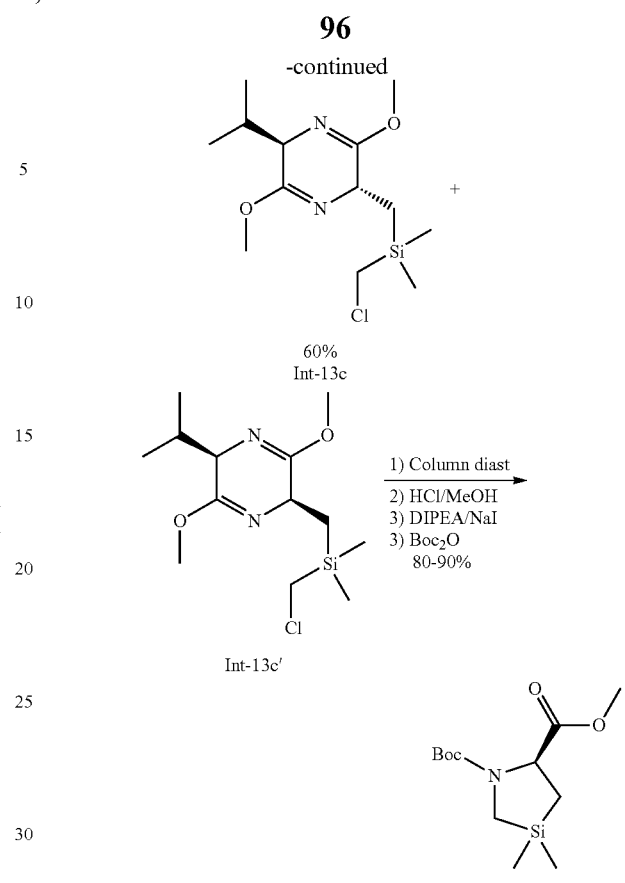

Step A—Preparation of Compound Int-13c

A 5 L—3 necked round bottomed flask, equipped with a mechanical stirrer, temperature probe, addition funnel and N$_2$ inlet, was charged with the Schollkopf chiral auxiliary—(Int-13a, 200 g, 1.09 mol, 1.0 eq), bis(chloromethyl)dimethylsilane (Int-13b, 256 g, 1.63 mol, 1.5 eq), and THF (2 L, Aldrich anhydrous). The flask was cooled in a dry ice/2-propanol bath until the internal temperature reached −75° C. n-Butyllithium (Aldrich 2.5 M in hexanes, 478 mL, 1.19 mol, 1.09 eq) was added via a dropping funnel over 1 hour while maintaining the internal reaction temperature between −67° C. and −76° C. The resulting orange-red solution was allowed to gradually warm to room temperature for about 15 hours. The reaction mixture was then re-cooled to 0° C. and quenched with 500 mL of water. Diethyl ether (2 L) was added and the layers were separated. The aqueous layer was extracted with 1 L of diethyl ether. The combined organic layers was washed with water and brine, dried with MgSO$_4$, filtered, and concentrated in vacuo to dryness, giving 480 g of orange oil. This material was left in vacuo for about 15 hours to provide 420 g of oil. The crude product was split into two batches and purified via silica gel chromatography on a 1.6 kg flash column. The column was eluted with gradient of 0-4% Et$_2$O in hexanes. The product fractions were concentrated in vacuo at a bath temperature at or below 40° C. giving 190 grams of Int-13c-(60%).

Step B—Preparation of Compound Int-13d

A 5 L, 3-necked round bottomed flask equipped with a mechanical stirrer, addition funnel, temperature probe, external water bath and $N_2$ inlet was charged with Compound Int-13c (196 g, 0.643 mol, 1.0 eq) and methanol (1.5 L). Aqueous HCl (500 mL of 10% by volume) was added at room temperature over 30 minutes, with a mild exotherm observed. The temperature increased to 37° C. then dropped back down. The reaction mixture was allowed to stir at room temperature for 3 hours and was monitored by TLC and LCMS. The reaction mixture was then concentrated in vacuo to an oil. Additional methanol (3×200 mL) was added and the reaction mixture was concentrated in vacuo to dryness again. The resulting crude product was dried under house vacuum for about 15 hours. The crude product was then dissolved in $CH_2Cl_2$ (750 mL) and $Et_2O$ (1250 mL) and sodium iodide (96.4 g, 0.643 mol, 1.0 eq) was added. Diisopropylethylamine (336 mL, 1.929 mol, 3.0 eq) was added slowly over 25 minutes with stirring, causing the temperature to increase to 35° C. then decrease to room temperature again. The reaction mixture was allowed to stir at room temperature for 2 hours, after which time the MS of an aliquot indicated consumption of the starting material. The reaction mixture was allowed to stir for an additional 2 hours and then Boc-anhydride (281 g, 1.286 mol, 2.0 eq) was added. The reaction mixture was then allowed to stir at room temperature. After two days, the reaction mixture was diluted with EtOAc (2 L) and water (1 L), and the layers were separated. The aqueous phase was extracted with 500 mL of EtOAc. The combined organic layers were washed with water (500 mL), and brine (500 mL), dried with $MgSO_4$, filtered, and concentrated in vacuo to a yellow oil (380 g). The crude product was split into two 180 g portions for convenience and each portion was purified via flash silica gel chromatography. Column conditions for a 180 g portion of crude product are as follows. The 180 gram sample of crude product was loaded onto a 191 g $SiO_2$ cartridge and purified on a 1.51 g $SiO_2$ column. The column was eluted using a 0%-20% EtOAc/hexanes gradient as the mobile phase to provide 52 grams of pure Int-13d and additional fractions of Int-13d that contained a small amount of a Boc-valine impurity. The impure fractions from the two columns were recombined and re-purified. After chromatography, Compound Int-13d was obtained as an oil which solidified to a white solid on standing (128 g, 65% yield over the three steps.)

Step C—Preparation of Compound Int-13e

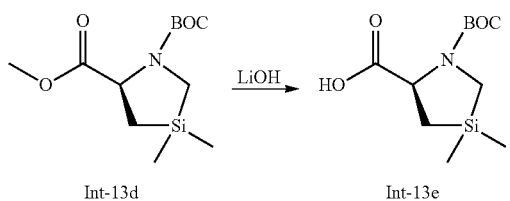

A solution of Int-13d (8.5 g, 31.1 mmol) in methanol (100 mL) and 1.0 M aqueous KOH solution (48 mL, 48 mmol) was allowed to stir at room temperature for about 15 hours. The reaction was then neutralized with 48 ml of 1.0 M aqueous HCl solution to pH ~5, and partially concentrated in vacuo. The aqueous layer was then extracted twice with dichloromethane (2×100 mL). The combined organic solutions were concentrated in vacuo to provide Int-13e as a gel (7.74 g, 96%).
Note: Because of poor UV absorbance, the above reactions were monitored by TLC using Hanessian's stain. To prepare the visualization stain, combine 450 mL of $H_2O$, 25 g ammonium molybdate, 5 g of eerie sulfate, and 50 mL of conc. HCl or conc. $H_2SO_4$.

Example 14

Preparation of Intermediate Compound Int-14d

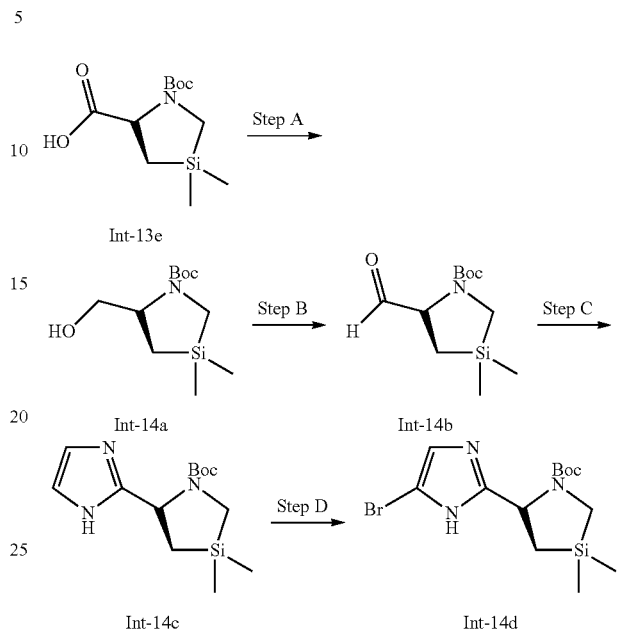

Step A—Preparation of Compound Int-14a

To a mixture of carboxylic acid Int-13e (20 g, 77 mmol) in THF (400 mL) at 0° C. was added 1M $BH_3$ in THF (0.17 L) via addition funnel at 0° C. The mixture was allowed to warm to room temperature and stir for about 15 hours. The reaction was carefully quenched by addition of MeOH (~75 mL) until bubbling ceased. The reaction mixture was concentrated in vacuo to dryness whereupon the residue obtained was partitioned between EtOAc and $H_2O$. The layers were separated and the aqueous layer was extracted with EtOAc (2×). The organic layers were combined, washed with brine, dried ($Na_2SO_4$), and concentrated in vacuo to provide Int-14d (18 g, 99%) as a clear oil, which was used without further purification. MS (ESI) m/e (M+H+Na)$^+$: 268.

Step B—Preparation of Compound Int-14b

To a dry 2-necked flask equipped with a stir bar was added oxalyl chloride (8.2 mL, 96 mmol) and $CH_2Cl_2$ (280 mL). The solution was cooled to −78° C. whereupon a solution of DMSO (7.4 mL, 0.10 mol) in $CH_2Cl_2$ (22 mL) was added and the mixture was allowed to stir for 30 minutes at −78° C. A solution of alcohol Int-14a (18 g, 74 mmol) from Step A in $CH_2Cl_2$ (60 mL) was added dropwise via addition funnel over 30 minutes. The resulting solution was allowed to stir for an additional 30 minutes at −78° C. whereupon $Et_3N$ (42 mL, 0.30 mol) was added dropwise. The mixture was allowed to stir for 30 minutes at −78° C., warmed to 0° C., and allowed to stir for an additional 1.5 hours. The mixture was diluted with $CH_2Cl_2$ (400 mL) and was transferred to a separatory funnel. The organic layer was washed with sat. aq $NH_4Cl$ (2×100 mL) and brine (2×100 mL). The organic layer was dried ($Na_2SO_4$), filtered, and concentrated in vacuo to provide Int-14b, 18 g (99%) as a clear oil, which was used without further purification.

Step C—Preparation of Compound Int-14c

To a round bottom flask charged with aldehyde Int-14b (18 g, 74 mmol) from Step B was added a 7N $NH_3$ in MeOH solution (28 mL, 0.19 mol) in MeOH (37 mL) at room temperature. The mixture was allowed to stir for 30 minutes at room temperature whereupon a solution of glyoxal (14 g, 96 mmol) was added over 5 minutes. The resulting solution was allowed to stir for 12 hours at room temperature and was concentrated in vacuo. The residue obtained was purified using column chromatography using a gradient of 100% $CH_2Cl_2$ to 97.5% $CH_2Cl_2$/2.5% MeOH to provide Int-14c, 9.9 g (48%) as yellow oil. MS (ESI) m/e (M+H)$^+$: 282.

Step D—Preparation of Compound Int-14d

To a solution of imidazole Int-14c (1.0 g, 3.6 mmol) from Step C in $CH_2Cl_2$ (5 mL) at 0° C., was added NBS (0.44 g, 2.5 mmol) in $CH_2Cl_2$ (10 mL) dropwise via addition funnel. The resulting mixture was allowed to stir for 90 minutes at 0° C. whereupon the mixture was concentrated in vacuo to dryness. The crude residue obtained was partitioned between $CHCl_3$ (10 mL) and water (3 mL) and the layers were separated. The organic layer was washed with water (3×3 mL), dried ($Na_2SO_4$), filtered, and concentrated in vacuo. The residue obtained was purified using column chromatography (80 g) using a gradient of 100% hexanes to 65% hexanes/35% EtOAc to provide Int-14d, (0.35 g, 27%) as a white solid. MS (ESI) m/e (M+H)$^+$: 360/362.

Example 15

Preparation of Intermediate Compound Int-15c

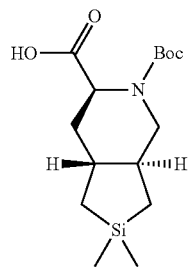

Int-15c

Step A—Preparation of Compound Int-15a

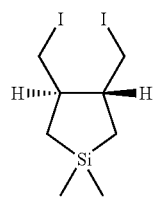

Int-15a

To a solution of dichlorozirconocene ($Cp_2ZrCl_2$) (4.2 g, 14.2 mmol) in 40 mL THF at −78° C. was added n-BuLi (1.6 M in hexane, 18 mL, 28.4 mmol). The resulting reaction was allowed to stir for 1 hour, then diphenyldiallylsilane (2 g, 14.2 mmol) in 17 mL of THF was added at −78° C. The reaction was allowed to stir for 1 hour at −78° C. and for 18 hours at 25° C. Iodine (9 g, 35.5 mmol) in 20 mL THF was then added at −78° C. and the mixture was allowed to stir for 1 hour. The reaction was quenched with 10% aqueous $H_2SO_4$ and the organic phase was extracted by ether. The organic solution was washed with saturated aqueous $NaHCO_3$ solution, brine solution, and dried ($Na_2SO_4$). After filtration, the filtrate was concentrated in vacuo and the residue obtained was purified using ISCO 120 g column (hexane) to provide Compound Int-15a, 2.75 g (49%). $^1$H NMR ($CDCl_3$) δ 3.44 (dd, J=2.2, 10.0 Hz, 2H), 3.33 (dd, J=4.7, 10.0 Hz, 2H), 1.20 (m, 2H), 0.93 (dd, J=5.9, 14.7 Hz, 2H), 0.63 (dd, J=11.1, 14.2 Hz, 2H), 0.19 (s, 6H).

Step B—Preparation of Compound Int-15b

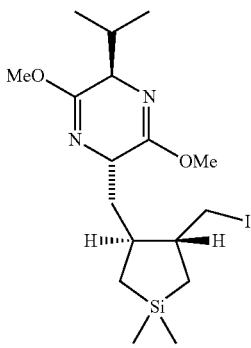

Int-15b

To a solution of (2R)-(−)-2,5-dihydro-3,6-dimethoxy-2-isopropylpyrazine (0.61 g, 4.36 mmol) in THF (8 mL) was added n-BuLi (2.5 M in hexane, 1.8 mL, 4.58 mmol) at −78° C. After allowed to stir for 0.3 hours, Compound Int-15a (2.75 g, 6.98 mmol) in 2 mL of THF was added and the mixture was allowed to stir at the temperature for 4 hours. The reaction was quenched by saturated aqueous $NH_4Cl$ solution and the organic layers were extracted with EtOAc. The combined organic solution was washed with brine solution, dried ($Na_2SO_4$), and concentrated in vacuo. The residue obtained was purified using ISCO 40 g column (gradient from 0% to 2.5% ether in hexane) to provide Compound Int-15b, 783 mg (44%). $^1$H NMR ($CDCl_3$) δ 4.05 (m, 1H), 3.96 (t, J=3.4 Hz, 1H), 3.72 (s, 3H), 3.71 (s, 3H), 3.49 (dd, J=2, 8, 0.4 Hz, 1H), 3.26 (dd, J=6, 9.4 Hz, 1H), 2.30 (m, 1H), 1.96 (m, 1H), 1.60 (m, 2H), 1.37-1.17 (m, 3H), 1.08 (d, J=6.9 Hz, 3H), 0.99-0.86 (m, 2H), 0.72 (d, J=6.6 Hz, 3H), 0.49 (dd, J=11.0, 14.4 Hz, 1H), 0.35 (dd, J=11.0, 14.2 Hz, 1H), 0.16 (s, 6H).

Step C—Preparation of Compound Int-15c

To a solution of Compound Int-15b (780 mg, 1.92 mmol) in MeOH (9 mL) was added 10% aqueous HCl (3 mL) at 0° C. and the mixture was allowed to stir at 25° C. for 18 hours. The mixture was concentrated in vacuo and the residue obtained was coconcentrated in vacuo with MeOH twice. The resulting white foam was dissolved in ether (6 mL) and $CH_2Cl_2$ (9 mL), and diisopropylethylamine (1 mL, 5.7 mmol) was added. After stirred at 25° C. for 18 hours, di-t-butyl dicarbonate (922 mg, 4.22 mmol) was added and the resulting mixture was allowed to stir at 25° C. for 2 days. The mixture was added to cold water and the organic layers were extracted with EtOAc. The combined organic solution was washed with brine solution, dried ($Na_2SO_4$), and concentrated in vacuo. Then the residue obtained was dissolved in MeOH (8 mL) and treated with aqueous 1 M KOH solution (3.3 mL, 3.3 mmol). After stirred at 0° C. to 25° C., the reaction mixture was acidified with 10% aqueous HCl and the organic layers were extracted with $CH_2Cl_2$. The combined organic solution was washed with brine solution, dried (Na₂SO₄), and concentrated in vacuo to provide Compound Int-15c, which was used without further purification.

Example 16

Preparation of Intermediate Compound Int-16e

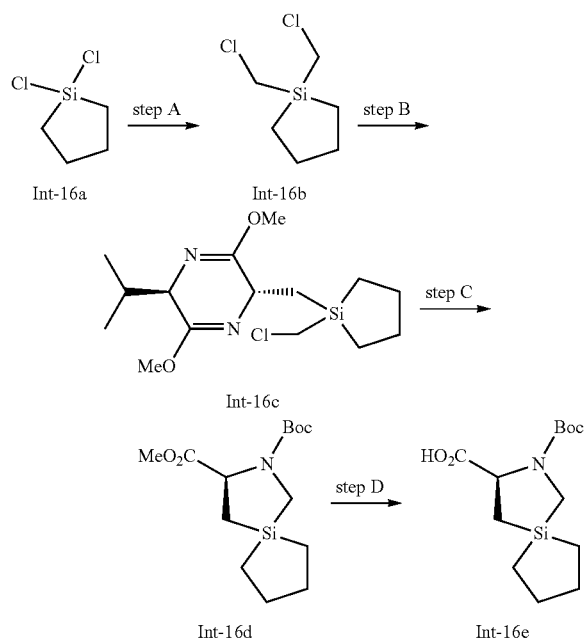

Step A—Preparation of Compound Int-16b

To a 1000 mL flame dried flask was added 1,1-dichlorosilolane (Int-16a, 28.09 g, 181.1 mmol), bromochloromethane (23.5 mL, 362.2 mmol), and anhydrous THF (400 mL). The solution was cooled to −70° C., then n-BuLi (2.5M in hexane, 145 mL, 362 mmol) was added slowly over a period of 1 hour. The resulting reaction was allowed to stir at −70 to −60° C. for 20 minutes, then was allowed to warm to room temperature over 1 hour. Saturated NH₄Cl solution (200 mL) and Et₂O (200 mL) were then added and the organic layer was separated and the aqueous layer was extracted with Et₂O (100 mL) twice. The organic layers were combined, washed with brine, dried over Na₂SO₄, filtered and concentrated in vacuo. The residue obtained was purified using SiO₂ chromatography (240 g, eluted with hexane) to provide Compound Int-16b (17.2 g, 51.9%).

Step B—Preparation of Compound Int-16c

To a 500 mL flame dried flask was added (R)-2-isopropyl-3,6-dimethoxy-2,5-dihydropyrazine (10.0 g, 54.3 mmol) and anhydrous THF (200 mL). The solution was cooled to −78° C. n-BuLi (2.5M in hexane, 24.0 mL, 59.7 mmol) was added dropwise. After the solution was allowed to stir at −78° C. for 30 minutes, Compound Int-16b (in 5 mL anhydrous THF) was added dropwise. After the solution was allowed to stir at −78° C. for 1 hour, it was allowed to warm up to room temperature in two hours. Water (100 mL) and Et₂O (150 mL) were added. The organic layer was separated and the aqueous layer was extracted with Et₂O (100 mL) twice. The organic layers were combined, washed with brine, dried over Na₂SO₄, filtered and concentrated in vacuo. The residue obtained was purified using SiO₂ chromatography (40 g, eluted with Et₂O in Hexane: 0% to 3%) to provide Compound Int-16c (10.43 g, 58.0%).

Step C—Preparation of Compound Int-16d

To a 500 mL flask was added Compound Int-16c (11.5 g, 34.8 mmol) and MeOH (80 mL). 10% HCl (20 mL) was added. The solution was allowed to stir at room temperature for 5 hours and concentrated in vacuo. The residue obtained was dissolved in 20 mL MeOH and concentrated again to remove water and HCl. This process was repeated three times. The residue obtained was dissolved in dichloromethane (50 mL) and Et₂O (70 mL). DIPEA (15.4 mL, 86.9 mmol) and NaI (5.2 g, 34.75 mmol) were added. The solution was allowed to stir at room temperature for about 15 hours. Di-tert-butyl dicarbonate (18.9 g, 86.9 mmol) was added. The solution was allowed to stir at room temperature for 4 hours. Water (100 mL) and EtOAc (100 mL) were added. The organic layer was separated and the aqueous layer was extracted with EtOAc (100 mL) twice. The organic layers were combined and washed with brine, dried over anhydrous Na₂SO₄, filtered, and concentrated in vacuo. The product was purified using SiO₂ chromatography (220 g, Hexane/EtOAC: 0% to 20%) to provide Compound Int-16d (7.9 g, 75.9%).

Step D—Preparation of Compound Int-16e

Compound Int-16d (7.9 g, 26.4 mmol) was dissolved in MeOH (100 mL) and cooled to 0° C. KOH (1M in water, 39.6 mL, 39.6 mmol) was added. The solution was allowed to stir at 0° C. for 2 hours, and then at room temperature for 3 hours. HCl (2 N, 20 mL) was added, then additional HCl was added slowly to adjust the solution to pH 4. The acidified solution was concentrated in vacuo and to the residue obtained was added water (150 mL) and EtOAc (200 mL). The organic layer was separated and the aqueous layer was extracted with EtOAc (2×100 mL). The combined organic extracts were washed with brine, dried over anhydrous Na₂SO₄, filtered, and concentrated in vacuo. The residue obtained was dried in vacuo for 48 hours to provide Compound Int-16e (7.45 g, 99%), which was used without further purification.

Example 17

Preparation of Intermediate Compound Int-17i

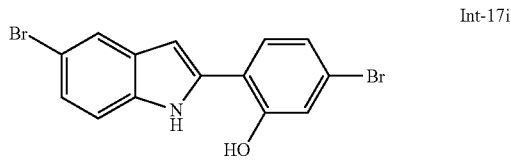 [SMILES: Oc1cc(Br)ccc1-c1cc2cc(Br)ccc2[nH]1]

Step A—Preparation of Compound Int-17b

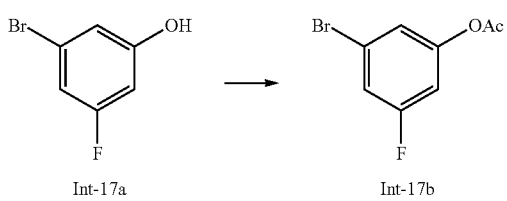 [SMILES: Oc1cc(F)cc(Br)c1 ; CC(=O)Oc1cc(F)cc(Br)c1]

To a 500 mL flask was added Int-17a (25.0 g, 130 mmol), dry dichloromethane (250 mL) and DIPEA (25.37 g, 195 mmol). The solution was cooled to 0° C. and acetyl chloride (13.27 g, 169 mmol, in 30 mL dry dichloromethane) was added dropwise. The resulting reaction was allowed to stir at 0° C. for one hour and then at room temperature for about 15 hours. The solution was diluted with EtOAc and washed with water. The organic phase was dried over anhydrous $Na_2SO_4$, filtered, and concentrated in vacuo. The product was purified using silica gel chromatography (330 g, 0% to 50% of EtOAc in Hexane) to provide Int-17b (22.58 g, 74.5%)

Step B—Preparation of Compound Int-17c

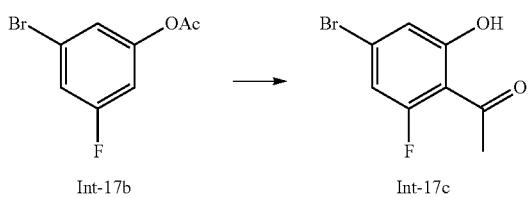

Int-17b    Int-17c

To a 500 mL flask was added Int-17b (21.45 g, 92.05 mmol) and dry dichloromethane (200 mL). It was cooled to 0° C. and aluminum trichloride ($AlCl_3$, 36.82 g, 276.2 mmol) was added in portions. After the solution was allowed to stir at 0° C. for 30 minutes, it was concentrated in vacuo. The semi-solid residue obtained was heated at 140° C. for three hours. After it was cooled to 80° C., water (10 mL) was added dropwise. It was then cooled to 0° C. and EtOAc (300 mL) and water (200 mL) were added. The suspension was allowed to stir at 0° C. until the entire solid dissolved. More EtOAc was added and the organic layer was separated. The organic layer was washed with water, dried over anhydrous $Na_2SO_4$, filtered, and concentrated in vacuo. The product was purified using silica gel chromatography (330 g, 0% to 10% of EtOAc in Hexane) to provide Int-17c (18.76 g, 87%).

Step C—Preparation of Compound Int-17h

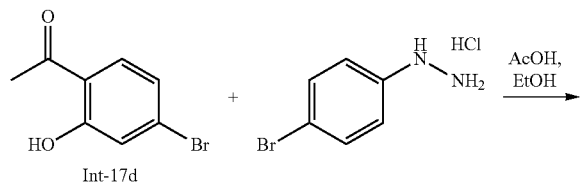

Int-17d

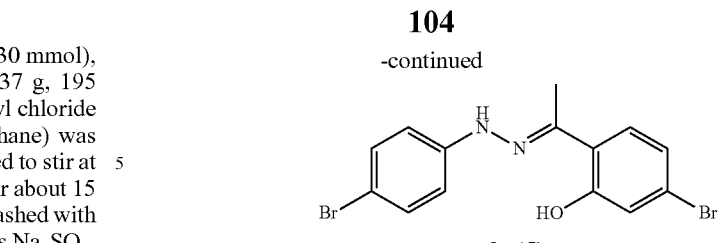

Int-17h

A mixture of Int-17d (prepared using the method described above for the synthesis of Compound Int-17c, 4.2 g, 20 mmol) and 4-bromophenyl hydrazine hydrochloride (4.4 g, 20 mmol) in AcOH and EtOH (1:10, 100 mL) was heated to reflux for 6 hours. The solvent was removed in vacuo to provide a solid, Int-17h, which was used without further purification (9.2 g crude). MS (ESI) m/e (M+H$^+$): 383.

Step D—Preparation of Compound Int-17i

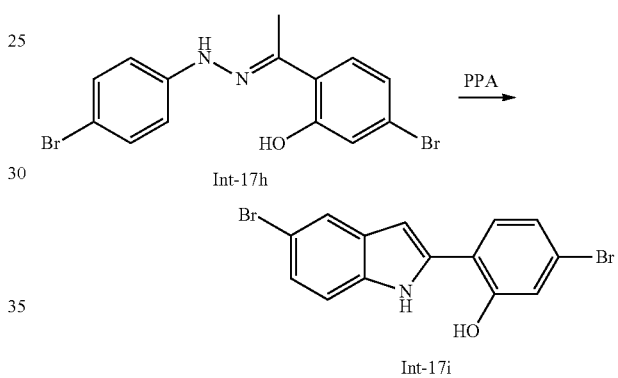

A mixture of Int-17h (9.2 g) in PPA was heated to 80° C. for 2 hours. After cooling to room temperature, the mixture was poured into ice water. The resulting solution was extracted with dichloromethane. The combined organic phases were washed with brine, dried over $Na_2SO_4$, and concentrated in vacuo. The residue obtained was purified using column chromatography to provide Int-17i (4.8 g). MS (ESI) m/e (M+H$^+$): 368.

Example 18

Preparation of Compound 2

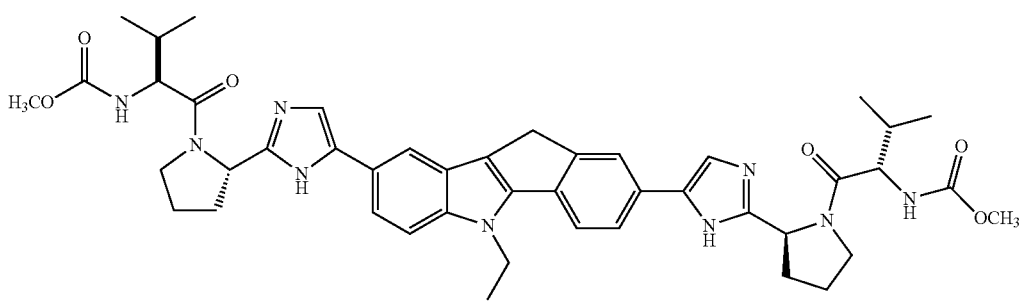

Step A—Synthesis of Compound Int-18b

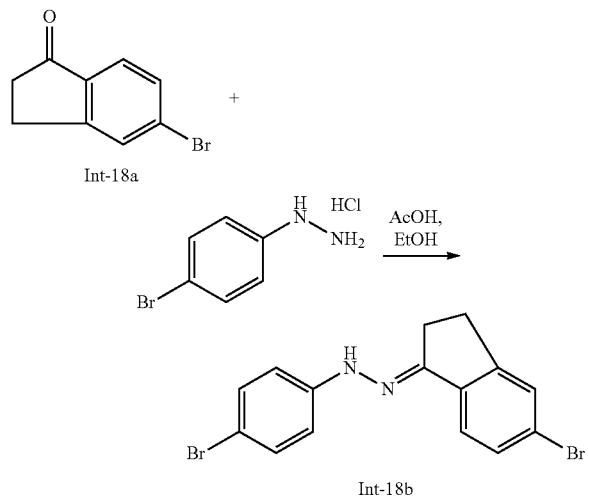

4-Bromophenylhydrazine hydrochloride (13.50 g/60.4 mmol/1.05 eq) and 5-bromo-1-indanone (Int-18a, 12.15 g/5.76 mmol/1.0 eq) were suspended in absolute ethanol (330 mL) and glacial acetic acid (20 mL). The flask was equipped with a stir bar and condenser, then heated to 50° C. After stirring at 50° C. for 16 hours, the reaction mixture was allowed to cool to room temperature, causing a solid material to precipitate. The reaction mixture was concentrated in vacuo, giving a brown solid. Water (150 mL) was added. The reaction mixture was allowed to stir at room temperature for 10 minutes, then suction filtered. The filter cake was rinsed with 3×50 mL of hexanes. A tan solid was obtained, which was left in a vacuum oven over the weekend, giving 18.47 grams of Int-18b which was used in the next step without further purification. MS (ESI) m/e (M+H$^+$): 381.0.

Step B—Synthesis of Compound Int-18c

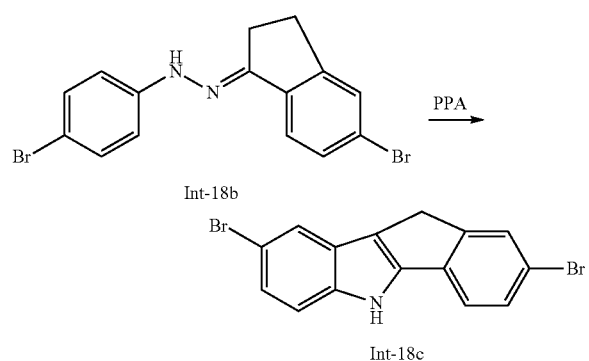

Polyphosphoric acid (175 g) was added to a 500 mL Erlenmeyer flask equipped with a large stir bar. The flask was placed in an oil bath that had previously been heated to 80° C. The bath was warmed to 110° C. and Int-18b (12.25 g/32.2 mmol/1.0 eq), was added in portions with stirring. The reaction mixture was allowed to stir for 2 hours, and then poured into a large beaker containing ice and water. The resulting mixture was extracted with EtOAc. The combined organic layer was washed with water and brine and dried with MgSO$_4$. The filtrate was partially concentrated in vacuo and the crude product was filtered through a plug of silica gel. The silica was rinsed with 3×200 mL of additional EtOAc. The combined EtOAc filtrate solution was concentrated in vacuo, giving 9.07 g of Int-18c as a brown solid. The crude product was purified via silica gel chromatography on a 460 g silica gel column. The column was packed with 10% CH$_2$Cl$_2$ in hexanes and eluted with a 15%-30% CH$_2$Cl$_2$/hexanes gradient mobile phase. The major peak was collected as product to provide 2.97 g of Int-18c as a brown solid. MS (ESI) m/e (M+H$^+$): 361.9, 363.9, 365.9.

Step C—Synthesis of Compound Int-18d

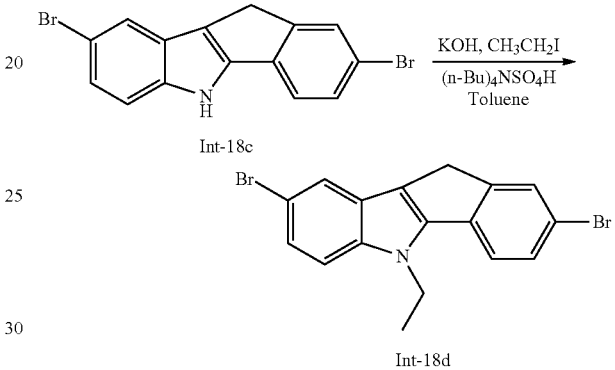

Int-18c (0.127 g/0.35 mmol/1.0 eq), toluene (1.4 mL), 50% aq tetrabutyl ammonium sulfate (40 microliters), and solid KOH (96 mg) were added to a scintillation vial equipped with a stir bar. The reaction mixture was allowed to stir at room temperature for 5 minutes. Ethyl iodide (60 microliters) was added and the reaction mixture was allowed to stir for about 15 hours at room temperature. TLC (9:1 Hexanes:EtOAc) showed no starting material remained. The reaction mixture was diluted with EtOAc and aq NH$_4$Cl. The layers were separated. The organic layer was washed with water and brine, filtered, and concentrated in vacuo. A brown oil was obtained (0.17 g) as product. The crude product was purified via sgc on an ISCO 40 g SiO$_2$ cartridge using a 5%-10% EtOAc/hexanes gradient as the mobile phase. The major peak was collected as product giving 0.2 g of Int-18d as a gray solid. MS (ESI) m/e (M+H$^+$): 389.9/391.9.

Step D—Synthesis of Compound Int-18e

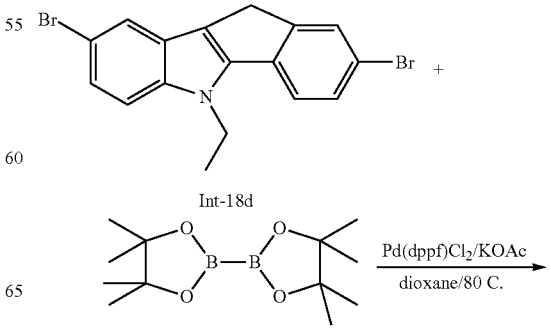

-continued

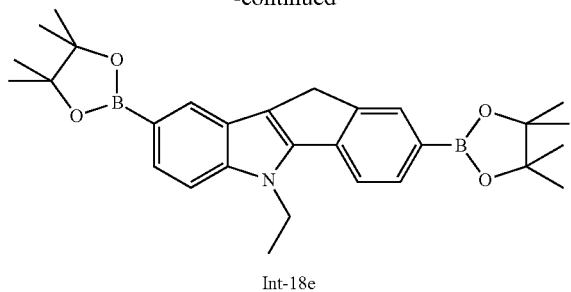

Int-18e

Pinacolatodiboron (129 mg), potassium acetate (68 mg), and [1,1-Bis(diphenylphosphino)-ferrocene]dichloropalladium (II) complex (1:1 with $CH_2Cl_2$) (17 mg) were added to a 10 mL Schlenck tube equipped with a stir bar. The tube was capped with a septum, connected to a vacuum line, and cycled between vacuum and nitrogen five times. A solution of Int-18d (80 mg) dissolved in dioxane (2 mL) was added via syringe. The tube was cycled between vacuum and nitrogen three times, then placed in an oil bath that had been pre-heated to 80° C. The reaction mixture was allowed to stir at 80° C. under $N_2$ for 1.5 hours. The reaction mixture was allowed to cool to room temperature, then was diluted with EtOAc and water. The layers were separated. The organic layer was washed with water and brine, dried with $MgSO_4$, filtered, and concentrated in vacuo, giving a brown oil. The crude product was purified via sgc using a 40 g Isco Gold $SiO_2$ cartridge using 5%-20%/hexanes gradient as the mobile phase to provide 48 mg of Int-18e as a clear oil. MS (ESI) m/e (M+H$^+$): 485.2/486.2/487.3.

Step E—Synthesis of Compound 2

Potassium carbonate (77 mg), Amphos (14 mg), and Tris (dibenzylidene acetone)dipalladium (0) (5 mg), were added to a 20 mL Schlenck tube equipped with a stir bar. The tube was connected to a vacuum line, capped with a septum, and cycled between vacuum and $N_2$ five times. Intermediates Int-18e (46 mg) and Int-7h (86 mg) were added to a separate flask and dissolved in 0.6 mL of a 7:1 (by volume) DME:$H_2O$ solution. The resulting borate ester/bromide solution was added to the Schlenck tube via syringe. The tube was immediately cycled between vacuum and $N_2$ three times, then placed in an 85° C. oil bath. The reaction mixture was left stirring at 85° C. for 15 hours under $N_2$, then allowed to cool to room temperature. The reaction mixture was diluted with EtOAc (100 mL), then washed with water and brine. The resulting organic solution was filtered, dried with $MgSO_4$, filtered again, and concentrated in vacuo. A yellow oil was obtained (0.06 g). The crude product was purified via reverse phase HPLC. Using a 10%-95% $CH_3CN/H_2O$ gradient as the mobile phase. TFA (0.1% by volume) was added to each component of the mobile phase. The product was isolated as a yellow solid (37 mg). The product was repurified via sgc on a 24 g Isco Gold cartridge using a 0.5%-5% MeOH/$CH_2Cl_2$ gradient as the mobile phase. The column was subsequently flushed with a 2%-7% MeOH($NH_3$)/$CH_2Cl_2$ gradient mobile phase. Compound 2 (16 mg) eluted from the column during the methanolic ammonia flush. MS (ESI) m/e (M+H$^+$): 818.5/819.5/820.6.

Compounds 1, 3, 4 were prepared using the method described in Example 18 but substituting the appropriate dibromotoluene derivative in Step A.

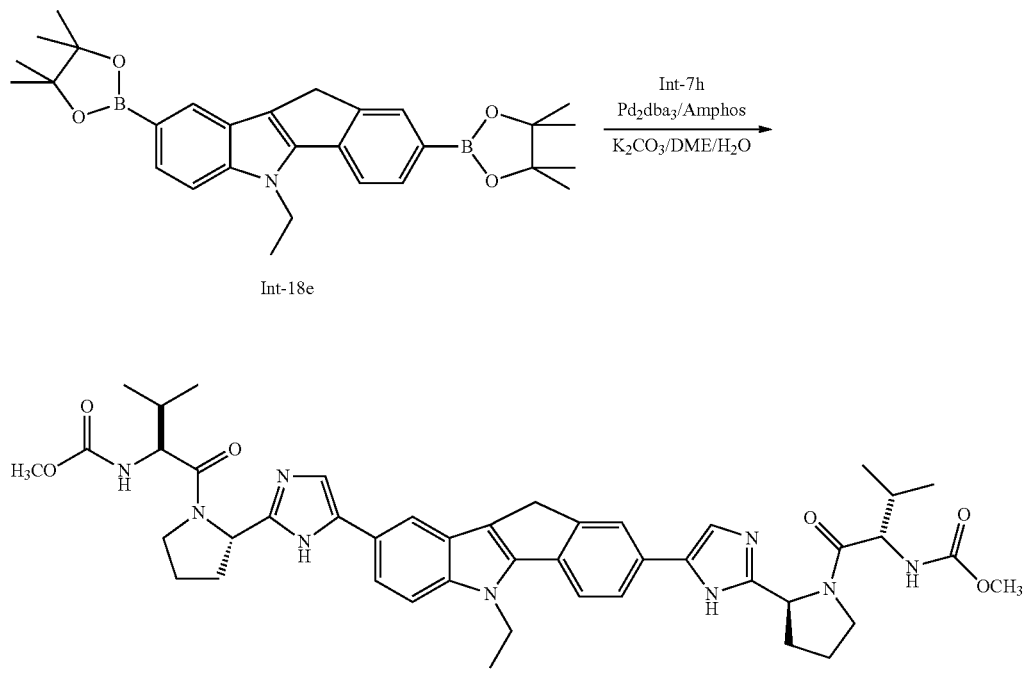

| Cpd No. | Structure | MS |
|---|---|---|
| 1 | 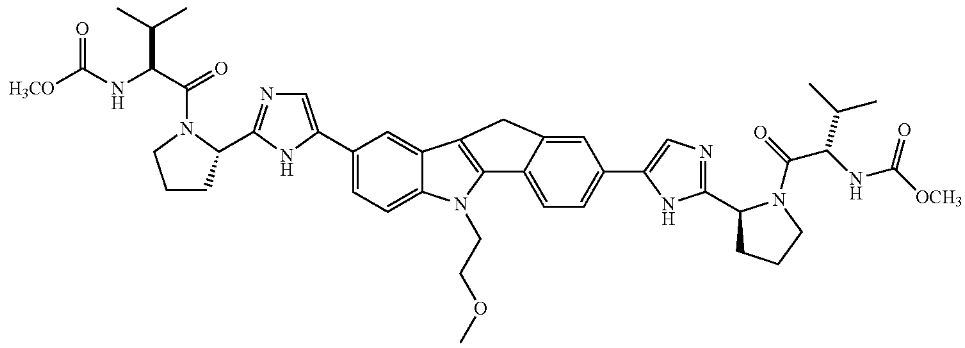 [SMILES: COCCn1c2c(c3cc(-c4cnc([C@@H]5CCCN5C(=O)[C@@H](NC(=O)OC)C(C)C)[nH]4)ccc31)Cc1cc(-c3cnc([C@@H]4CCCN4C(=O)[C@@H](NC(=O)OC)C(C)C)[nH]3)ccc1-2] | 848.6 |
| 3 | 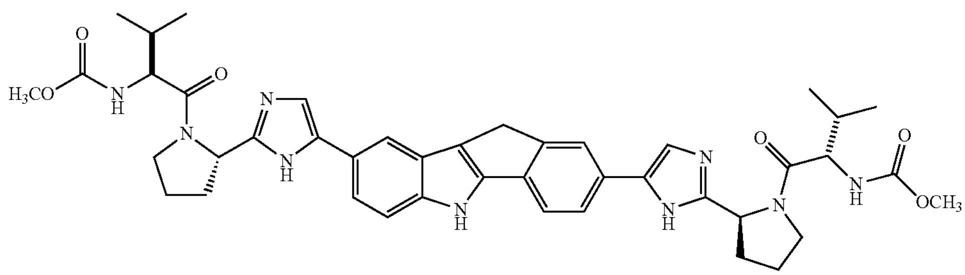 | 790.4 |
| 4 | 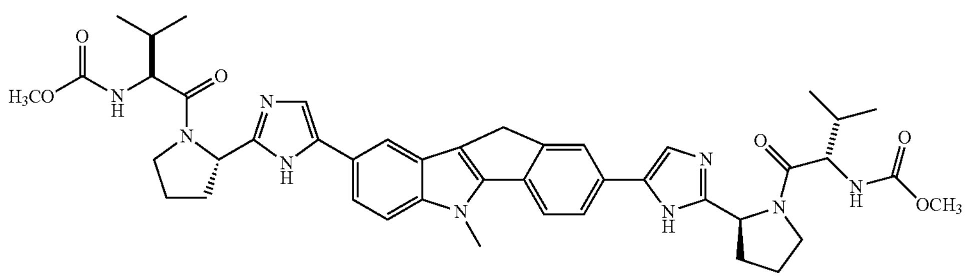 [SMILES: COC(=O)N[C@H](C(=O)N1CCC[C@H]1c1ncc(-c2ccc3c(c2)Cc2c-3n(C)c3ccc(-c4cnc([C@@H]5CCCN5C(=O)[C@@H](NC(=O)OC)C(C)C)[nH]4)cc23)[nH]1)C(C)C] | 804.4 |
Example 19
Preparation of Compound 5
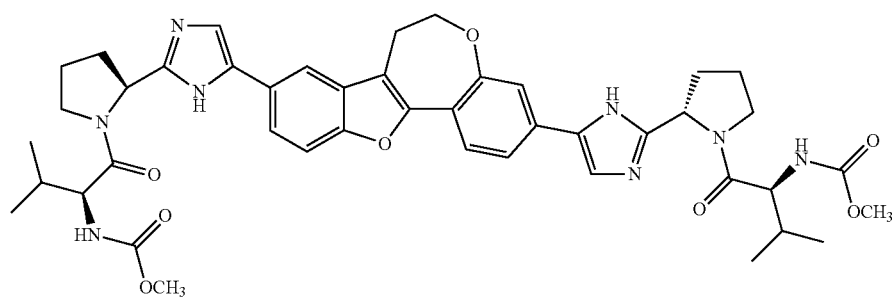 [SMILES: COC(=O)N[C@H](C(=O)N1CCC[C@H]1c1ncc(-c2ccc3c(c2)OCCc2c-3oc3ccc(-c4cnc([C@@H]5CCCN5C(=O)[C@@H](NC(=O)OC)C(C)C)[nH]4)cc23)[nH]1)C(C)C]

Step A—Synthesis of Compound Int-19c

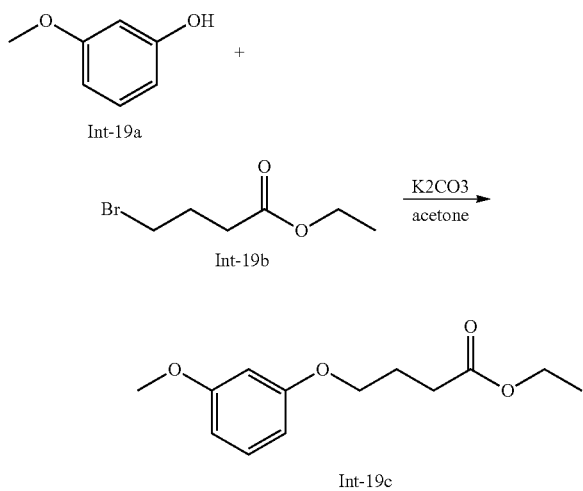

To a solution of Compound Int-19a (20 g, 0.16 mol) and Int-19b (38 g, 0.19 mol) in acetone (300 mL) was added K₂CO₃ (67 g, 0.48 mol) and the mixture was refluxed for about 15 hours. The reaction was cooled to room temperature and filtered, and the filtercake was washed with acetone. The filtrate and washings were combined and concentrated in vacuo and the residue obtained was dissolved in ethyl acetate. The resulting solution was washed with brine, dried over anhydrous Na₂SO₄, filtered and concentrated in vacuo to provide Compound Int-19c (35 g, 92%).

Step B—Synthesis of Compound Int-19d

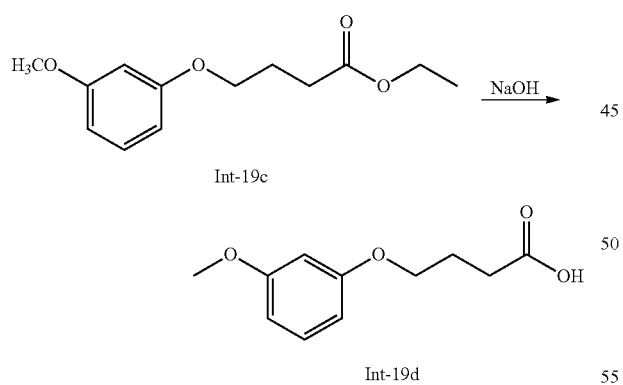

To a −5° C. solution of Int-19c (35 g, 0.14 mol) in THF/MeOH/H₂O (100 mL/100 mL/50 mL) was added LiOH/H₂O (6.7 g, 0.28 mol). The resulting reaction was allowed to stir at room temperature for about 15 hours, concentrated in vacuo and the resulting residue was dissolved in water and extracted with ethyl acetate. The aqueous layer was adjusted pH to 2-3 with (2 N) HCl and extracted with ethyl acetate. The ethyl actated layer was dried over anhydrous Na₂SO₄, filtered, and concentrated in vacuo to provide Int-19d (32 mg, 86%).

Step C—Synthesis of Compound Int-19e

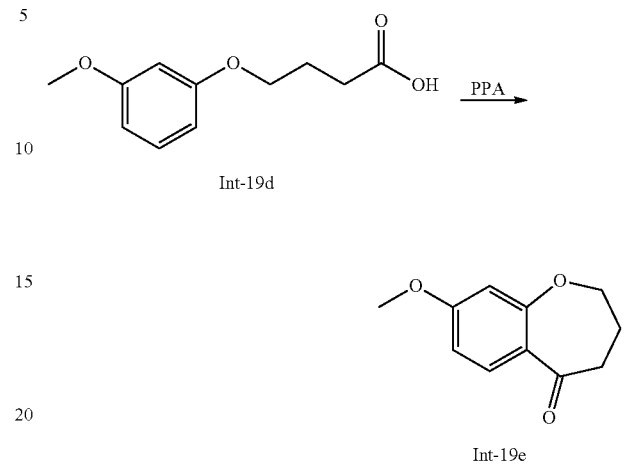

The solution of PPA in chlor-benzene was added Compound Int-19d (22 g, 0.1 mol) at 80° C. and the mixture was allowed to stir at 80° C. for about 15 hours. The solution was removed and the residue was dissolved in ethyl acetate and washed with NaOH (1N, aqueous) followed by brine. The organic layer was dried over Na₂SO₄, filtered and concentrated in vacuo to provide Compound Int-19e (14 g, 73%). ¹H NMR (CDCl₃) δ: 7.74 (d, J=8 Hz, 1H), 6.63 (d, J=8 Hz, 1H), 6.53 (s, 1H), 4.21 (t, J=12 Hz, 2H), 3.80 (s, 3H), 2.84 (t, J=16 Hz, 2H), 2.18-2.15 (m, 2H).

Step D—Synthesis of Compound Int-19f

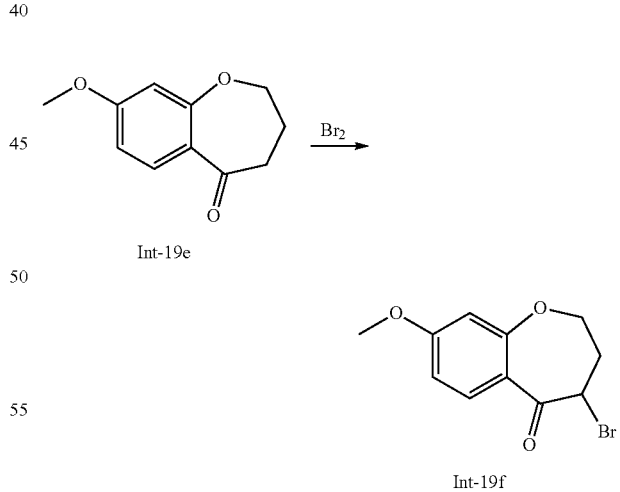

Int-19e (7.4 g, 38 mmol) was dissolved in ethyl ether and treated with a dropwise addition of Br₂ (6.2 g, 38 mmol). The solution was allowed to stir for two additional hours and then worked up by washed a 10% Na₂SO₃ solution, NaHCO₃ and brine. The organic layer was dried over Na₂SO₄, filtered and concentrated in vacuo to provide Compound Int-19f (8.3 g, 80%). ¹H NMR (CDCl₃) δ: 7.69 (d, J=8 Hz, 1H), 6.60 (d, J=8

Hz, 1H), 6.47 (s, 1H), 4.90 (t, J=16 Hz, 1H), 4.38-4.33 (m, 1H), 4.12-4.05 (m, 1H), 3.77 (s, 3H), 2.90-2.82 (m, 1H), 2.45-2.40 (m, 1H).

Step E—Synthesis of Compound Int-19g

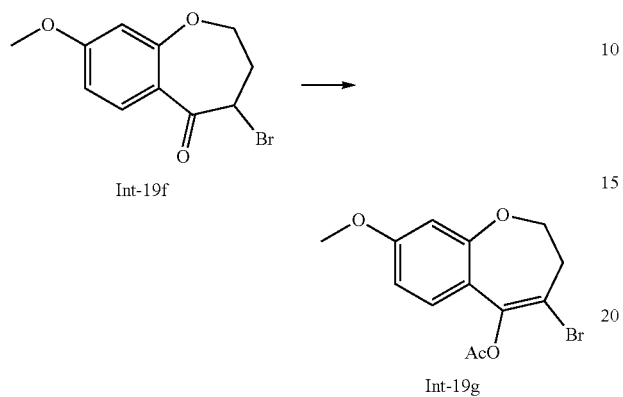

A solution of Int-19f (8.3 g, 31 mmol) in THF was cooled to −78° C. and treated with the slow addition of LiHMDS (8.2 g, 49 mmol) in THF. The reaction was allowed to stir for an addition 15 minutes at −78° C. and then treated with the rapid addition of acetic anhydride (9.4 g, 92 mmol) in THF. The reaction was allowed to stir at 0° C. for 30 minutes and then worked up by diluting the reaction mixture with ethyl ether and washed with HCl (1N), saturated $NaHCO_3$, water and brine. After drying over $Na_2SO_4$, filtered and concentrated in vacuo to provide Int-19g (9.4 g, 98%).

Step F—Synthesis of Compound Int-19h

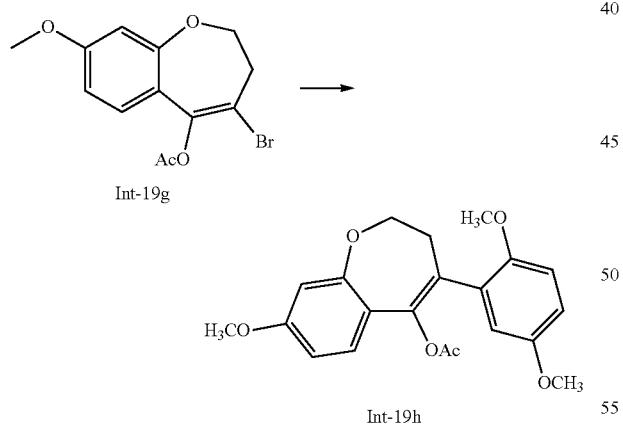

A solution of Compound Int-19g (9.4 g, 30 mmol) and 2,5-dimethoxy benzeneboronic acid (6.6 g, 36 mmol), KF (8.7 g, 0.15 mol) and $Pd(PPh_3)_4$ (1.7 g, 1.5 mmol) was heated at reflux in dioxane for about 15 hours. The solvent was removed and the residue was dissolved in ethyl acetate. The solution was washed with brine and the organic layers dried over anhydrous $Na_2SO_4$, filtered and concentrated in vacuo to provide the residue which was purified using column chromatography to provide Compound Int-19h (4.7 g, 42% yield). $^1$H NMR (MeOD) δ: 7.22 (d, J=8 Hz, 1H), 6.93 (d, J=8 Hz, 1H), 6.83 (d, J=8 Hz, 1H), 6.68 (s, 1H), 6.64-6.60 (m, 2H), 4.38-4.35 (m, 2H), 3.79 (s, 3H), 3.74 (d, J=8 Hz, 6H), 2.78 (s, 2H), 1.84 (s, 3H).

Step G—Synthesis of Compound Int-19i

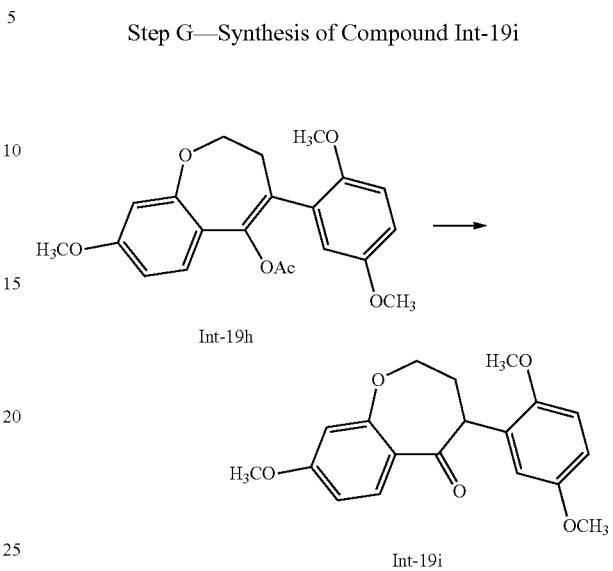

The solution Int-19h (4.7 g, 12.7 mmol) in methanol was treated with a 50% NaOH (aqueous, 30 mL) solution and stirred at room temperature until TLC indicated hydrolysis of the enol acetate was complete. The basic solution was neutralized with HCl (2N) and the solvent was removed under reduced pressure. The resultant mixture was extracted with ethyl acetate, washed with $NaHCO_3$, brine and dried over $Na_2SO_4$, filtered and concentrated in vacuo to provide Compound Int-19i (4.0 g, 95%).

Step H—Synthesis of Compound Int-19j

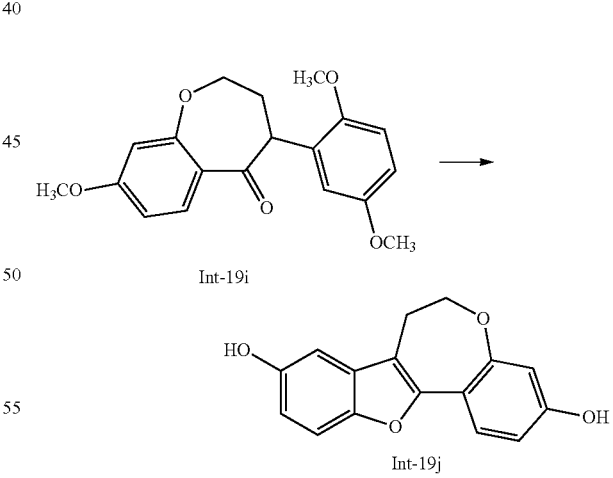

Int-19i (3.5 g, 11 mmol) in Pyr-HCl (9.8 g, 85 mmol) was heated at 200° C. for 1 hour. The reaction was allowed to cool to root temperature and worked up by partitioning between ethyl acetate and 2N HCl. The ethyl acetate layer was washed with $NaHCO_3$, brine and dried over $Na_2SO_4$, filtered, concentrated in vacuo and chromatographed to provide Compound Int-19j (2.0 g, 71%). NMR (DMSO) δ: 9.80 (s, 1H), 9.14 (s, 1H), 7.69 (d, J=8 Hz, 1H), 7.29 (d, J=8 Hz, 1H), 6.79

(s, 1H), 6.67 (d, J=12 Hz, 1H), 6.57 (d, J=12 Hz, 1H), 6.43 (s, 1H), 4.29-4.27 (m, 2H), 2.98-2.96 (m, 2H).

Step I—Synthesis of Compound Int-19k

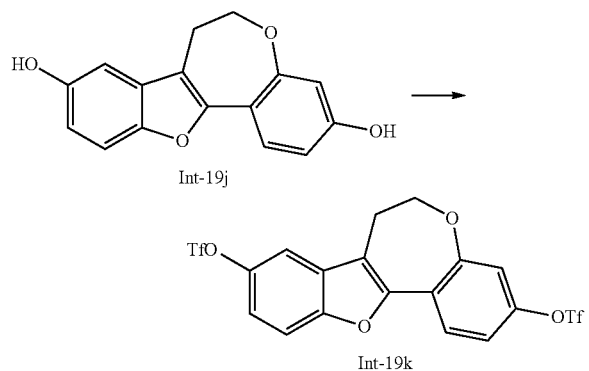

To a −10° C. solution of Int-19j (1.8 g, 6.7 mmol) and triethylamine (1.9 g, 18.8 mmol) in 100 mL of dichloromethane was added triflic anhydride (4.2 g, 14.8 mmol). The resulting reaction was allowed to stir for 1 hour before the reaction was quenched with water and extracted. The organic extract was washed with 10% citric acid, saturated $Na_2CO_3$ and brine, dried over $Na_2SO_4$, filtered and concentrated in vacuo to provide Compound Int-19k (2.6 g, 72%).

Step J—Synthesis of Compound Int-19l

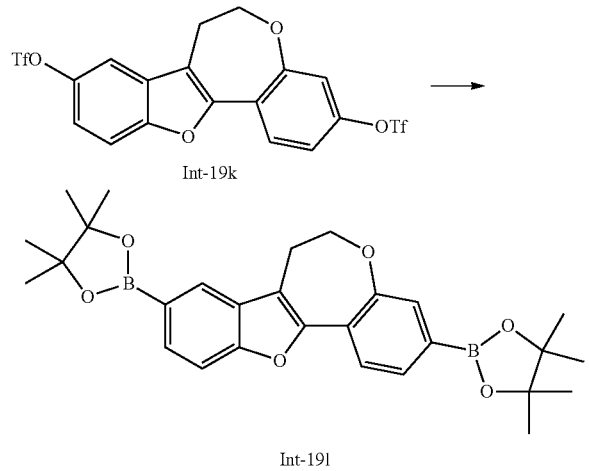

A mixture of Int-19k (2.6 g, 4.9 mmol), bis(pinacolato)diboron (2.7 g, 11 mmol), KOAc (1.9 g, 20 mmol), Pd(dppf)Cl$_2$ (0.18 g, 0.2 mmol) and dppf (0.1 g, 0.2 mmol) was degassed and sealed under $N_2$. Dry dioxane (30 mL) was added and the resulting solution was further purged with nitrogen. The resulting reaction was heated to 80° C. and was allowed to stir at this temperature for about 15 hours. The reaction mixture was cooled and diluted with 100 mL of ether. The resulting solution was washed with water (×2) then brine. The organic layer was dried over $Na_2SO_4$, filtered and concentrated in vacuo and the resulting residue which was purified using flash chromatography on silica gel to provide Compound Int-19l (1.5 g, 61%). $^1$H NMR (CDCl$_3$) δ: 8.04 (d, J=8 Hz, 1H), 7.98 (s, 1H), 7.77 (d, J=8 Hz, 1H), 7.55 (d, J=8 Hz, 1H), 7.50-7.47 (m, 2H), 4.39-4.36 (m, 2H), 3.22-3.19 (m, 2H).

Step K—Synthesis of Compound Int-19m

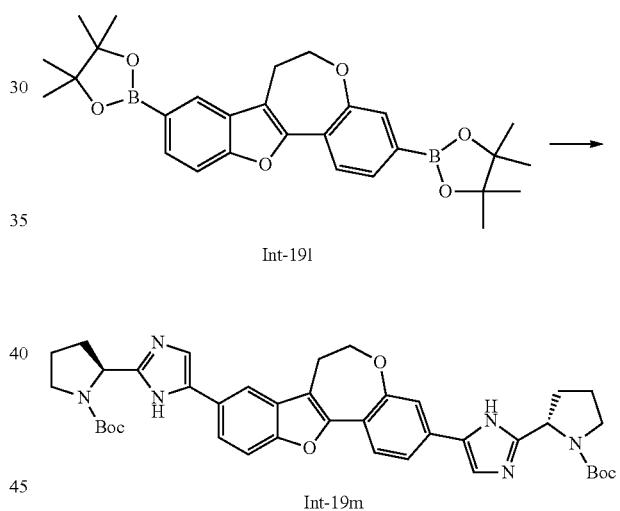

Compound Int-19m was prepared from Compound Int-19l using the method described in Example 18, step C (1 g, 71%). MS (ESI) m/z (M+H)$^+$: 707.

Step L—Synthesis of Compound Int-19n

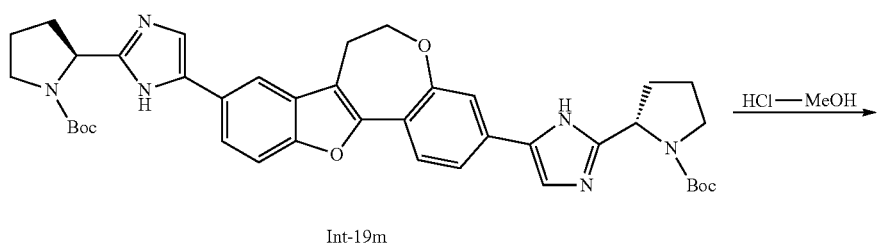

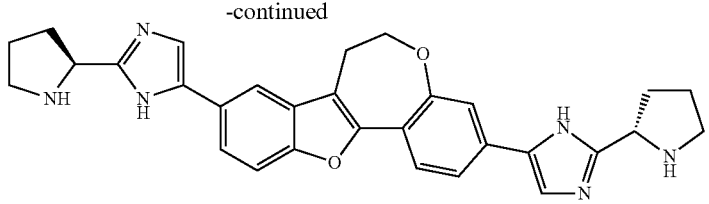

Int-19n

A solution of Compound Int-19m (1 g, 1.4 mmol) in HCl-MeOH (4N, 20 mL) was allowed to stir at room temperature for 1 hour, then the reaction mixture was concentrated in vacuo to provide Compound Int-19n (0.72 g, 78%), which was used without further purification. MS (ESI) m/z (M+H)$^+$: 507.

Step M—Synthesis of Compound 5

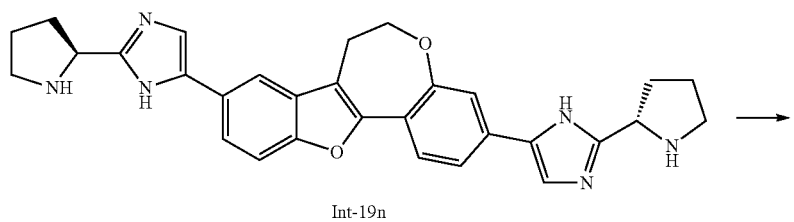

Int-19n

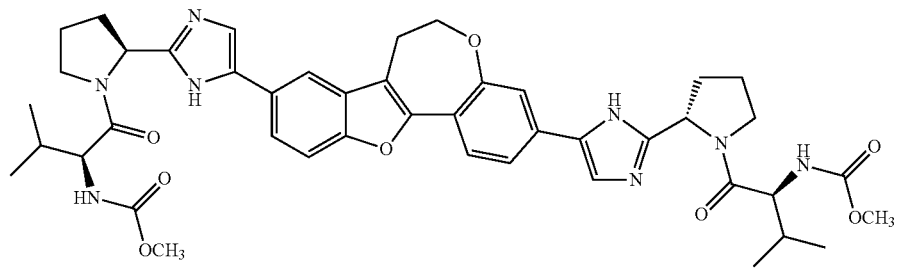

5

Compound 5 was prepared from Compound Int-19n using the method described in Example 18, step E. (0.21 g, 43%). $^1$H-NMR: (MeOD) δ: 8.11 (s, 1H), 7.89 (d, J=16 Hz, 2H), 7.80 (s, 1H), 7.65 (s, 2H), 7.51-7.44 (m, 2H), 5.24-5.22 (m, 2H), 4.51-4.42 (m, 2H), 4.31-4.18 (m, 2H), 4.15-4.04 (m, 2H), 3.80-3.95 (m, 2H), 3.64 (s, 6H), 3.31-3.17 (m, 2H), 2.57-2.48 (m, 2H), 2.27-2.06 (m, 8H), 0.90 (d, J=24 Hz, 12H).

MS (ESI) m/z (M+H)$^+$: 821.

Example 20

Preparation of Compound 6

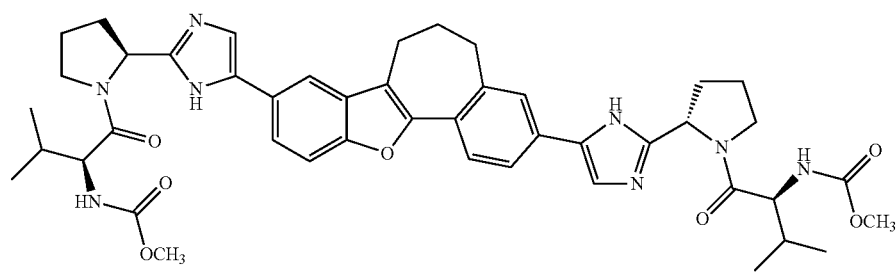

6

Step A—Synthesis of Compound Int-20c

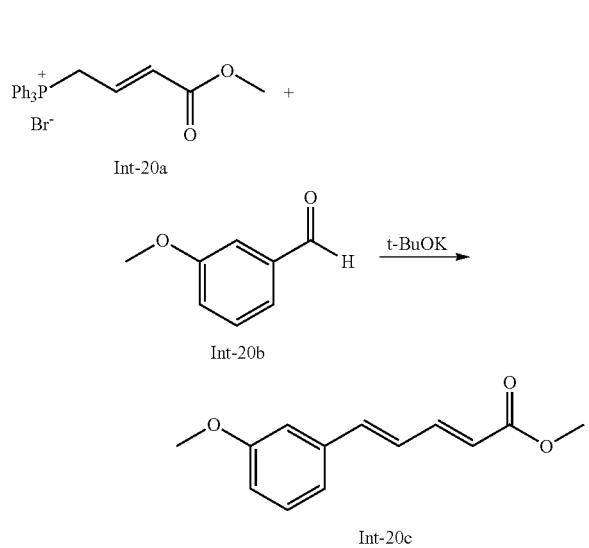

To a solution of Int-20a (16.2 g, 31.1 mmol) and Int-20b (3.64 g, 26.8 mmol) in methanol was added t-BuOK (6.6 g, 59.1 mmol) and the mixture was heated to reflux and allowed to stir at this temperature for 5 hours. The reaction mixture was then cooled to room temperature and filtered. The filtrate was diluted with water and extracted with ethyl acetate. The organic extract was washed with brine, dried over $Na_2SO_4$, filtered, concentrated in vacuo, and the resulting residue was purified using flash chromatography on silica gel to provide Compound Int-20c (4.5 g, 77%). $^1$H-NMR: (CDCl$_3$) δ: 7.41-7.34 (m, 1H), 7.22-7.18 (m, 1H), 7.99 (d, J=8 Hz, 1H), 6.91 (s, 1H), 6.81-6.79 (m, 3H), 5.93 (d, J=16 Hz, 1H), 3.76 (s, 3H), 3.70 (s, 3H).

Step B—Synthesis of Compound Int-20d

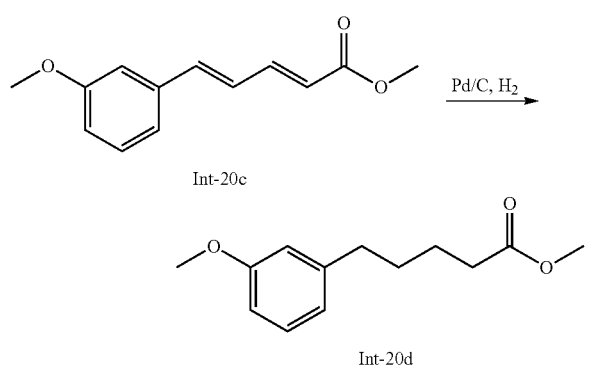

To a solution of Compound Int-20c (4.5 g, 20.6 mmol) in THF (60 mL) was added Pd/C (1 g, 10% Pd) was added. The reaction was purged with argon then put under $H_2$ atmosphere (50 psi). The reaction was allowed to stir at room temperature for 2 hours, then was concentrated in vacuo. The resulting residue was washed with n-hexane to provide Compound Int-20d (4.3 g, 95%).

Step C—Synthesis of Compound Int-20e

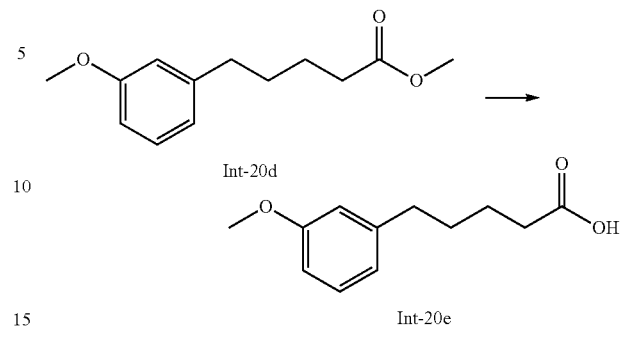

Int-20d (4 g) was dissolved in THF/MeOH/H$_2$O (10 mL/10 mL/5 mL) and the LiOH/H$_2$O (1 g) was added at −5° C. Then the resulting mixture was allowed to stir at room temperature for about 15 hours, concentrated in vacuo and then the residue was dissolved in water and extracted with ethyl acetate. The aqueous layers was adjusted PH to 2-3 with (2 N) HCl and extracted with ethyl acetate, dried over anhydrous Na$_2$SO$_4$, filtered, concentrated in vacuo to provide Compound Int-20e (4.0 g, 100%).

Step D—Synthesis of Compound Int-20f

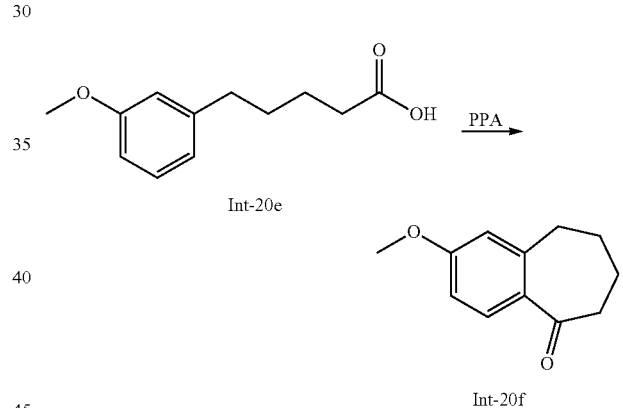

The solution of PPA in chlorobenzene was added Int-20e (4 g) at 80° C. and the mixture was allowed to stir at 80° C. for about 15 hours. The solution was removed and the residue was dissolved in ethyl acetate and washed with NaOH (1N, aqueous) followed by brine. The organic layer was dried over Na$_2$SO$_4$, filtered and concentrated in vacuo to provide Compound Int-20f (3.8 g, 100%).

Step E—Synthesis of Compound Int-20g

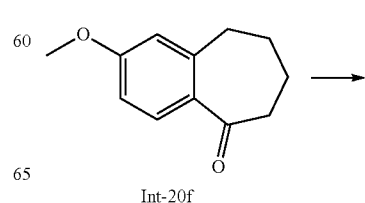

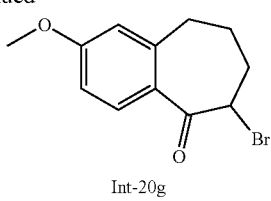

Int-20g

Int-20f (3.8 g) was dissolved in ethyl ether and treated with a dropwise addition of Br$_2$ (3.2 g). The solution was allowed to stir for two additional hours and then worked up by washed a 10% Na$_2$SO$_3$ solution, NaHCO$_3$ and brine. The organic layer was dried over Na$_2$SO$_4$, filtered and concentrated in vacuo to provide Compound Int-20g (4.0 g, 60%). $^1$H-NMR: (CDCl$_3$) δ: 7.71 (d, J=8 Hz, 1H), 7.83 (d, J=8 Hz, 1H), 6.73 (s, 1H), 4.92-4.89 (m, 1H), 3.87 (s, 3H), 3.07-3.03 (m, 1H), 2.94-2.88 (m, 1H), 2.40-2.28 (m, 2H), 2.07-2.02 (m, 2H).

Step F—Synthesis of Compound Int-20h

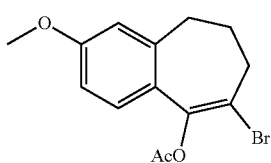

Int-20g

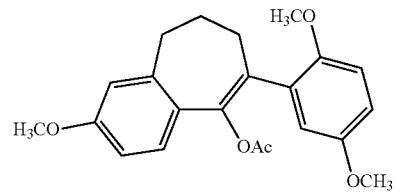

Int-20h

A solution of Int-20g (4 g) in THF was cooled to −78° C. and to the cooled solution was slowly added a solution of LiHMDS (4 g) in THF. The reaction was allowed to stir for an addition 15 minutes at −78° C. and then a solution of acetic anhydride (4.6 g) in THF was rapidly added. The reaction was allowed to stir at 0° C. for 30 minutes and then diluted with ethyl ether. The resulting solution was washed sequentially with HCl (1N), saturated NaHCO$_3$, water and brine, then was dried over Na$_2$SO$_4$, filtered and concentrated in vacuo to provide Compound Int-20h (4.0 g, 87%), which was used without further purification.

Step G—Synthesis of Compound Int-20i

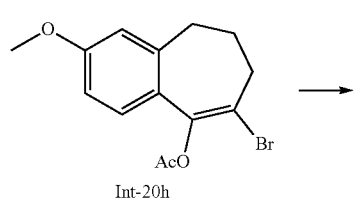

Int-20h

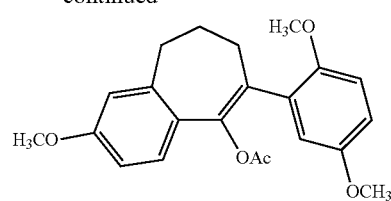

Int-20i

A solution of Compound Int-20h (3.3 g, 10 mmol) and 2,5-dimethoxy benzeneboronic acid (2.2 g, 12 mmol), KF (2.9 g, 0.5 mol) and Pd(PPh$_3$)$_4$ (0.55 g, 0.5 mmol) was heated at reflux in dioxane for about 15 hours. The solvent was removed and the residue was dissolved in ethyl acetate. The solution was washed with brine and the organic layers dried over anhydrous Na$_2$SO$_4$, filtered and concentrated in vacuo to provide the residue which was purified using column chromatography to provide Compound Int-20i (57%). $^1$H NMR: (CDCl$_3$) δ: 7.27-7.26 (m, 1H), 6.84-6.76 (m, 5H), 3.83 (s, 3H), 3.77 (s, 6H), 2.90-2.87 (m, 2H), 2.23-2.20 (m, 4H), 1.95 (s, 1H).

Step H—Synthesis of Compound Int-20j

Int-20i

Int-20j

To a solution of Compound Int-20i (2.5 g) in methanol was added a 50% aqueous NaOH (30 mL) solution and the resulting reaction was allowed to stir at room temperature until TLC indicated the reaction was complete. The reaction mixture was neutralized with HCl (2N) and the solvent was removed in vacuo. The resultant mixture was extracted with ethyl acetate and the organic extract was washed with saturated aqueous NaHCO$_3$ and brine, dried over Na$_2$SO$_4$, filtered and concentrated in vacuo to provide Compound Int-20j (2.1 g, 95%).

Step I—Synthesis of Compound Int-20k

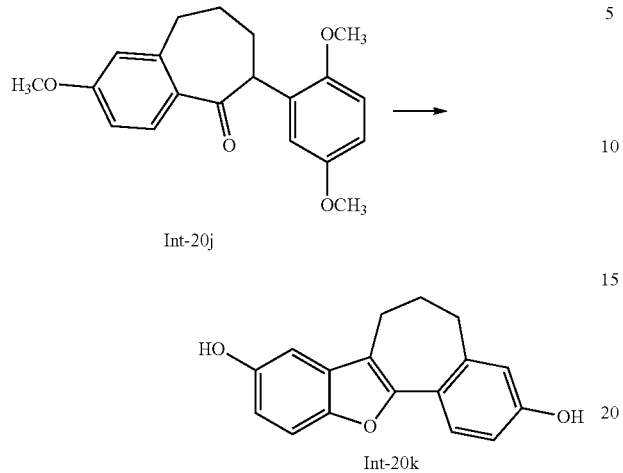

Int-20j

Int-20k

A solution of Compound Int-20j (2.1 g) in Pyr-HCl (5.8 g) was heated to 200° C. and allowed to stir at this temperature for 1 hour. The reaction was allowed to cool to room temperature, then was partitioned between ethyl acetate and 2N HCl. The ethyl acetate layer was washed with NaHCO$_3$, brine, dried over Na$_2$SO$_4$, filtered, concentrated in vacuo. The residue obtained was purified via flash column chromatography on silica gel to provide Compound Int-20k (1.66 g, 97%).

Step J—Synthesis of Compound Int-20l

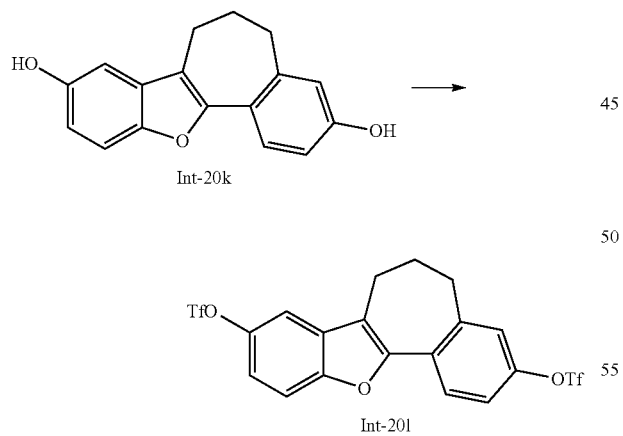

Int-20k

Int-20l

To a solution of Compound Int-20k (1.66 g) in dichloromethane at −20° C.-10° C. was added dropwise Et$_3$N (1.8 g) and then Tf$_2$O (4.1 g) slowly. After stirring for 1 hour, the solution was washed with HCl (1N) acid, after saturated Na$_2$CO$_3$ and brine. The organic layer dried over Na$_2$SO$_4$, filtered, concentrated in vacuo to provide Compound Int-20l (2.5 g, 75%). $^1$H NMR (DMSO) δ: 8.07 (d, J=8 Hz, 1H), 7.80-7.76 (m, 2H), 7.49-7.44 (m, 3H), 3.01-2.99 (m, 4H), 2.03-2.00 (m, 2H).

Step K—Synthesis of Compound Int-20m

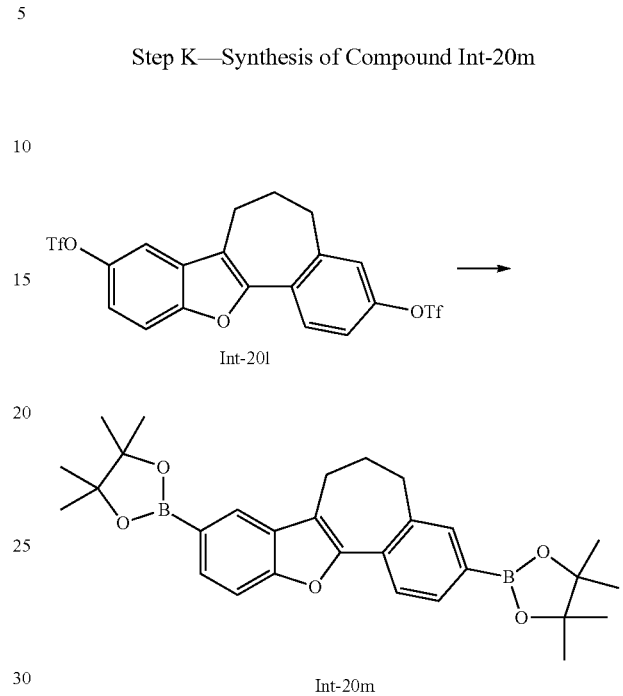

Int-20l

Int-20m

Compound Int-20m was prepared from Compound Int-20l using the method described in Example 18 step B (2.1 g, 91%). $^1$H NMR (CDCl$_3$) δ: 8.04 (d, J=8 Hz, 1H), 7.99 (s, 1H), 7.78-7.74 (m, 2H), 7.62 (s, 1H), 7.46 (d, J=8 Hz, 1H), 3.02-2.97 (m, 4H), 2.10-2.08 (m, 2H), 1.35 (d, J=4 Hz, 24H).

Step L—Synthesis of Compound Int-20n

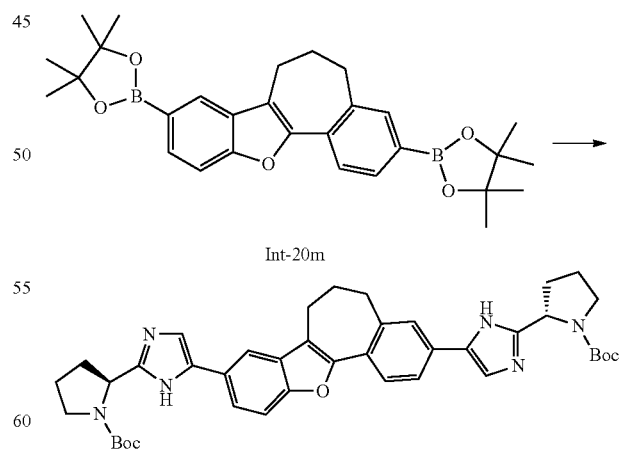

Int-20m

Int-20n

Compound Int-20n was prepared from Compound Int-20m using the method described in Example 18, step C (1.0 g, 68%). MS (ESI) m/z (M+H)$^+$: 705.

Step M—Synthesis of Compound Int-20o

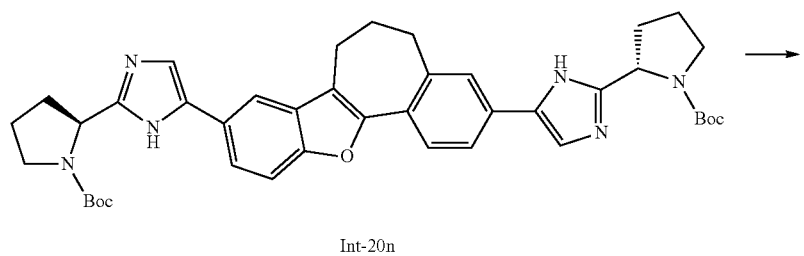

Int-20n

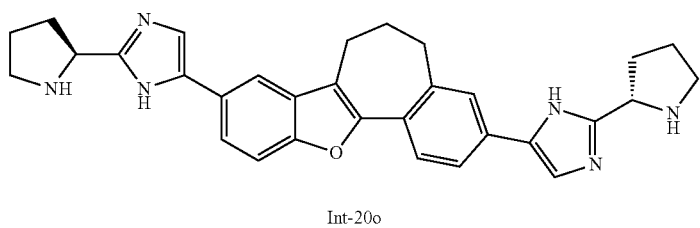

Int-20o

Compound Int-20o was prepared from Compound Int-20n using the method described in Example 18, step D (1.0 g, 71%). MS (ESI) m/z (M+H)$^+$: 505.

Step N—Synthesis of Compound 6

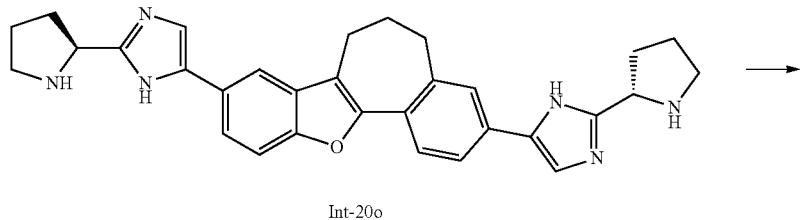

Int-20o

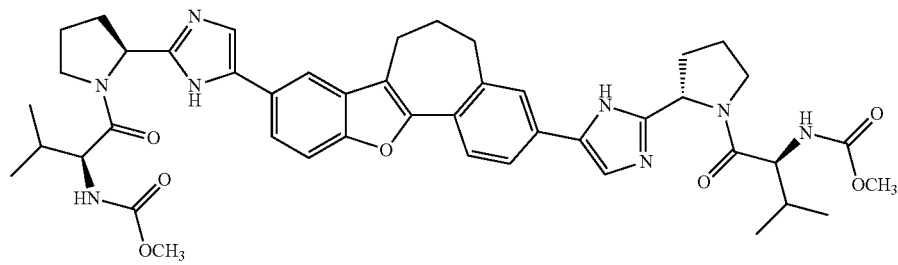

Compound 6

Compound 6 was prepared from Compound Int-20n using the method described in Example 1, step E (0.17 g, 55%). $^1$H-NMR: (MeOD) δ: 8.13 (d, J=8 Hz, 1H), 7.92 (s, 1H), 7.87 (s, 1H), 7.81 (s, 1H), 7.69-7.62 (m, 4H), 5.26-5.21 (m, 2H), 4.22 (d, J=8 Hz, 2H), 4.09-4.04 (m, 2H), 3.88-3.85 (m, 2H), 3.64 (m, 6H), 3.15-3.05 (m, 4H), 2.56-2.53 (m, 2H), 2.27-2.02 (m, 10H), 0.90 (d, J=24 Hz, 12H). MS (ESI) m/z (M+H)$^+$: 819.

The following compounds of the present invention were made using the methods described in Example 20 and substituting the appropriate reagents and/or reactants.

| Compound | Structure | MS |
|---|---|---|
| 7 | 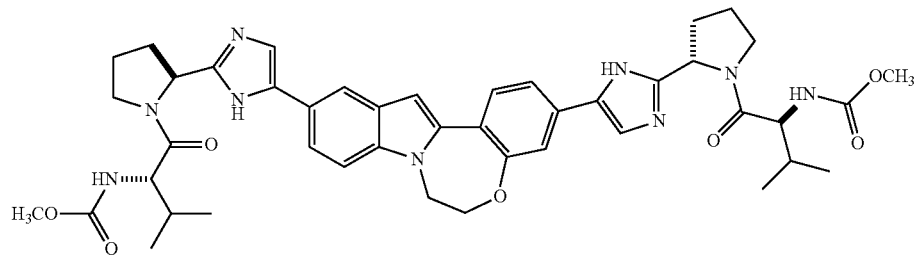 | 820 |
| 8 | 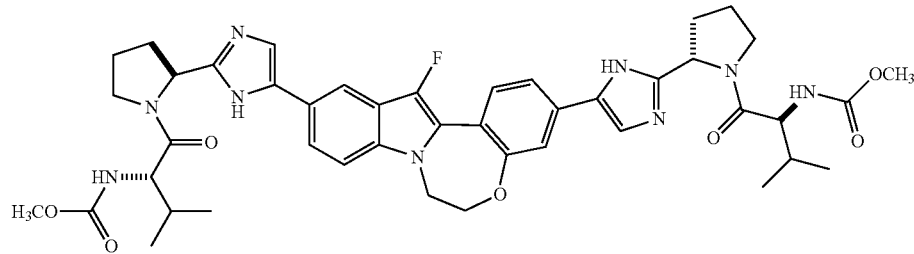 | 838 |
| 9 | 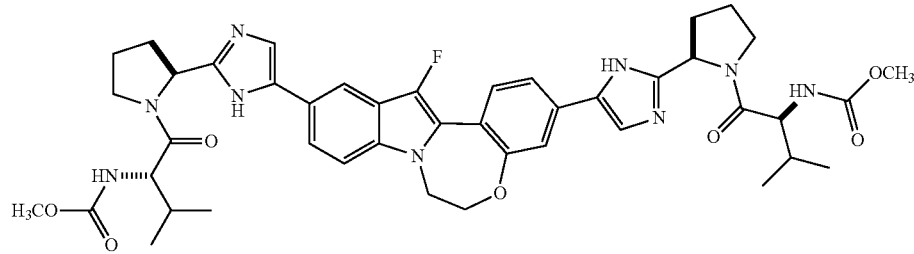 | 838 |
| 10 | 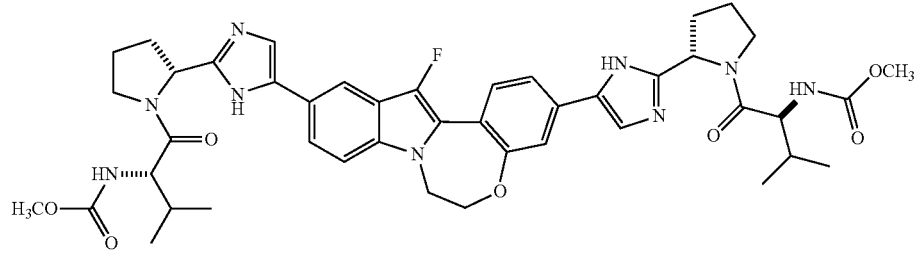 | 838 |
| 11 | 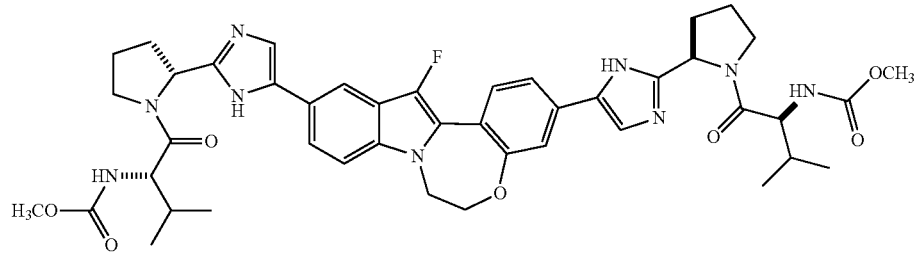 | 838 |

| Compound | Structure | MS |
|---|---|---|
| 12 | 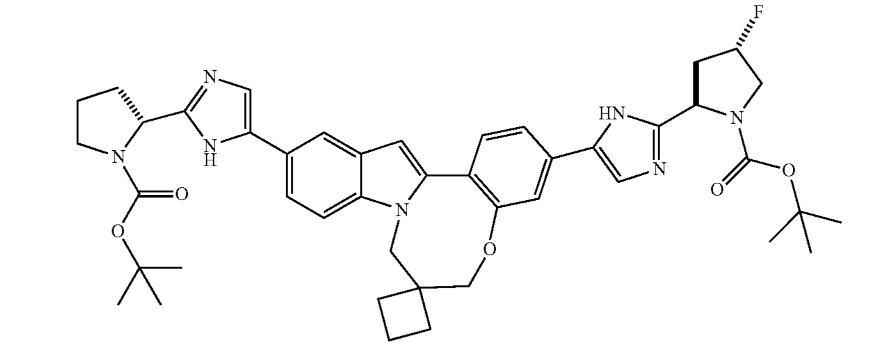 | 778 |
| 13 | 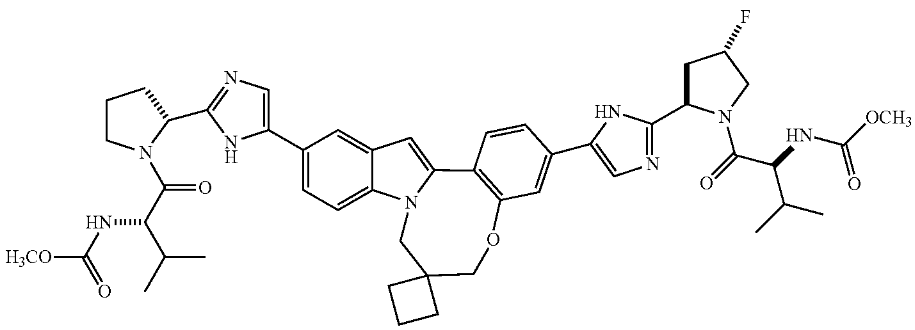 | 892 |

Example 21

Preparation of Compound 14

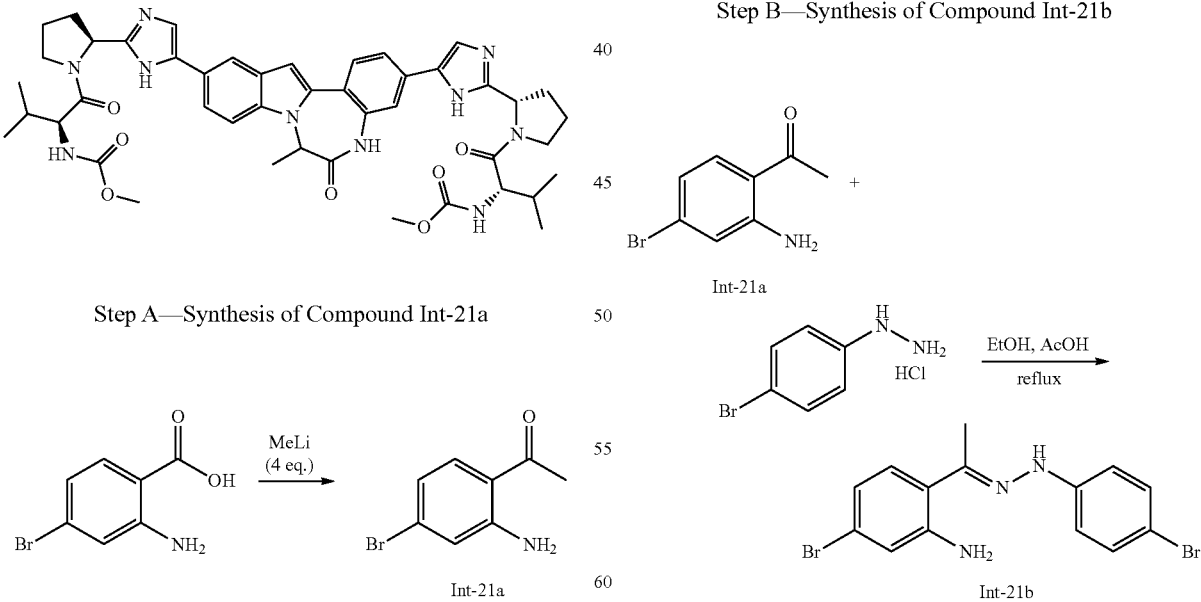

Step A—Synthesis of Compound Int-21a

To a −78° C. solution of 2-amino-4-bromobenzoic acid (2.16 g, 10 mmol) in THF (20 mL) was added MeLi (13.3 mL, 3M, 0.04 mmol). The resulting reaction was allowed to stir at −78° C. for 1 hour, then was quenched with water and extracted with EtOAc. The organic extract was dried over anhydrous $Na_2SO_4$, filtered and concentrated in vacuo and the resulting residue was purified using flash chromatography on silica gel to provide Int-21a (700 mg, 33%). $^1$H NMR (CDCl$_3$): δ 7.51-7.58 (m, 1H), 6.72-6.84 (m, 2H), 6.37 (s, 2H), 7.73 (s, 2H). MS (ESI) m/e (M+H$^+$): 214.

Step B—Synthesis of Compound Int-21b

Compound Int-21a (1 g, 4.7 mmol) and 4-bromohydrazine (1.03 g, 4.7 mmol) were taken up in a solution of AcOH in EtOH (18 mL, 10%) and the resulting reaction was heated to reflux and allowed to stir at this temperature for 4 hours. The reaction mixture was cooled to room temperature, then concentrated in vacuo to provide Compound Int-21b as a solid, which was used without further purification. MS (ESI) m/e (M+H⁺): 384.

Step C—Synthesis of Compound Int-21c

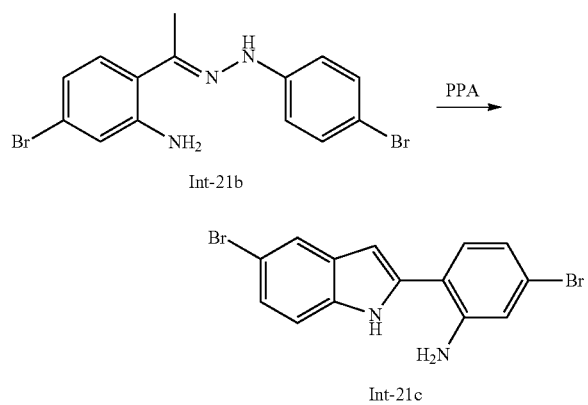

A solution of Int-21b (1.5 g, crude) in PPA (25 mL), was heated to 120° C. and allowed to stir at this temperature for 2 hours. After cooling to room temperature the reaction mixture was poured into ice water, extracted with EtOAc, dried over anhydrous Na₂SO₄, filtered and concentrated in vacuo. The residue obtained was purified using flash chromatography on silca gel to provide Int-21c (700 mg, 52%). MS (ESI) m/e (M+H⁺): 367.

Step D—Synthesis of Compound Int-21d

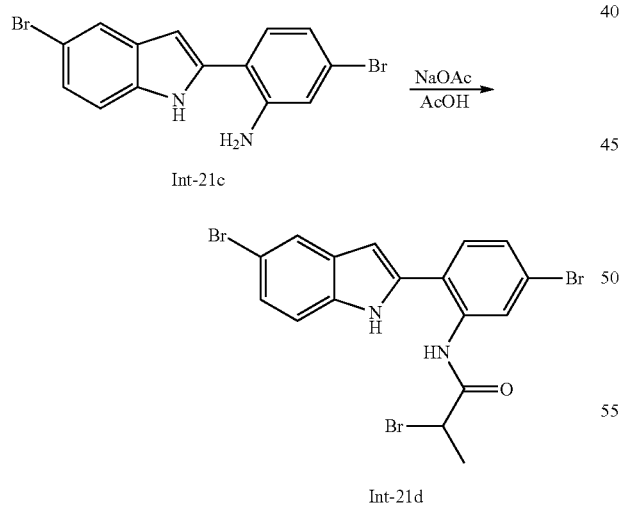

To a 0° C. mixture of Int-21c (1.25 g, 3.4 mmol), NaOAc (336 mg, 4.1 mmol) and HOAc (246 mg, 4.1 mmol) in 10 mL of dry THF was added 2-bromopropanoyl bromide (880 mg, 4.1 mmol) dropwise. The reaction was allowed to stir at room temperature for about 15 hours, then a saturated aqueous Na₂CO₃ solution was added and the mixture was extracted with dichloromethane (2×10 mL). The combined organic extracts were washed with brine, dried over Na₂SO₄, filtered and concentrated in vacuo. The resulting residue was purified using preparative HPLC to provide Int-21d as a solid (0.85 g, 50%). ¹HNMR (CDCl₃): δ 8.72 (s, 1H), 8.62 (s, 1H), 8.32 (s, 1H), 832-8.46 (s, 4H), 6.72 (s, 1H), 4.51 (q, J=7.2 Hz, 1H), 1.94 (d, J=7.2 Hz, 3H). MS (ESI) m/e (M+H⁺): 501.

Step E—Synthesis of Compound Int-21e

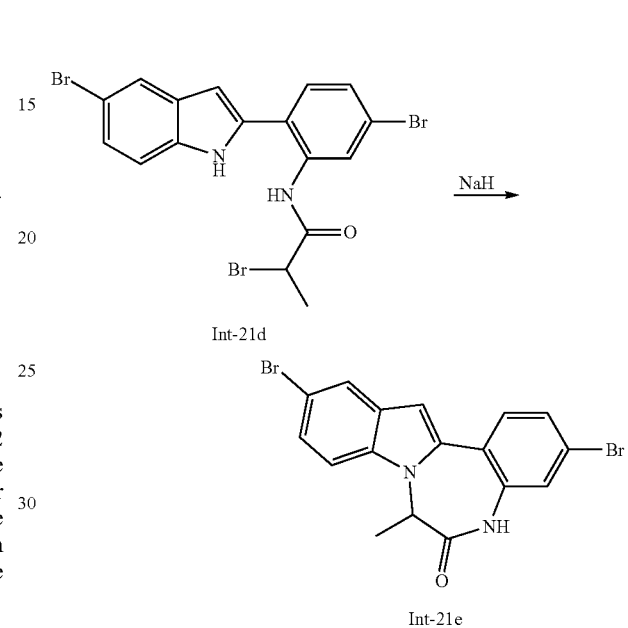

To a 0° C. solution of Int-21d (190 mg, 0.38 mmol) in THF (8 mL) was added NaH (18 mg, 0.45 mmol, 60% in a mineral oil) in an ice-water bath and stirred at room temperature for about 15 hours. The reaction mixture was diluted with water, extracted with dichloromethane (2×5 mL) and the combined organic extracts were washed with brine, dried over Na₂SO₄, filtered and concentrated in vacuo to provide Compound Int-21e as a solid (130 mg, 81%). ¹H NMR (DMSO): δ 10.57 (s, 1H), 7.80 (s, 1H), 7.70-7.23 (m, 2H), 7.40-7.43 (m, 2H), 7.28-7.30 (m, 1H), 6.89 (s, 1H), 5.51 (q, J=7.2 Hz, 1H), 1.24 (d, J=7.2 Hz, 3H). MS (ESI) m/e (M+H⁺): 421.

Step F—Synthesis of Compound 14

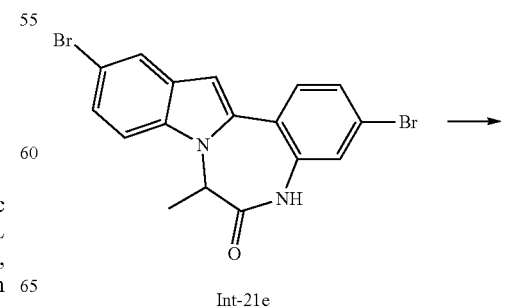

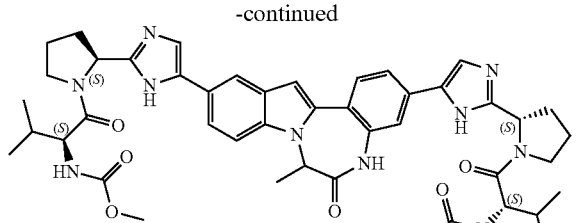

14

Compound 14 was prepared from Compound Int-21e using the method described in Example 18, steps D and E (70 mg, 21%). $^1$HNMR (MeOD): δ 7.97-7.99 (m, 2H), 7.86 (s, 1H), 7.73-7.75 (m, 2H), 7.58-7.62 (m, 2H), 7.50 (s, 1H), 7.04 (s, 1H), 5.57 (d, J=7.2 Hz, 1H), 5.21-5.25 (m, 2H), 4.22 (d, J=6.4 Hz, 2H), 4.09 (bs, 2H), 3.86 (bs, 2H), 3.64 (s, 6H), 2.54-2.56 (m, 2H), 2.02-2.07 (m, 8H), 1.04 (d, J=6.8 Hz, 3H), 0.88-0.93 (m, 12H). MS (ESI) m/e (M+H$^+$): 847.

Compound 15 of the present invention was made in a similar manner to that described above in Example 21.

7900HT Sequence Detection System using the following program: 48° C. for 30 minutes, 95° C. for 10 minutes, 40 cycles of 95° C. for 15 sec, 60° C. for 1 minutes The ΔCT values ($CT_{5B}$-$CT_{GAPDH}$) were plotted against the concentration of test compound and fitted to the sigmoid dose-response model using XLfit4 (MDL). $EC_{50}$ was defined as the concentration of inhibitor necessary to achieve ΔCT=1 over the projected baseline; $EC_{90}$ the concentration necessary to achieve ΔCT=3.2 over the baseline. Alternatively, to quantitate the absolute amount of replicon RNA, a standard curve was established by including serially diluted T7 transcripts of replicon RNA in the Taqman assay. All Taqman reagents were from PE Applied Biosystems. Such an assay procedure was described in detail in e.g. Malcolm et al., *Antimicrobial Agents and Chemotherapy* 50: 1013-1020 (2006).

HCV replicon assay data was calculated for selected compounds of the present invention using this method and is provided in the table below. Replicon $EC_{50}$ data for selected compounds of the present invention is provided in the table below.

| Compound No. | Structure | MS (M + H)+ |
|---|---|---|
| 15 | (structure) | 876 |

Example 22

Cell-Based HCV Replicon Assay

To measure cell-based anti-HCV activity of selected compounds of the present invention, replicon cells were seeded at 5000 cells/well in 96-well collagen I-coated Nunc plates in the presence of the test compound. Various concentrations of test compound, typically in 10 serial 2-fold dilutions, were added to the assay mixture, with the starting concentration ranging from 250 μM to 1 μM. The final concentration of DMSO was 0.5%, fetal bovine serum was 5%, in the assay media. Cells were harvested on day 3 by the addition of 1× cell lysis buffer (Ambion cat #8721). The replicon RNA level was measured using real time PCR (Taqman assay). The amplicon was located in 5B. The PCR primers were: 5B.2F, ATGGACAGGCGCCCTGA (SEQ ID NO. 1); 5B.2R, TTGATGGGCAGCTTGGTTTC (SEQ ID NO. 2); the probe sequence was FAM-labeled CACGCCATGCGCTGCGG (SEQ ID NO. 3). GAPDH RNA was used as endogenous control and was amplified in the same reaction as NS5B (multiplex PCR) using primers and VIC-labeled probe recommended by the manufacturer (PE Applied Biosystem). The real-time RT-PCR reactions were run on ABI PRISM

| Compound No. | 1a WT (nM) | 1b WT (nM) | 1a Y93H (nM) |
|---|---|---|---|
| 5 | 0.015 | 0.001 | 186 |
| 7 | 0.01 | 0.003 | 565 |
| 8 | 0.016 | 0.007 | ND |
| 9 | 1.18 | 0.27 | ND |
| 10 | 2 | 0.7 | ND |
| 11 | 0.01 | 0.005 | ND |

ND = not determined

The present invention is not to be limited by the specific embodiments disclosed in the examples that are intended as illustrations of a few aspects of the invention and any embodiments that are functionally equivalent are within the scope of this invention. Indeed, various modifications of the invention in addition to those shown and described herein will become apparent to those skilled in the art and are intended to fall within the scope of the appended claims.

A number of references have been cited herein, the entire disclosures of which are incorporated herein by reference.

The invention claimed is:

1. A compound having the formula:

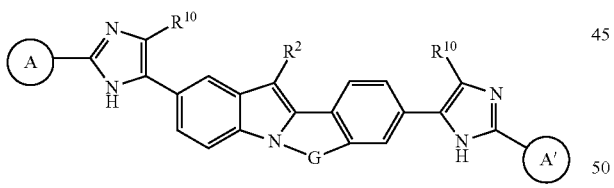

(Ia)

or a pharmaceutically acceptable salt thereof, wherein:

A and A' are each independently a 5-membered monocyclic heterocycloalkyl, wherein said 5-membered monocyclic heterocycloalkyl group can be optionally and independently substituted on one or more ring carbon atoms with $R^{13}$, such that any two $R^{13}$ groups on the same ring, together with the carbon atom(s) to which they are attached, can join to form a fused, bridged or spirocyclic 3 to 6-membered cycloalkyl group or a fused, bridged or spirocyclic 4 to 6-membered heterocycloalkyl group, wherein said 5-membered monocyclic heterocycloalkyl contains from 1 to 2 ring heteroatoms, each independently selected from $N(R^4)$ and $Si(R^{16})_2$;

G is selected from $—C(R^{3a})_2—C(R^3)_2—O—$, $—C(R^3)_2—C(R^3)_2—C(R^3)_2—O—$, $—C(R^3)_2—C(R^3)_2—N(R^5)—$ and $C(R^3)_2—C(O)—N(R^5)—$;

$R^2$ is selected from H, $C_1$-$C_6$ alkyl and halo;

each occurrence of $R^3$ is independently selected from H or $C_1$-$C_6$ alkyl and wherein two $R^3$ groups that are attached to the same carbon atom, together with the carbon atom to which they are attached, join to form a spirocyclic 3 to 6-membered cycloalkyl group;

both $R^{3a}$ groups, together with the common carbon atom to which they are each attached, join to form a spirocyclic 3-6 membered carbocyclic group or a spirocyclic 3 to 6-membered heterocycloalkyl group;

each occurrence of $R^4$ is independently selected from $—C(O)R^{11}$ and $—C(O)—[C(R^7)_2]N(R^6)C(O)O—R^{11}$;

$R^5$ is selected from H, $C_1$-$C_6$ alkyl and aryl;

each occurrence of $R^6$ is independently selected from H and $C_1$-$C_6$ alkyl;

each occurrence of $R^7$ is independently selected from $C_1$-$C_6$ alkyl, 3 to 6-membered cycloalkyl and aryl;

each occurrence of $R^{10}$ is independently selected from H and halo;

each occurrence of $R^{11}$ is independently $C_1$-$C_6$ alkyl;

each occurrence of $R^{13}$ is independently selected from H, $C_1$-$C_6$ alkyl and halo; and each occurrence of $R^{16}$ is independently $C_1$-$C_6$ alkyl.

2. The compound of claim 1, wherein the group:
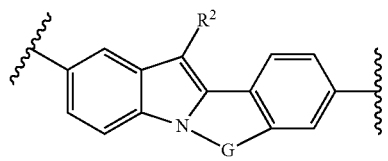
has the structure:
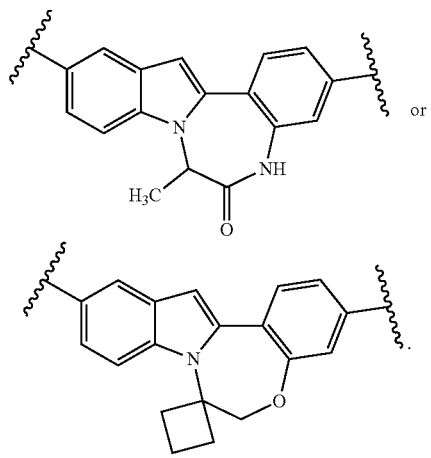
3. The compound of claim 1, wherein A and A' are each:
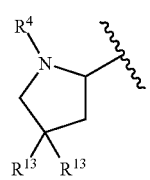
and each occurrence of $R^{13}$ is independently H, $CH_3$ or F.
4. The compound of claim 1, wherein each occurrence of $R^4$ is independently —C(O)CH($R^7$)NHC(O)O—$R^{11}$.
5. The compound of claim 3, wherein each occurrence of $R^4$ is:
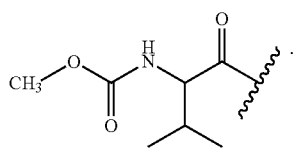 [SMILES: *C(=O)C(NC(=O)OC)C(C)C]
6. A compound having the structure:
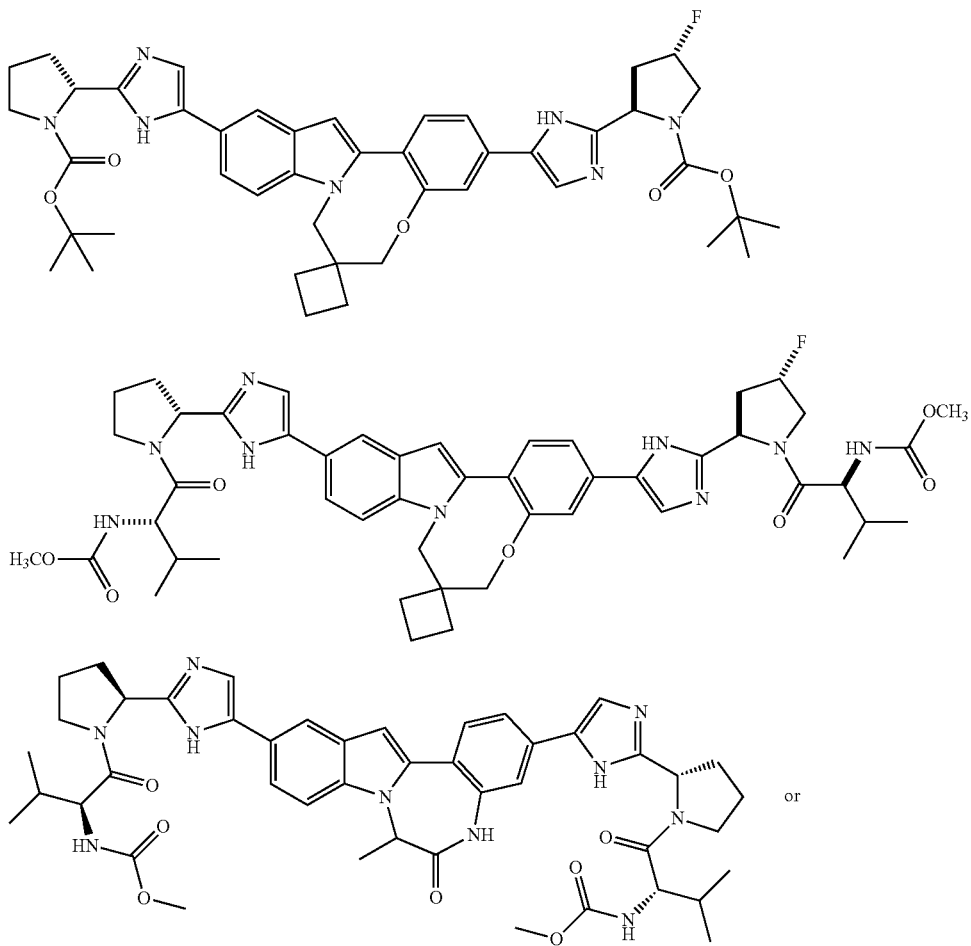

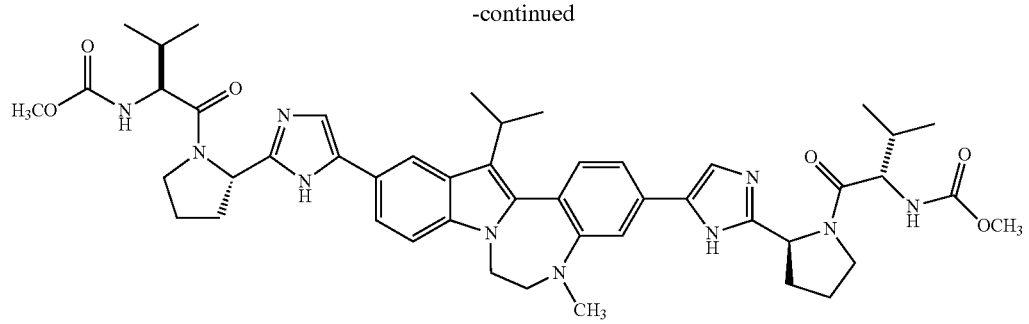

or a pharmaceutically acceptable salt thereof.

7. A pharmaceutical composition comprising an effective amount of the compound of claim 2 and a pharmaceutically acceptable carrier.

8. The pharmaceutical composition according to claim 7, further comprising a second therapeutic agent selected from the group consisting of HCV antiviral agents, immunomodulators, and anti-infective agents.

9. The pharmaceutical composition according to claim 8, further comprising a third therapeutic agent selected from the group consisting of HCV protease inhibitors, HCV NS5A inhibitors and HCV NS5B polymerase inhibitors.

* * * * *

SEQUENCE LISTING

```
<160> NUMBER OF SEQ ID NOS: 3

<210> SEQ ID NO 1
<211> LENGTH: 17
<212> TYPE: DNA
<213> ORGANISM: Artificial Sequence
<220> FEATURE:
<223> OTHER INFORMATION: 5B.2F Primer

<400> SEQUENCE: 1
atggacaggc gccctga                                                  17

<210> SEQ ID NO 2
<211> LENGTH: 20
<212> TYPE: DNA
<213> ORGANISM: Artificial Sequence
<220> FEATURE:
<223> OTHER INFORMATION: 5B.2R Primer

<400> SEQUENCE: 2
ttgatgggca gcttggtttc                                               20

<210> SEQ ID NO 3
<211> LENGTH: 17
<212> TYPE: DNA
<213> ORGANISM: Artificial Sequence
<220> FEATURE:
<223> OTHER INFORMATION: FAM labeled probe

<400> SEQUENCE: 3
cacgccatgc gctgcgg                                                  17
```